United States Patent [19]
Cohen

[11] Patent Number: 5,174,289
[45] Date of Patent: Dec. 29, 1992

[54] PACING SYSTEMS AND METHODS FOR CONTROL OF THE VENTRICULAR ACTIVATION SEQUENCE

[76] Inventor: Fred M. Cohen, 2601 E. Vogel Ave., Phoenix, Ariz. 85028

[21] Appl. No.: 578,536

[22] Filed: Sep. 7, 1990

[51] Int. Cl.⁵ ............................................. A61N 1/368
[52] U.S. Cl. .................................................. 128/419 PG
[58] Field of Search .............. 128/786 P, 419, 419 PG

[56] References Cited

U.S. PATENT DOCUMENTS

| | | | |
|---|---|---|---|
| 3,893,461 | 7/1975 | Preston | 128/786 |
| 4,088,140 | 5/1978 | Rockland et al. | 128/419 PG |
| 4,126,139 | 11/1978 | Walters et al. | 128/419 PG |
| 4,444,195 | 4/1984 | Gold | 128/786 |
| 4,554,922 | 11/1985 | Prystowsky et al. | 128/419 PG |
| 4,628,934 | 12/1986 | Ponndorf et al. | 128/786 |
| 4,787,389 | 11/1988 | Tarjan | 128/419 PG |
| 4,928,688 | 5/1990 | Mower | 128/419 PG |
| 4,967,749 | 11/1990 | Cohen | 128/419 PG |
| 5,018,523 | 5/1991 | Bach, Jr. et al. | 128/419 PG |

FOREIGN PATENT DOCUMENTS 0030897 6/1981 European Pat. Off. ..... 128/419 PG

*Primary Examiner*—William E. Kamm
*Attorney, Agent, or Firm*—Richard G. Harrer; Charles E. Cates

[57] ABSTRACT

Apparatus and methods for improving the ventricular activation sequence of the heart by pacing at an advantageous selected ventricular location to achieve shortening of the QRS complex or pacing at multiple advantageous selected ventricular locations, either simultaneously or with a programmed delay or delays between firings, to achieve shortening of the QRS complex in combination with producing a desirable and efficient ventricular motion. During a cardiac cycle initiated by intrinsic cardiac activity, stimulating impulses may be directed to advantageous selected locations of the ventricles by employing intrinsic cardiac signals to trigger the stimulating impulses, either simultaneously or with a programmed delay or delays between the sensed event or events and firing event or events, to provide improved mechanical and electrical ventricular function.

57 Claims, 32 Drawing Sheets

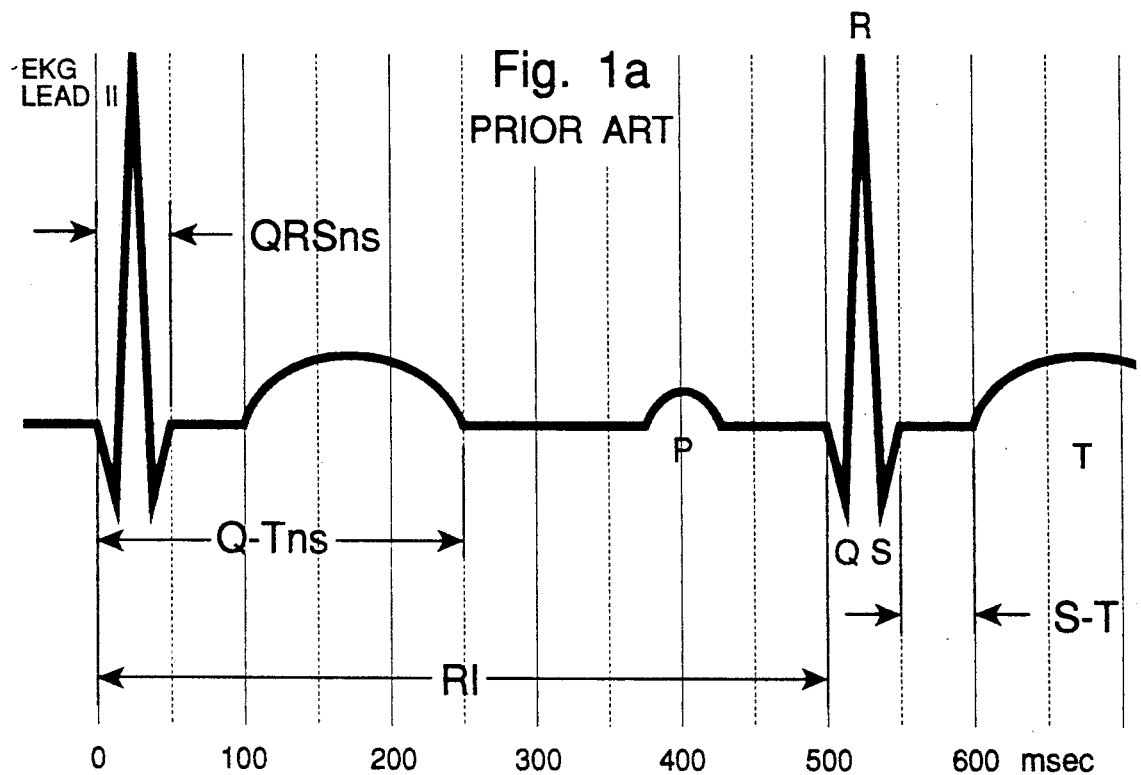
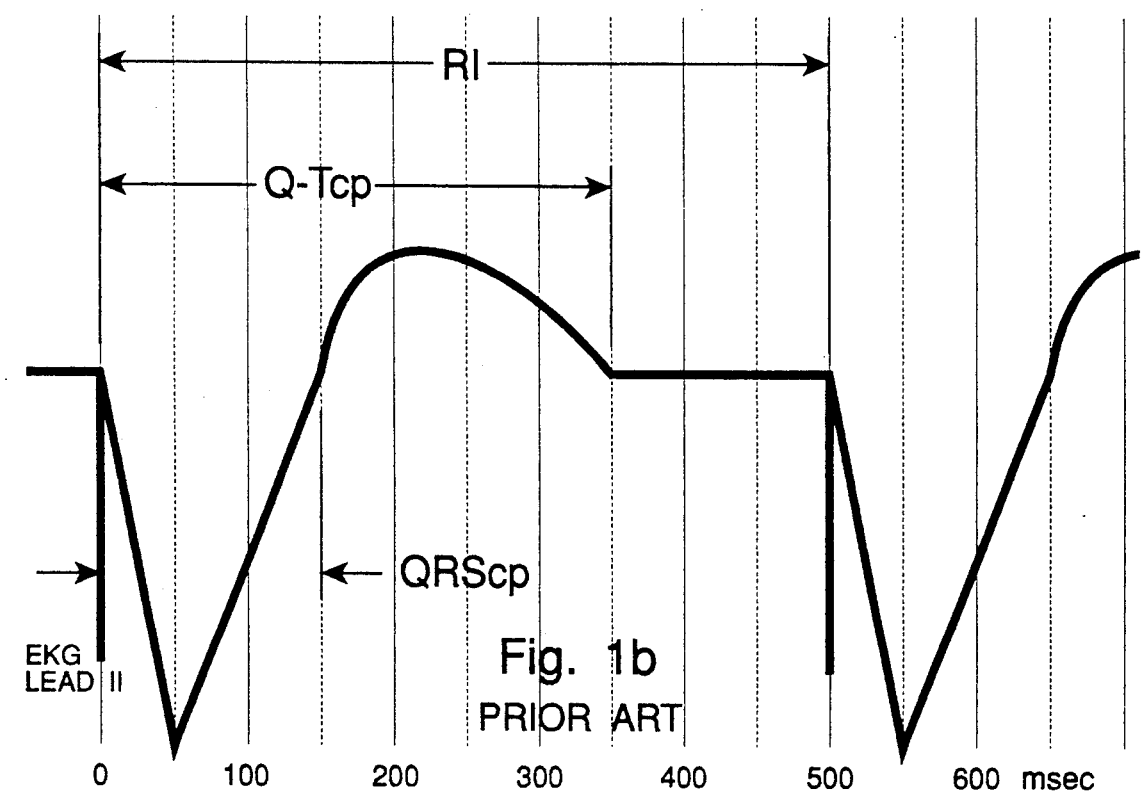

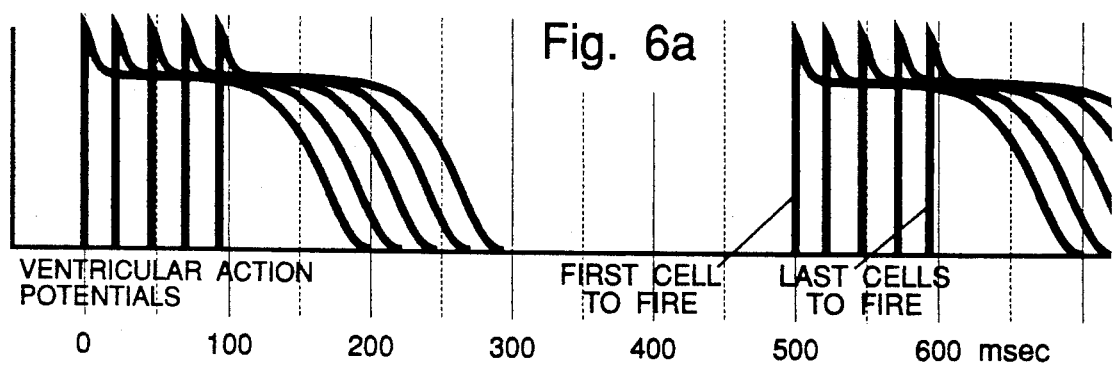
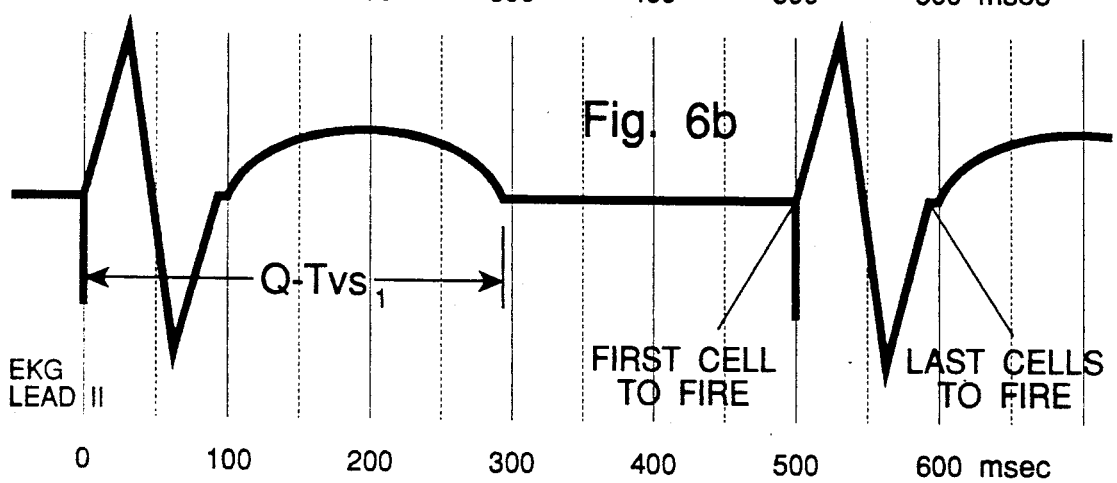
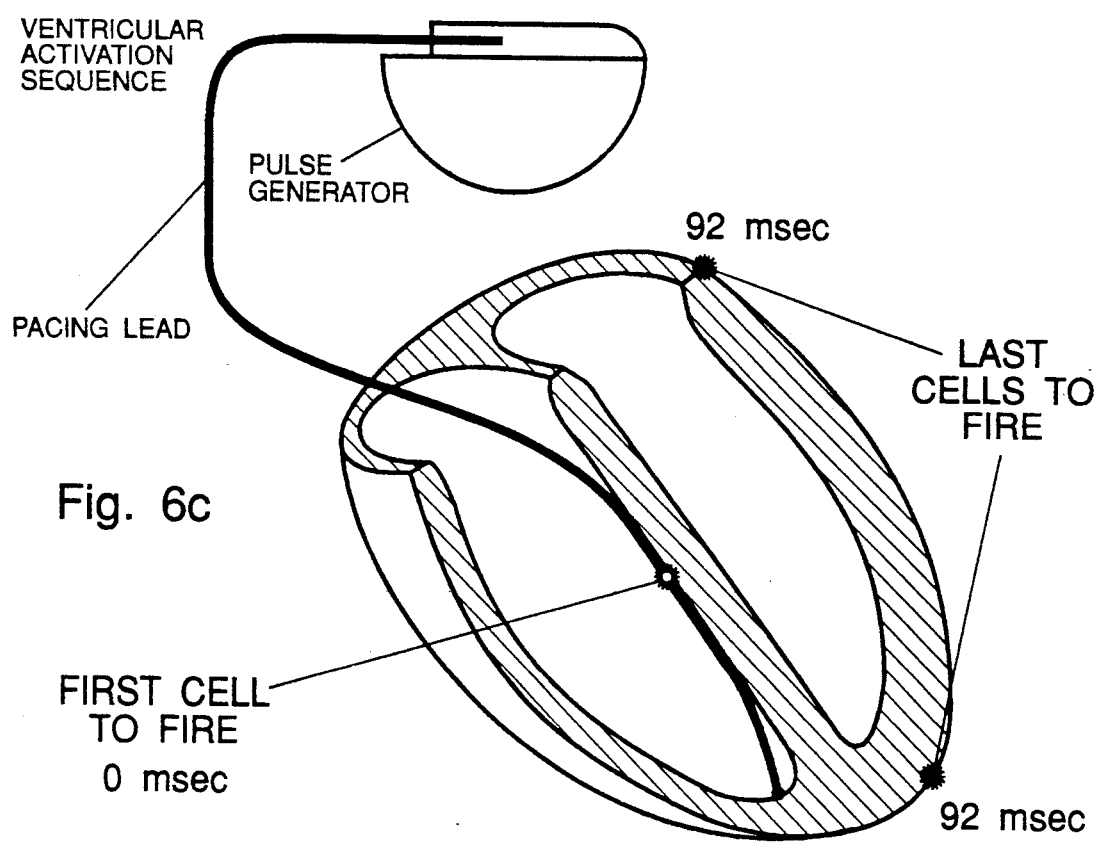

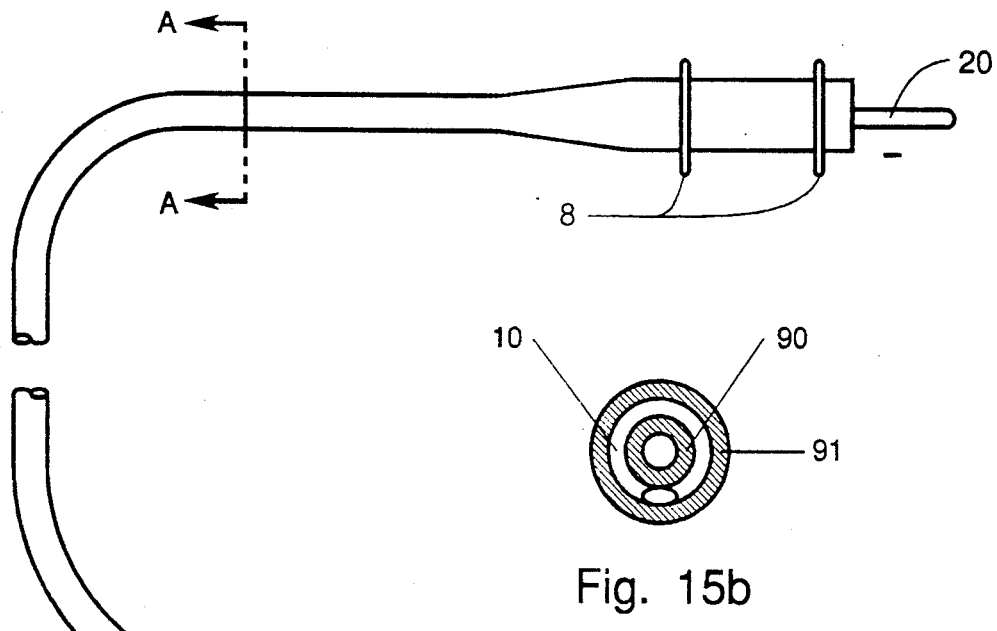
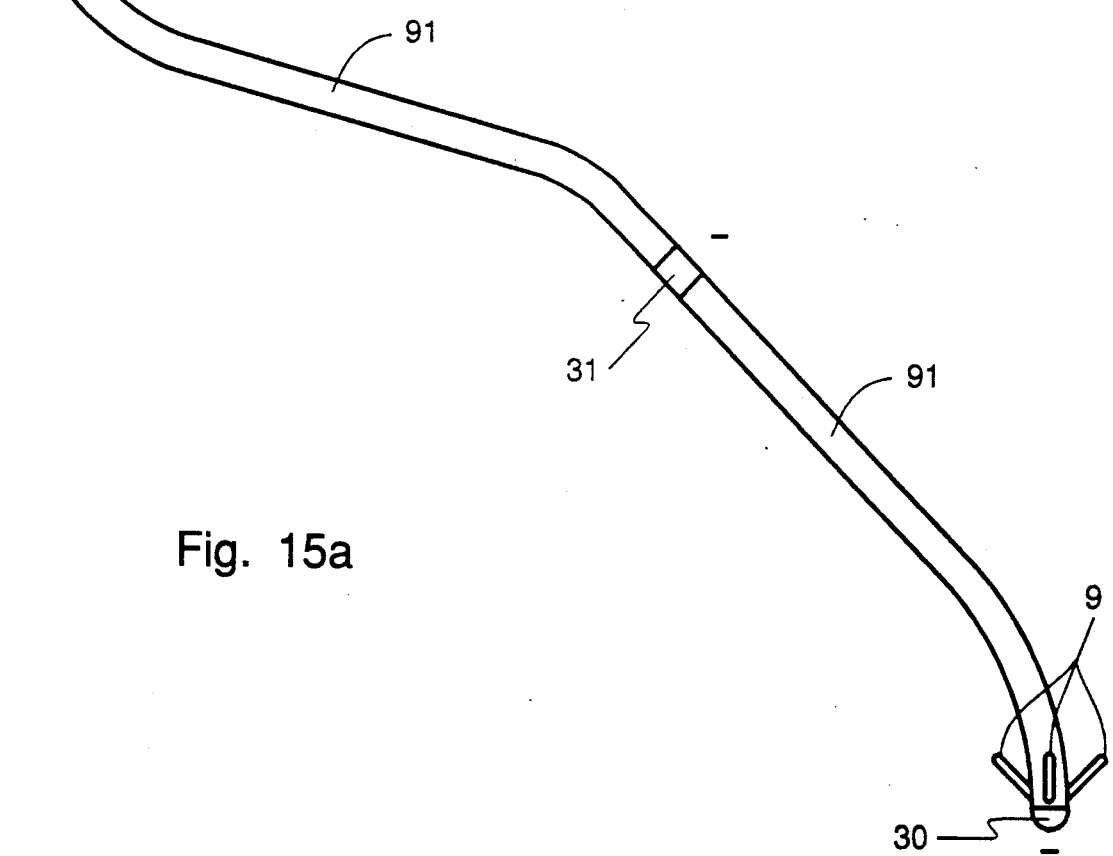
Fig. 15b
Fig. 15a

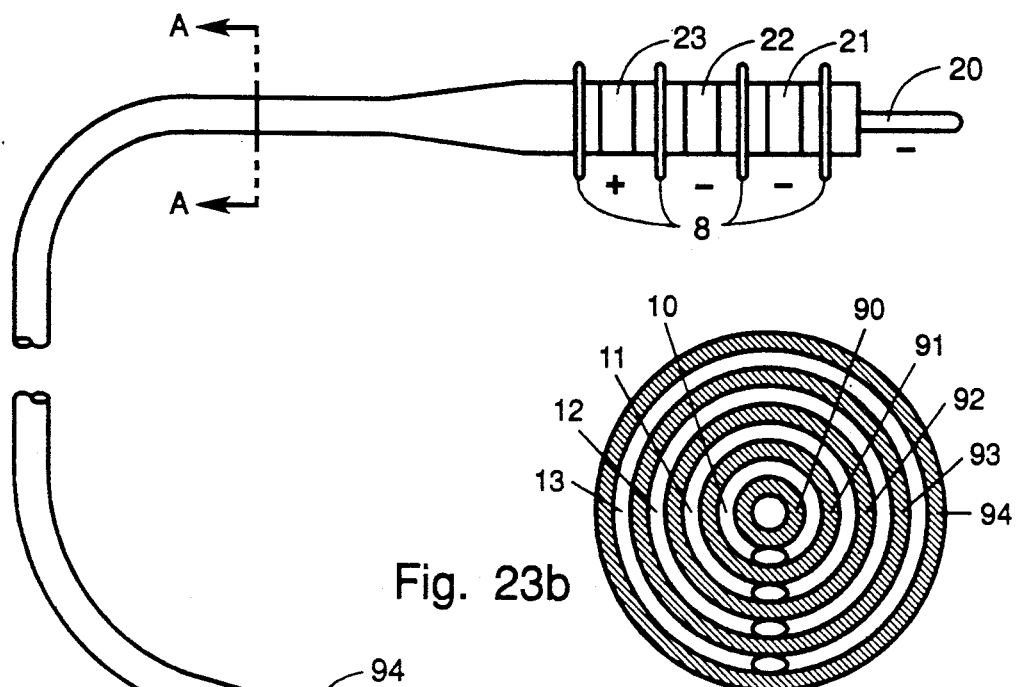
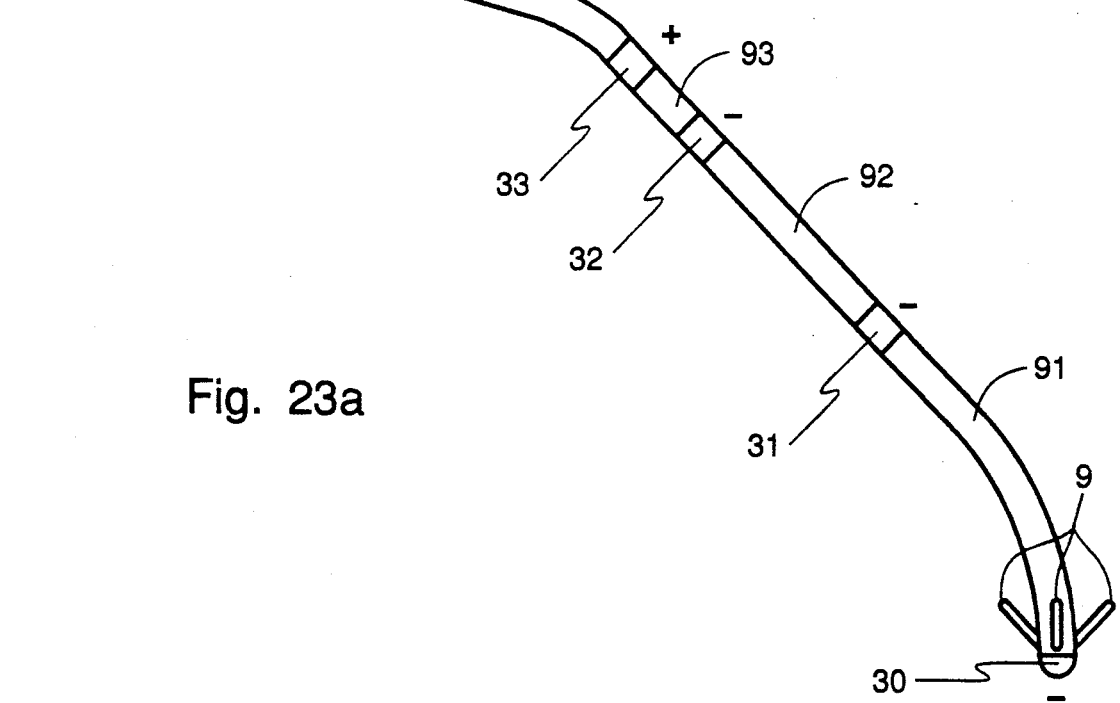
Fig. 23b
Fig. 23a

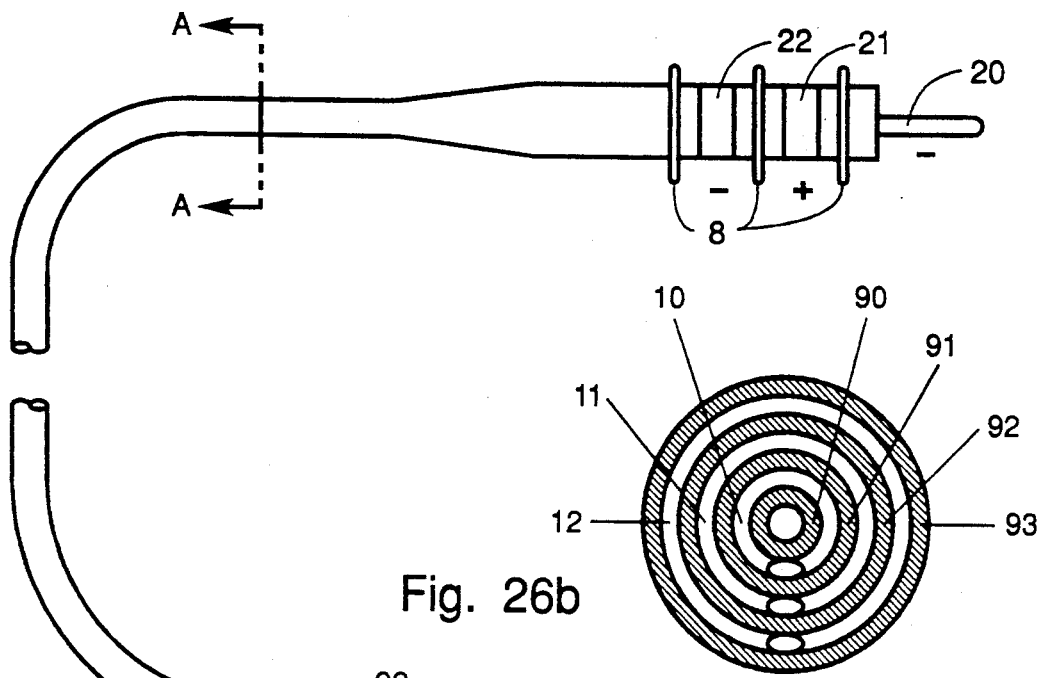
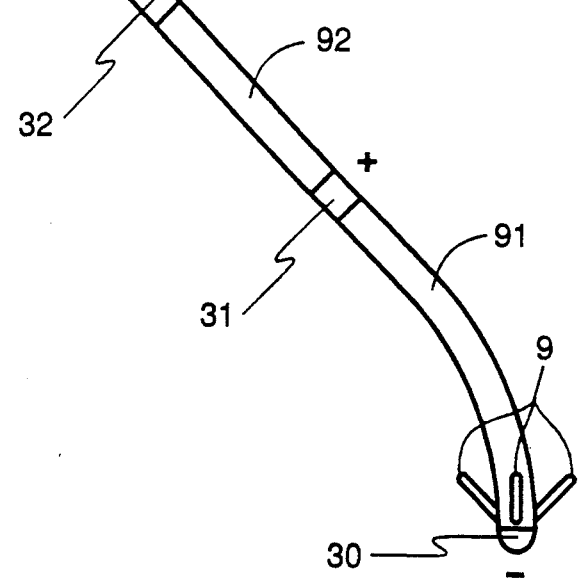
Fig. 26b
Fig. 26a 30A,31A,32A,33A,80A,81A,82A

PACING SYSTEMS AND METHODS FOR CONTROL OF THE VENTRICULAR ACTIVATION SEQUENCE

BACKGROUND OF THE INVENTION

1. Field of the Invention

This invention relates generally to medicine and more specifically to improved cardiac pacing systems including methods of pacing and sensing in the treatment of patients with cardiac disease.

2. Description of the Prior Art

Artificial cardiac pacemakers are electrical devices employed to electrically stimulate the heart in the absence of intrinsic cardiac electrical activity. They are currently used to treat a wide range of cardiac arrhythmias and are either implanted or used temporarily in the care of over 300,000 patients annually worldwide. Their ability to maintain life in the treatment of various arrhythmias when operating reliably is widely recognized.

Recent progress in pacemaker design has addressed improving the quality of recipients, lives with the advent of new pacing modes. Modern pacemakers may pace and sense in one or both chambers (atrial and ventricular) of the heart and may deliver electrical stimuli to the heart's chambers in the absence of intrinsic activity above a preset, atrial tracking or sensor indicated rate according to various pacing modes. These modern pacing modes are employed to produce atrio-ventricular (A-V) synchrony and/or rate increases based on various sensor inputs with the intention of increasing the exercise tolerance of pacemaker recipients and, increasing the cardiac output of pacemaker recipients during various additional physiologic states. There is debate surrounding the choice of an appropriate pacing mode for an individual patient due to the fact that rate increases are not tolerated by certain patients and are not beneficial to others. The development of atrial arrhythmias, the technical difficulties of placing an atrial lead, and the poor long term performance of certain atrial leads discourage certain doctors from dual chamber use.

An important similarity exists in all current pacemaker systems regardless of the available modes they employ. Current pacemaker systems stimulate and sense individual cardiac chambers through single pacing and sensing foci that may operate through bipolar or unipolar electrical pathways depending upon certain programmed parameters. These single focus pacemakers will be termed conventional pacemakers for the purpose of the analysis hereinafter described. Conventional pacemakers produce major differences in electrocardiographic recordings during pacing when compared to normal sinus rhythm.

An electrocardiogram or EKG is a recording of the electrical activity of the heart obtained from electrodes placed on the skin surface of a patient at various locations. An EKG recording from lead II displays this activity as recorded from electrodes placed on the right arm and left leg of a patient. FIG. 1a illustrates a normal sinus rhythm lead II EKG with a conventional ventricular paced lead II EKG shown in FIG. 1b, both shown with the same time scale and identical ventricular rates in the same patient under identical physiologic conditions other than pacing. A normal EKG generally consists of six major deflections or waves which are referred to as P, Q, R, S, T and U waves. When an individual heart muscle cell is activated, or fired, initiating its contraction, it gives off a characteristic electrical signal which is termed an action potential. Depolarization or activation is defined as the excursion of the action potential from the resting potential of the cell and repolarization is defined as the return of the action potential to the resting potential of the cell. Therefore a P wave describes the electrical activity of the atrial muscle cells as they depolarize, the QRS complex describes the electrical activity of the ventricular muscle cells as they depolarize (or activate) and the T wave describes the electrical activity of the ventricular muscle cells as they repolarize, as recorded from surface electrodes. U waves are not important for this analysis and are not shown or discussed for this reason.

In FIG. 1b the vertical line that begins the conventionally paced QRS complex represents a pacemaker spike which is an electrical impulse that initiates ventricular depolarization. Ventricular depolarization and then ventricular repolarization follow and will be referred to as a conventionally paced QRS complex and conventionally paced T wave respectively. As shown in FIGS. 1a and 1b, conventionally paced QRS complexes generally produce an opposite direction of deflection as compared to a normal QRS when recorded from lead II. P waves are not shown in the paced EKG due to the fact that they may or may not be present, or may be present in synchrony with the paced ventricular complex depending upon the pacing mode employed and the patient's intrinsic atrial rhythm.

Normal EKG morphologies and durations are variable from patient to patient and may vary significantly from normal in the presence of heart disease. FIGS. 1a and 1b represent EKG morphologies which are illustrative of commonly encountered recordings as supported by the literature. The analysis hereinafter described deals with the comparison of interval durations that are important to ventricular function and provides valid comparisons between paced and intrinsic ventricular complexes regardless of the exact EKG morphology recorded from an individual patient. These comparisons are also supported by the literature.

The following comparisons of interval durations will be made using a hypothetical patient whose chosen normal sinus and conventionally paced EKGs are illustrated in FIGS. 1a and 1b respectively. Therefore all firing times and durations noted will be referred to as distinctly describing this particular patient, with the realization that these durations may vary from patient to patient. Examples of durations obtainable by ventricular sequential pacing will be made in the same patient and incorporate specific assumptions producing durations that will similarly be referred to as distinctly describing this particular patient, with the realization that these durations may vary from patient to patient.

FIGS. 1a and 1b illustrate three major differences between normal sinus rhythm and conventional ventricular paced EKG morphologies. The Q-T interval, defined as the interval from the initiation of the Q wave to the termination of the T wave, is substantially shorter in normal sinus rhythm as shown in FIG. 1a than in a conventionally paced rhythm as depicted by a commonly encountered Q-Tns (normal sinus) of 250 msec compared to a Q-Tcp (conventionally paced) of 350 msec as shown in FIG. 1b. Secondly, the ST segment, defined as the interval from the end of the S wave to the beginning of the T wave, a period of normally little electrical activity, is evident in the normal EKG but not in the conventionally paced EKG. The ST segment is a valuable tool for cardiologists in the diagnosis of ischemic heart disease. Thirdly, the duration of the QRS complex, defined from the initiation of the Q wave to the termination of the S wave, representing ventricular depolarization, is shorter in a normal EKG as depicted by a QRSns of 50 msec compared to a QRScp of 150 msec in a conventionally paced EKG.

Therefore;

$$(Q\text{-}Tcp)-(Q\text{-}Tns)=(QRScp)-(QRSns)=100 \text{ msec}$$

where ns=normal sinus and cp=conventionally paced.

Systole is defined as the period of time that the ventricles are contracting. Electromechanical systole is defined as the period from initial electrical activation of ventricular muscle to the end of contraction which, closely approximates the Q-T interval. Electromechanical systole will hereinafter be referred to as systole or the systolic interval and systole will be considered equal to the Q-T interval. Diastole or the diastolic interval is defined as the period of time that the ventricles relax and for the purposes of the following analysis is the period of time when the ventricles are not in systole. The RI (rate interval) shown in FIGS. 1a and 1b is 500 msec which is equivalent to a ventricular rate of 120 beats per minute. It should be understood that the principles of the hereinafter analysis will apply at any other rate chosen.

The percentage of time that the ventricles contract or percent systole is defined as the ratio of Q-Tns to RI in normal sinus rhythm and Q-Tcp to RI in a conventionally paced rhythm.

Therefore;

$$\% \text{ SYSTOLEns} = (Q\text{-}Tns)/RI = 250 \text{ msec}/500 \text{ msec} = 50\%$$
$$\% \text{ SYSTOLEcp} = (Q\text{-}Tcp)/RI = 350 \text{ msec}/500 \text{ msec} = 70\%$$

The percentage of time that the ventricles relax is defined as percent diastole as shown below:

$$\% \text{ DIASTOLEns} = 100\% - \% \text{ SYSTOLEns} = 100\% - 50\% = 50\%$$
$$\% \text{ DIASTOLEcp} = 100\% - \% \text{ SYSTOLEcp} = 100\% - 70\% = 30\%$$

Percent systole is an extremely important determinant of ventricular function. The lower the percent systole the more forceful a ventricular contraction is produced due to the fact that the ventricular muscle fibers contract to produce a more rapid ejection of blood from the heart as compared to higher percent systoles. This is referred to in the art as an element of increased ventricular contractility. Thus, as percentage systole decreases, increases in the efficiency of ventricular contraction, stroke volume and ejection fraction are realized. Lowering the percent systole also decreases the duration of time during which pressure is applied to the coronary arteries. Greater percent systoles produce local intramural forces of contraction around the coronary arteries that are applied over a longer period of time, accordingly decreasing coronary perfusion during exercise and in the resting state.

As seen in the above formulas, as percent systole increases, percent diastole decreases. The great majority of exercise related coronary blood flow increase occurs during diastole. Accordingly, decreases in percent diastole produce significant decreases in coronary blood flow during exercise and significant but less dramatic decreases in coronary blood flow in the resting state. The time available for ventricular filling is equal to the diastolic interval. Ventricular filling time is increased with increased percent diastoles, accordingly increasing cardiac output by increasing stroke volume and ventricular preload. Electrically, the longer the Q-T interval the greater the ventricular muscle's vulnerable period during repolarization and the more likely it becomes for a patient to develop further arrhythmias.

Q-T interval is therefore an extremely important determinant of ventricular function during exercise as well as in the resting state. Conventional pacemakers produce significant Q-T interval prolongation with consequent decreases in ventricular contractility, cardiac output, coronary blood flow and electrical stability of the ventricular muscle. A pacemaker system that provides the ability to shorten the Q-T interval during pacing would significantly improve the ventricular function of pacemaker recipients. These improvements would be applicable to all current and future pacing modes employed and would improve the quality of life of pacemaker recipients in the resting state, during exercise and under various additional physiologic circumstances.

SUMMARY OF THE INVENTION

One object of the present invention is to provide improved cardiac pacing systems.

Another object of the present invention is to provide a cardiac pacing system that increases cardiac output during various physiologic states of activity.

Still another object of the present invention is to provide a cardiac pacing system that increases coronary artery perfusion during various physiologic states of activity.

It is yet another object of the present invention to provide a cardiac pacing system that increases ventricular stroke volume during various physiologic states of activity.

Yet another object of the present invention is to provide a cardiac pacing system that increases the ventricular ejection fraction during various physiologic states of activity.

Another object of the present invention is to provide a visible ST segment, as recorded from an EKG during ventricular pacing.

It is a further object of the invention to provide a pacemaker system which has the capability of improving ventricular function both in the duration of its contraction and the control of ventricular wall and septal motion.

It is yet a further object of the present invention to provide a cardiac pacing system with the capability of bypassing the electrical obstruction of infarcted myocardium or otherwise diseased cardiac muscle.

Another object of the present invention is to provide a cardiac pacing system that will be of value in the treatment of various degrees of right or left bundle branch block by shortening the activation sequence of the abnormally contracting wall to more closely approximate that of the normally contracting wall.

It is yet another object of the present invention to provide a cardiac pacing system that has the capability of shortening wide QRS complexes of intrinsic origin.

A further object of the present invention is to provide a cardiac pacing system with the capability of compensating for changes in cardiac size to produce the shortest Q-T interval obtainable and/or most desirable ventricular wall motion under conditions of varying ventricular size.

Yet another object of the present invention is to provide a cardiac pacemaker system with greater reliability during pacing and sensing than those of the prior art.

It is yet a further object of the present invention to provide a cardiac pacing system that has the capability of selecting a desirable pacing focus or groups of foci with non-invasive programmable circuitry, independent of the sensing focus or foci selected.

It is another object of the present invention to provide a cardiac pacing system that has the capability of selecting a desirable sensing focus or groups of foci with non-invasive programmable circuitry, independent of the pacing focus or foci selected.

Another object of the present invention is to provide a cardiac pacing system which improves ventricular function and output on demand as indicated by a sensor signal or atrial tracking rate.

It is yet another object of the present invention to provide a cardiac pacing system with reduced power consumption as compared to those of the prior art.

Still another object of the present invention is to provide a cardiac pacing system that can be implanted in an atraumatic manner.

Another object of the present invention is to provide a cardiac pacing system that facilitates the placement of certain pacing and sensing foci at the ventricular septum and/or the ventricular walls.

It is yet another object of the present invention to provide a cardiac pacing system that incorporates a ground electrode location or locations which are safer and more reliable than those of the prior art.

According to the present invention one or more pacing and sensing foci are arranged within the ventricle and are selected to pace at specific points, either simultaneously or in a programmed sequence, in order to produce a desired ventricular response which increases cardiac output and coronary perfusion as compared to the prior art.

A cardiac pacing system in accordance with the present invention provides the ability to shorten the ventricular contraction sequence and modify the sequence of ventricular contraction in a manner which can be preselected or triggered by sensor outputs, and individually tailored for each specific pacemaker recipient.

Reference is hereby made of my previous illustrated description entitled "Ventricular Sequential Pacemaker Systems" which was filed under The Disclosure Document Program on July 31, 1989 and assigned Disclosure Document No. 231886, which is incorporated by reference herein.

Reference is also hereby made to my previous written and illustrated description entitled "Ventricular Sequential Cardiac Pacemakers" which was filed under The Disclosure Document Program on Feb. 8, 1990 and assigned Disclosure Document No. 245061, which is incorporated by reference herein.

The foregoing and other objects, features and advantages of the invention will be apparent from the following, more particular description of the preferred embodiment of the invention, as illustrated in the accompanying drawings.

BRIEF DESCRIPTION OF THE DRAWINGS

FIGS. 1a and 1b illustrate an electrocardiographic comparison of normal sinus rhythm and conventional ventricular pacing;

FIG. 6a illustrates the action potential distribution of a single focus ventricular sequentially paced ventricular activation sequence where the pacing electrode is placed at a mid-septal position; FIG. 6b illustrates an electrocardiogram of a single focus ventricular sequentially paced ventricular activation sequence where the pacing electrode is placed at a mid-septal position; and FIG. 6c illustrates the sequence of cell firing within a ventricular cross section of a single focus ventricular sequentially paced ventricular activation sequence, where the pacing electrode is placed at a mid-septal position;

FIG. 15a is a front view showing a twin focus single wire pacing lead for use with the circuitry shown in FIGS. 13 and 14; FIG. 15b is a section through such pacing lead;

FIG. 23a is a front view showing a three focus, four wire pacing lead for use with the circuitry shown in FIGS. 20, 21 and 22; FIG. 23b is a section through said pacing lead;

FIG. 26a is a front view showing a two focus, three wire pacing lead with symmetrical bipolar electrical pathways, for ventricular sequential pacing; FIG. 26b is a section through said lead;

DESCRIPTION OF THE PREFERRED EMBODIMENTS

Ventricular sequential pacing systems of this invention will provide novel methods and devices to shorten the activation sequence of the ventricular chambers in order to produce shortening of the Q-T interval as compared to conventional pacemakers. As used herein, the expression ventricular sequential pacing means alteration of the sequence of ventricular activation, or an alteration of the duration of the sequence of ventricular activation as well as a selection of advantageous sequences for individual patients with specific cardiac diseases. It is therefore essential to the understanding of this novel concept that the ventricular activation sequence and ventricular anatomy be defined in the necessary detail.

Figure 2A:
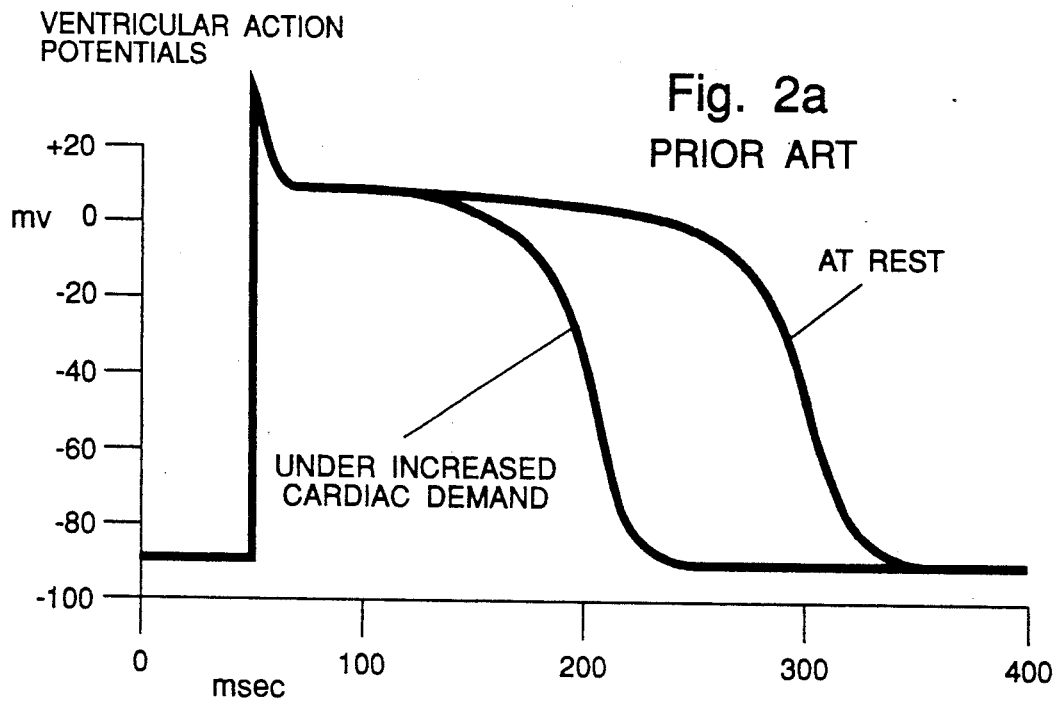
FIG. 2a is a graph of a range of ventricular muscle cell action potentials and FIG. 2b is a cross section of a heart showing right and left ventricles with commonly used anatomic terms.
Figure 2B:
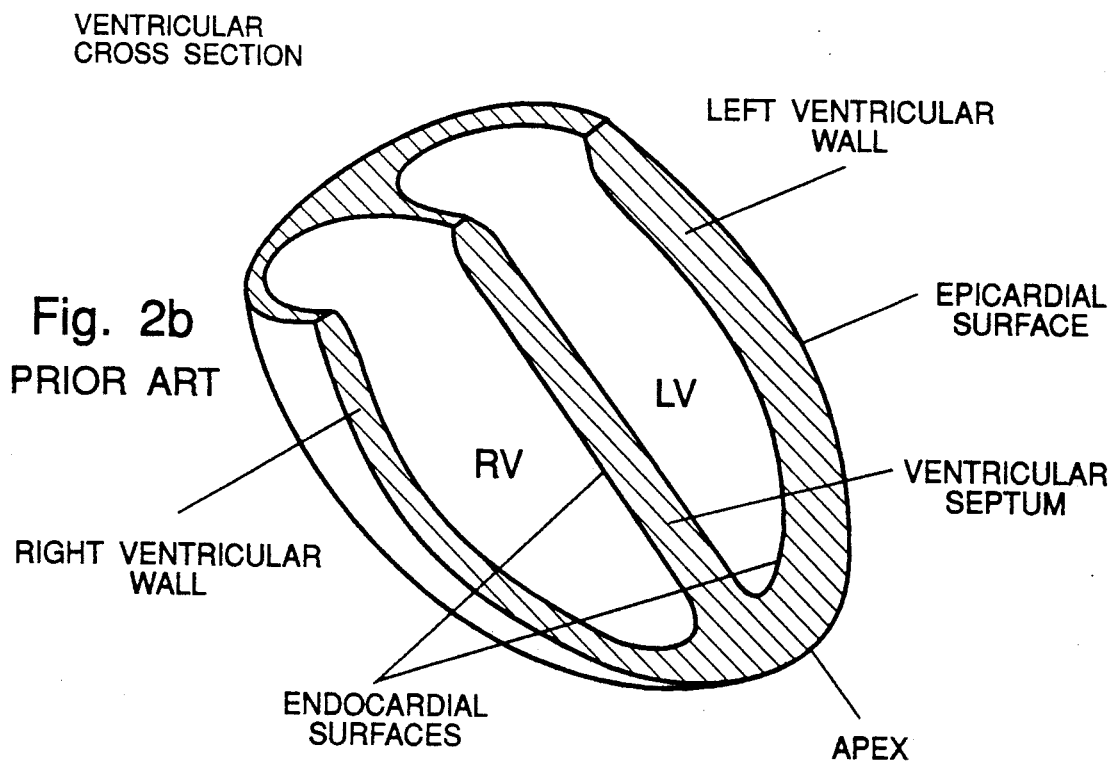

FIG. 2a illustrates a range of ventricular muscle cell action potentials operating from a resting potential of $-90$ mv. The length of an action potential normally shortens in the presence of increased circulating catecholamine levels and increased ventricular rate. This is the body's normal response to events requiring increased cardiac output and occurs whether the ventricle is activated in normal sinus rhythm or is paced. All comparisons in the hereinafter analysis will consider ventricular muscle cell action potentials of uniform 200 msec duration due to the fact that they will deal with patients in identical physiologic states at a fairly rapid heart rate of 120 beats per minute. This FIG. 2a is shown to demonstrate the validity of these comparisons at any uniform action potential duration provided that identical physiologic states other than pacing are compared in the same patient. FIG. 2b shows a cross sectional view of the ventricular chambers and certain common anatomical terms that will be useful in the understanding of the hereinafter analysis. RV represents the right ventricle and LV represents the left ventricle.

Figure 3A:
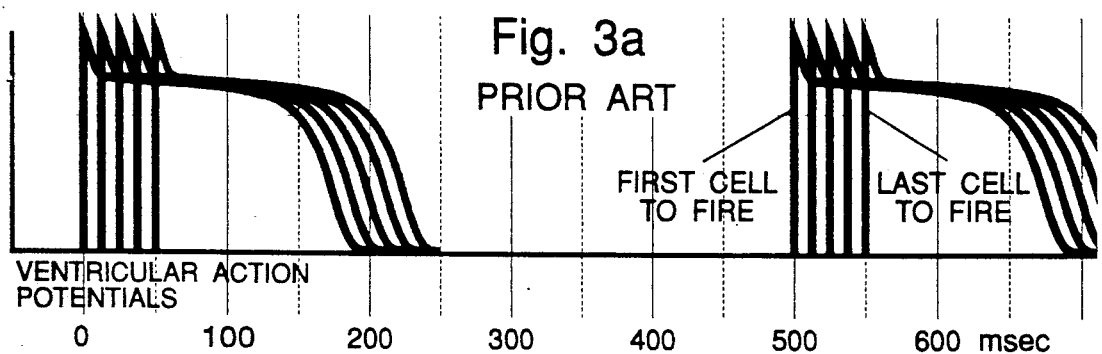
FIG. 3a illustrates the action potential distribution of a normal ventricular activation sequence.
Figure 3B:
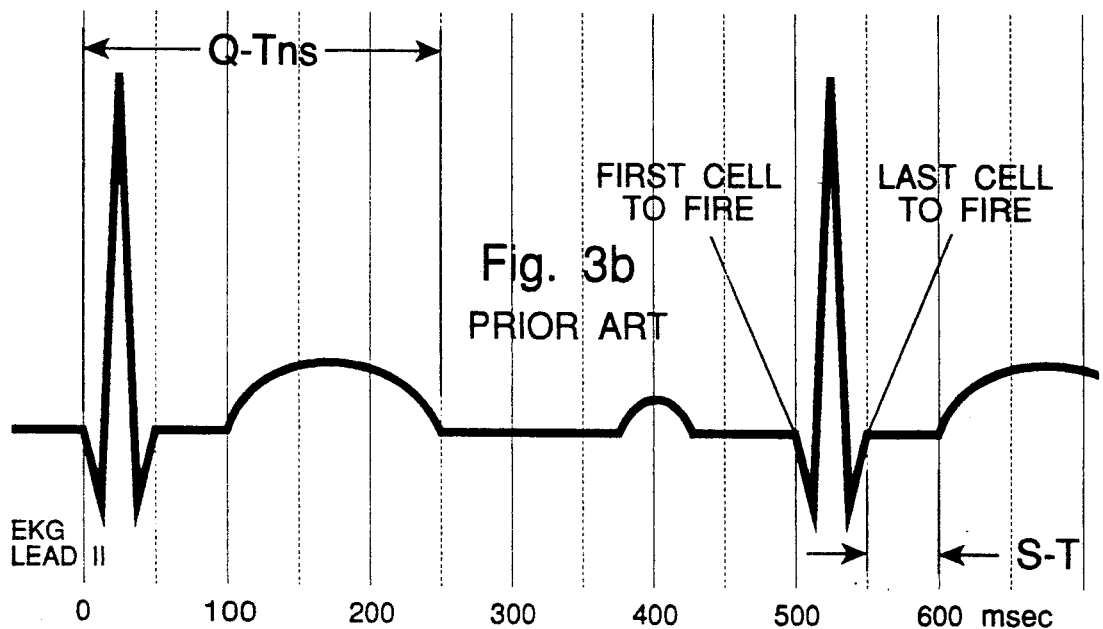
FIG. 3b illustrates an electrocardiogram of a normal ventricular activation sequence.

FIG. 3a illustrates normal ventricular action potential activation; FIG. 3b illustrates a normal sinus rhythm lead II EKG; and, FIG. 3c the normal activation sequence of the ventricles. In FIG. 3a a representation of the normal conduction system is shown within the ventricular muscle cross section, which conduction system has two very important purposes in achieving normal ventricular function. The conduction system conducts electrical impulses at velocities over three times faster than conduction occurring via a cell to cell route. Exact actual conduction velocity measurements are extremely difficult in a viable beating heart. EKG analysis, supported by the literature, confirms that the QRScp complex occurring via cell to cell conduction during conventional pacing is approximately three times the duration of a QRSns complex during normal sinus rhythm where the majority of conduction occurs via the conduction system. This fact is illustrated in FIGS. 1a and 1b showing that a QRScp is equal to three times QRSns. Secondly the normal conduction system produces a sequence of activation that initially activates the septum, then the apex and thereafter travels along the ventricular walls in the order illustrated in FIG. 3c by the ventricular cell firing times noted. This normal sequence of activation is believed to produce an efficient ventricular contraction by controlling the ventricular muscle cells in this manner which ejects blood from the ventricles by beginning ventricular wall contraction at the apex and ending contraction high on the ventricular walls thus also minimizing areas of blood flow stagnation that are important in the prevention of thrombosis and thromboembolic episodes.

The ventricular action potentials shown in FIG. 3a are illustrative of their important relationship to the Q-Tns interval. Ventricular action potentials that are labeled first cell to fire or activate and last cell to fire, along with their occurrences on the lead II EKG, can be seen to determine the length of the QRSns complex. Other action potentials shown in between the first and last cells to fire are representative of other cells firing in between and are shown at equal intervals in order to describe the period of time during which ventricular cells are activating (depolarizing) and repolarizing, and as a representation of the density of ventricular activation and repolarization. The following examples will refer to distinct first and last cell firing times with the realization that these cells may, depending upon individual cardiac anatomy, be included in a group of cells which fire at identical times. The terms "first cell to fire" and "last cell to fire" are used for illustrative purposes in describing interval durations. Q-Tns interval in a normal heart is therefore equal to the interval beginning with the first cell to fire and ending with the return to resting potential of the last cell to fire. There are therefore, two major determinants of the Q-Tns interval which are the duration described from the first cell to fire to last cell firing and the action potential duration of the last cell to fire.

Late potentials, as recorded by high resolution or signal averaged EKGs, may occur within 40 msec after the QRS complex when the QRS complex is generally greater than 120 msec and the patient has no gross evidence of conduction system disease. These late potentials have been studied in patients who have survived a myocardial infarction and are considered by some to be an indication of forthcoming life threatening arrhythmias. As will be seen, shortening of the QRS complex by ventricular sequential pacing and/or placement of electrodes in order to bypass the electrical obstruction of myocardial infarctions, may constitute a form of treatment for patients in whom late potentials have been detected.

It should be noted that this action potential sequence is based upon the characteristics of normal healthy ventricular muscle cells where all ventricular muscle cell action potentials are approximately equal in duration. Certain types of heart disease may cause prolongation of certain ventricular action potentials but not others. Thus, there are certain situations where the last cell to fire may not be the last cell to return to its resting potential. The hereinafter analysis will concern itself with equal action potential durations as seen in a heart with normal ventricular muscle which requires pacing for diseases that do not produce an action potential duration distribution.

Figure 3C:
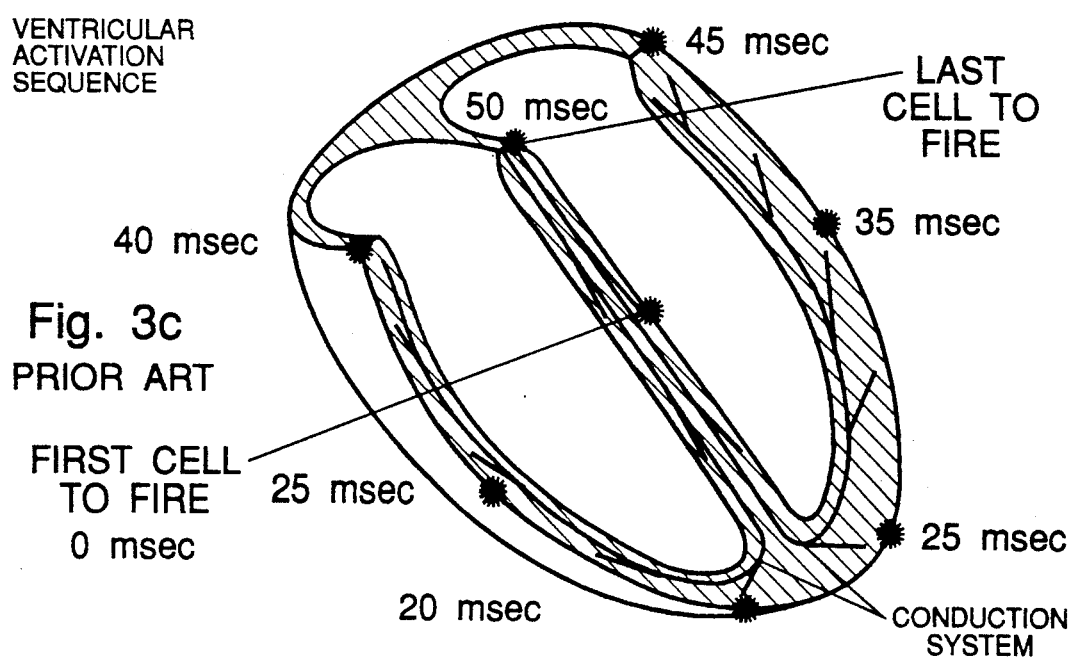
FIG. 3c illustrates the sequence of cell firing within a ventricular cross section of a normal ventricular activation sequence.
Figure 4A:
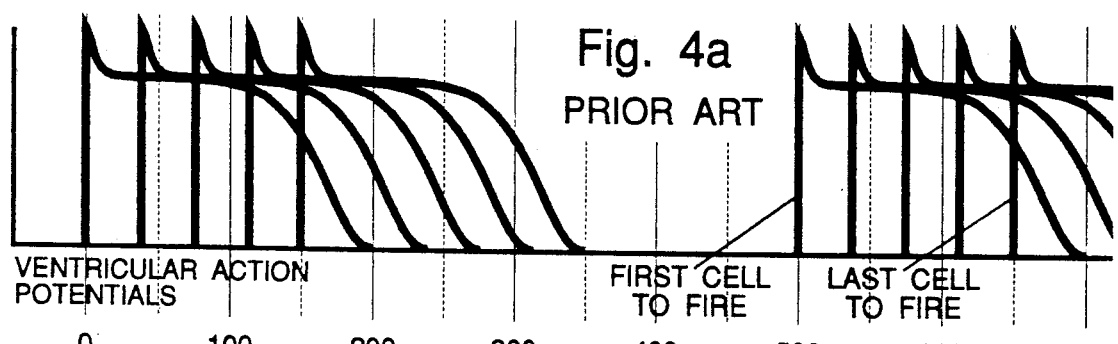
FIG. 4a illustrates the action potential distribution of a conventionally paced ventricular activation sequence where the pacing electrode is placed at the right ventricular apex.
Figure 4B:
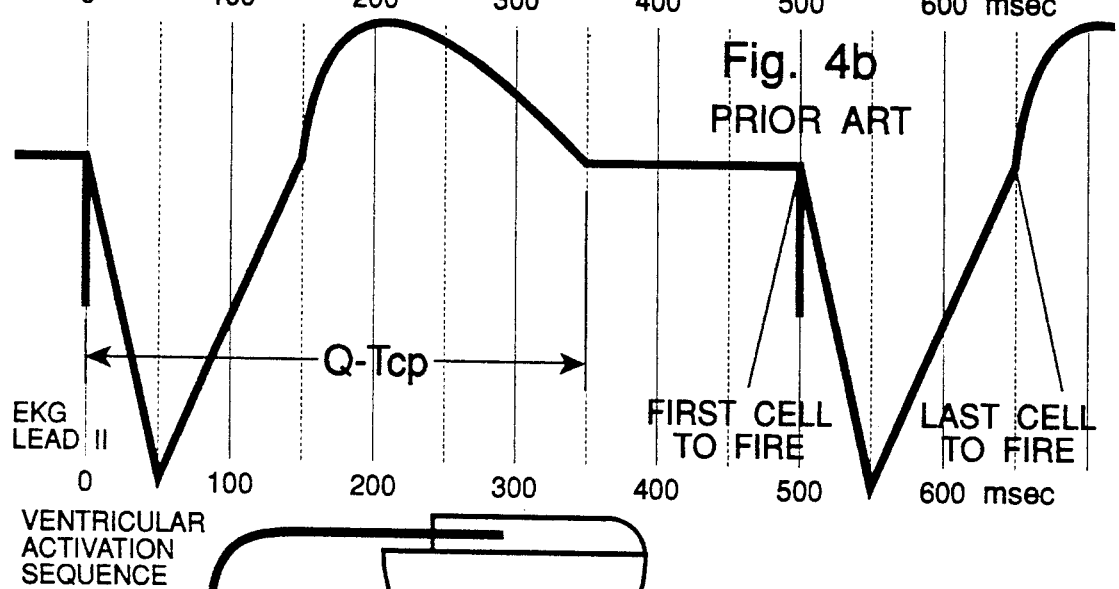
FIG. 4b illustrates an electrocardiogram of a conventionally paced ventricular activation sequence where the pacing electrode is placed at the right ventricular apex.
Figure 4C:
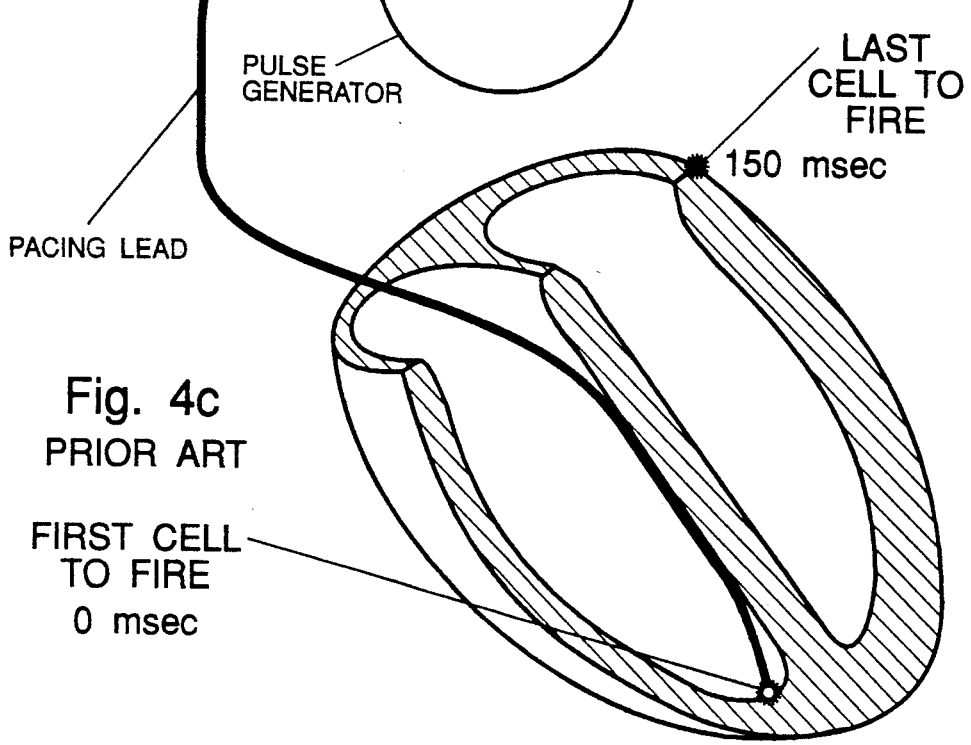
FIG. 4c illustrates the sequence of cell firing within a ventricular cross section of a conventionally paced ventricular activation sequence where the pacing electrode is placed at one right ventricular apex.

FIGS. 4a-4c illustrate how conventional pacing alters the ventricular action potential firing density and activation sequence in the same format as FIGS. 3a-3c. The ventricular conduction system in this case being not functional is not shown. A conventional pulse generator and pacing lead (pacing wire) are shown which initiate activation at least one cell in the right ventricular apex. Activation is then conducted by cell to cell conduction with the last cell firing 150 msec later.

It is important to note that placement of the stimulating electrode of a conventional pacing lead as shown in FIG. 4c, is generally and preferably at the right ventricular apex for two important reasons. Firstly, such placement results in depolarization being initiated at the apex which produces a more normal, though generally longer, activation sequence than at any other point in the right ventricle having benefits hereinbefore stated. Secondly, conventional ventricular pacing leads are more stable in the right ventricular apex than at other points in the right ventricle due to the greater density of trabeculae that normally occur in the apical area and serve to better secure the lead tip.

It should also be understood that the great majority of pacemakers that are currently implanted, or used temporarily, employ the relatively atraumatic and widely accepted procedure of introducing the pacing lead through a vein and threading it to the right ventricle where it is positioned to obtain the best electrical pacing threshold and sensing signal, generally with its tip in the right ventricular apex. It is an important advantage of the hereinafter defined ventricular sequential pacemakers that they can be implanted using the identical procedure. When using this procedure many of the conventional pacemaker leads inserted will appear as shown in FIG. 3c with a portion of their length in contact, with the ventricular septum.

There is significant biologic variation in the size and shape of the normal ventricular muscle chambers from patient to patient. Heart disease in many instances will cause significant variation from normal in the size and shape of the chambers. The ventricular sequential pacing as described herein will produce Q-T interval shortening when compared to conventional pacing regardless of the ventricular dimensions considered due to the fact that electrodes are placed electrically closer to the last cells to fire than can be accomplished by conventional pacing. The ventricular shape portrayed in FIGS. 2-12 is illustrative of the general shape of the ventricular muscle chambers, exclusive of the papillary muscles, and will be uniformly used for comparisons of conventional and ventricular sequential pacing in the same patient with uniform action potential durations.

Figure 5:
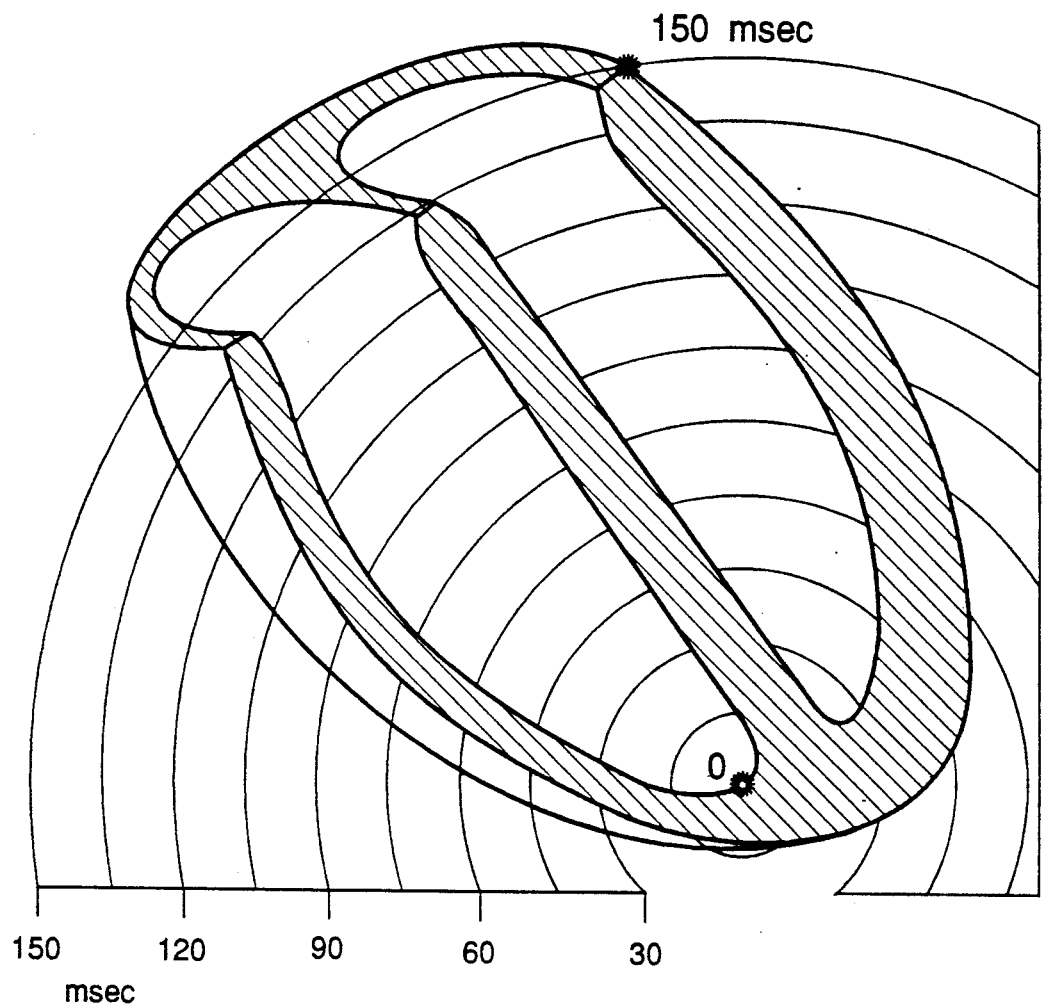
FIG. 5 illustrates the propagation of activation within a ventricular cross section during the conventional ventricular pacing method as previously illustrated in FIGS. 4a-4c.

FIG. 5 illustrates the propagation of ventricular activation during conventional pacing based upon the following premises. As noted hereinbefore with regard to normal sinus rhythm, actual conduction velocity measurements are extremely difficult in a viable beating heart during pacing. Therefore certain approximations will be made in order to illustrate the propagation of ventricular activation during conventional ventricular pacing and ventricular sequential pacing according to this invention. Actual Q-T interval reductions in patients will approximate these values to the extent the approximations are valid for an individual patient. The degree of Q-T interval shortening obtained is expected to be variable from patient to patient but certain degrees of Q-T shortening will be evident in virtually all patients paced with a ventricular sequential pacemaker as compared to a conventional pacemaker. Only certain theoretical exceptions exist, one of which can be demonstrated when a certain cell which fires at identical intervals in comparative examples has an action potential whose duration exceeds all others to the extent that it alone determines the end of the Q-T interval. This set of circumstances is believed to be possible but not commonly encountered due to the fact that action potential duration prolongation of this magnitude often signals the onset of potentially lethal arrhythmias. It is important to note that QRS shortening will result from ventricular sequential pacing regardless of whether the Q-T interval shortens or not.

Intracellular current has been described in the art, as travelling predominantly in a longitudinal direction along cardiac fibers and from one fiber to another predominantly by means of the intercalcated discs. Thus there is microscopic electrical propagation in a tortuous path that will not be considered in the macroscopic analysis which will follow. An approximation will be made that cell to cell ventricular conduction velocities are constant within an individual heart at a specified physiologic state. In the determination of ventricular propagation sequences it will be assumed that the shortest path of firing propagation between two cells will occur in a plane that includes the straight line which connects these cells in normal ventricular muscle. In the hereinafter described example of myocardial infarction it will be shown that this is not true in certain forms of heart disease. Since ventricular activation precedes ventricular contraction on a cell by cell basis, the effects of ventricular contraction on the propagation of activation will not be considered in the following analysis. The plane of propagation for the purposes of the hereinafter comparisons will be assumed to be perpendicular to the cross section of the ventricles and accordingly perpendicular to the plane of the figures. Straight lines will represent the radiation of cell to cell conduction in the following analysis. In reality the propagation of ventricular firing will traverse the hollow ventricular chambers by traveling around them in a cell to cell fashion. Thus, the foregoing approximations will produce a proportionality between actual cell by cell propagation and the straight lines assumed, by plotting actual observed conduction times along the lines when observed firing times are known, as in the case of the duration between first and last cell firing in FIGS. 4a-4c. Cells firing in between the first and last cells to fire will be assumed to fire at intervals proportional to their straight line distance from these cells using the known time to distance relationship. It should be noted that selection of the site of last cell firing is reasonable based upon the ventricular shape selected for these examples. Actual last cell firing sites will depend upon the actual anatomy involved. It should also be noted that the foregoing assumptions do not hold true when the path of cell to cell propagation does not traverse a hollow ventricular chamber. This however does not have a material effect in the determination of Q-T intervals. In FIG. 5, based on the foregoing premises, circles are constructed at 15 msec intervals to describe the propagation pattern of ventricular activation during conventional ventricular pacing.

Figure 7:
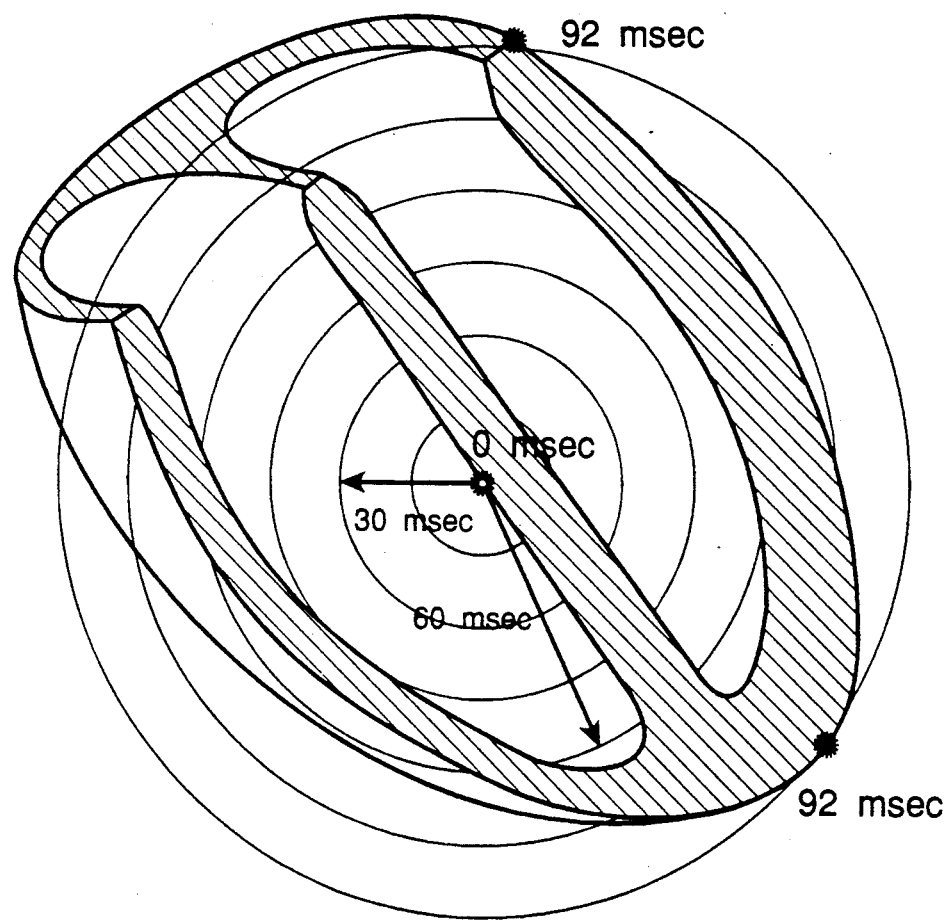
FIG. 7 illustrates the propagation of activation within a ventricular cross section during the single focus ventricular sequential pacing method as previously illustrated in FIGS. 6a-6c.
Figure 8:
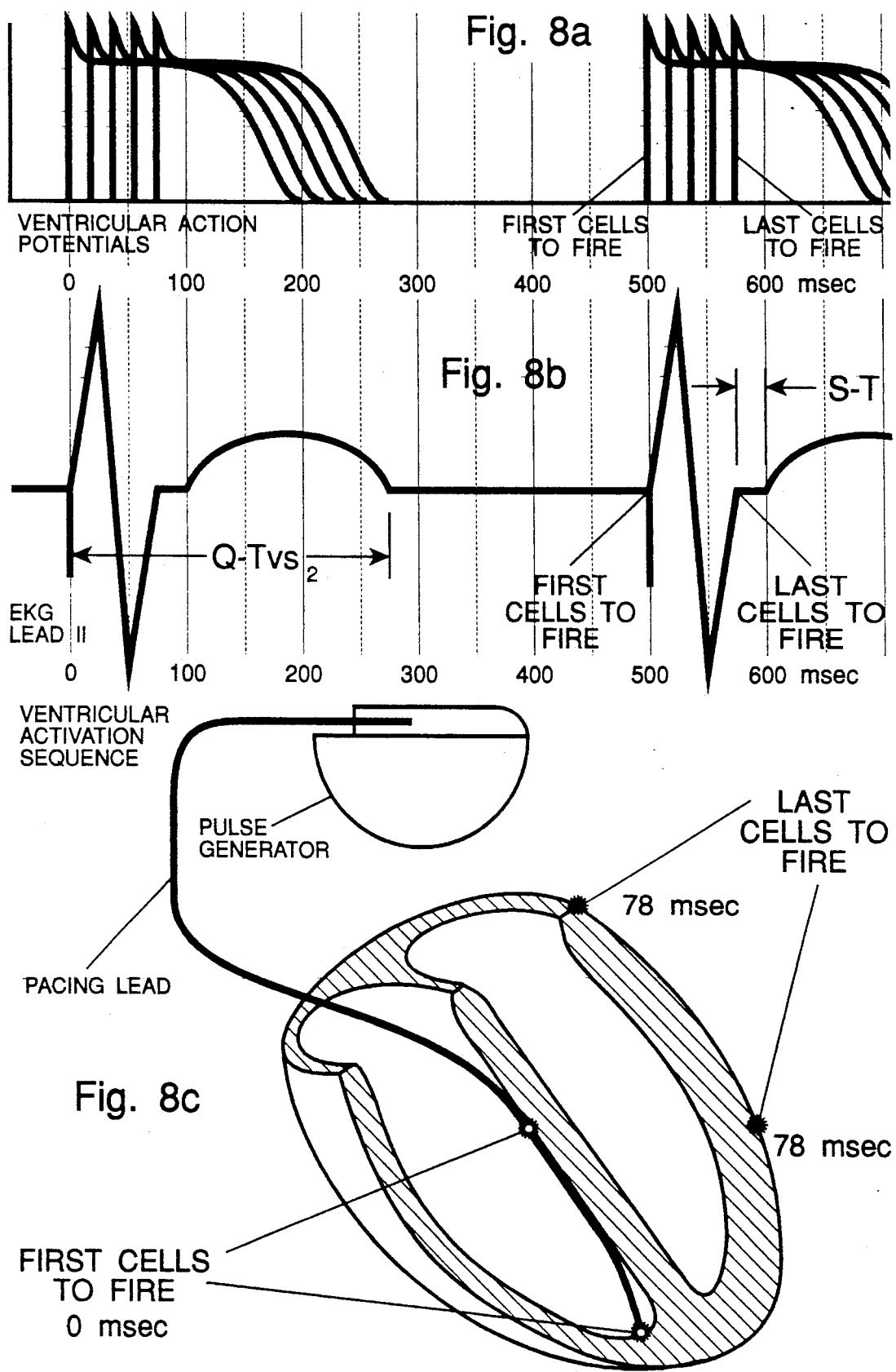
FIG. 8a illustrates the action potential distribution of a twin focus ventricular sequentially paced ventricular activation sequence where the pacing electrodes are placed at the right ventricular apex and mid-septal positions.
FIG. 8b illustrates an electrocardiogram of a twin focus ventricular sequentially paced ventricular activation sequence where the pacing electrodes are placed at the right ventricular apex and mid-septal position.
FIG. 8c illustrates the sequence of cell firing within a ventricular cross section of a twin focus ventricular sequentially paced ventricular activation sequence where the pacing electrodes are placed at the right ventricular apex and mid-septal positions.

FIGS. 6a–6c illustrate one form of ventricular sequential pacing with one pacing focus positioned in the mid-septal area at a point which is equidistant from the two last cells to fire. FIG. 7 illustrates the propagation pattern produced thereby which yields a ventricular activation sequence duration of 92 msec. As shown in FIG. 6b there is a Q-T$vs_1$ duration of 292 msec which is 58 msec less than the Q-Tcp of 350 msec as shown in FIG. 4b obtained under identical circumstances, other than the method of pacing. In the following analysis "vs" = ventricular sequential pacing and "cp" = conventional pacing.

Therefore;

% SYSTOLE$vs_1$ = (Q-T$vs_1$)/RI = 292 msec/500 msec = 58.4%

% SYSTOLEcp = (Q-Tcp)/RI = 350 msec/500 msec = 70.0% and;

% DIASTOLE$vs_1$ = 100% − 58.4% = 41.6%

% DIASTOLEcp = 100% − 70.0% = 30.0%

Accordingly, a significant decrease in percent systole of approximately 16 percent and increase in percent diastole of approximately 38 per cent will be achieved by single focus ventricular sequential pacing at a specific mid-septal point when compared to conventional pacing with an electrode at the right ventricular apex. There are, as have been stated hereinbefore, disadvantages in this type of approach due to the fact that the propagation of ventricular wall motion below the pacing electrode is not in a normal upward direction, and, placing a conventional lead (with its negative electrode at the tip) in a mid-septal location, whether using active fixation (screw in) or not, is less stable than apical placement. Also, determination during surgery of the specific point on the ventricular septum which produces the shortest Q-T interval may significantly lengthen the surgical procedure. This specific point on the septum may also change post-operatively with significant ventricular enlargement occurring as a result of progressing heart disease. The possible disadvantage of tip electrode placement in the mid-septal area may be reduced by employing the novel lead configuration shown in FIG. 6c. As shown, the end or tip of the lead rests at the ventricular apex as is conventional. However, the negative electrode is not at the end of the lead but is placed at a distance from the end of the lead so that it will contact the mid-septal area as shown in FIG. 6c.

Conventional pacemakers employ either a ground plate which is generally integral with the pacemaker case, referred to as a unipolar pacing system, or a ground electrode within the ventricle, referred to as a bipolar pacing system. It is known from intraoperative analysis of conventional bifurcated bipolar pacing electrodes that the proximal or originally intended positive electrode will generally have a satisfactory pacing threshold and sensing signal when tested as a single negative electrode in a unipolar configuration. These tests have been generally conducted during the period when the lead is termed chronic which is generally greater than 8 weeks post implant and is the period after which a sufficient endothelial tissue ingrowth has occurred in order to stabilize the electrode in the ventricle and threshold changes due to local acute tissue reactions have subsided. Leads that are termed chronic may still experience threshold changes resulting from myocardial infarction, excessive endothelial tissue ingrowth or other factors. It is the acute phase (before 8 weeks) of lead implantation during which the behavior of this negative mid-septal electrode position is unknown. The hereinafter description will introduce further novel methods for securing adequate acute thresholds in this mid-septal position. This single focus method of ventricular sequential pacing in the mid-septal area will be of value in certain patients where the advantage of shortening the Q-Tcp interval outweighs the disadvantage of a less than desirable ventricular wall motion below the electrode, where the mid-septal position is the only site available offering reasonable pacing thresholds, or where diaphragmatic stimulation occurs when pacing through an apical electrode.

FIGS. 8a–8c and 9 illustrate a further method of ventricular sequential pacing employing the simultaneous firing of two electrodes which produces a more desirable ventricular wall motion and a greater shortening of the $Q-T_{cp}$ interval than can be accomplished with the single focus configuration previously described and illustrated in FIGS. 6a–6c and 7. This twin focus pacing configuration includes a tip electrode and mid-septal electrode which in this example is placed as high on the lead as is practicable to achieve an adequate pacing threshold in the right ventricle. In this example the time between mid-septal electrode firing and the last cells to fire is equal to 78 msec which produces a $Q-T_{vs2}$ interval of 278 msec as compared to a Q-Tcp interval of 350 msec under identical circumstances other than the method of pacing.

Therefore;

% $SYSTOLE_{vs2}$ = $(Q-T_{vs2})/RI$ = 278 msec/500 msec = 55.6%

% $SYSTOLE_{cp}$ = $(Q-Tcp)/RI$ = 350 msec/500 msec = 70.0% and;

% $DIASTOLE_{vs2}$ = 100% − 55.6% = 44.4%

% $DIASTOLE_{cp}$ = 100% − 70% = 30.0%

Accordingly, a significant decrease in percent systole of approximately 20 percent and increase in percent diastole of approximately 48% will be achieved by twin focus ventricular sequential pacing when compared to conventional pacing as shown in FIGS. 4a–4c and 5. It should also be noted that twin focus ventricular sequential pacing produces a visible ST segment as illustrated in FIG. 8b as a result of the greater ventricular action potential activation density thus obtained as shown in FIG. 8a. This fact provides a valuable diagnostic tool to detect ischemia during twin focus ventricular sequential pacing which is not possible during conventional pacing. It should also be noted that twin focus ventricular sequential pacing provides redundant pacing foci which, as will be explained more fully hereinafter, can be employed with redundant pacing circuits and/or the programming ability to select or automatically switch pacing foci in the event one focus but not the other experiences exit block, thus significantly increasing pacemaker reliability from that existing with conventional pacemakers.

It is also important to note that while Q-T interval shortening produced by shortening ventricular action potential duration, either by natural or drug induced means, requires increased ventricular muscle oxygen consumption, shortening of the activation sequence does not, as comparisons of normal sinus rhythm and conventionally paced rhythm in individual patients have demonstrated.

It is important to note that prior experience with conventional pacemakers demonstrates the safety of activating the ventricle at more than one point within an interval of 150 msec from the initiation of ventricular activation. Fusion beats are defined as a pacemaker spike occurring during an intrinsic QRS complex and altering the morphology of the intrinsic QRS complex. It is widely accepted that fusion beats are of no harm to a patient other than the prolonged Q-T interval they may produce. Long experience with committed dual chamber pacing, ventricular sensing, inhibited pacemakers ("DVI" pacemakers) whose normal operation can deliver a pacemaker spike as much as 150 msec after an intrinsic QRS complex has produced no ill effects as demonstrated by the current U.S. Food and Drug Administration approval of this pacing mode.

Figure 9:
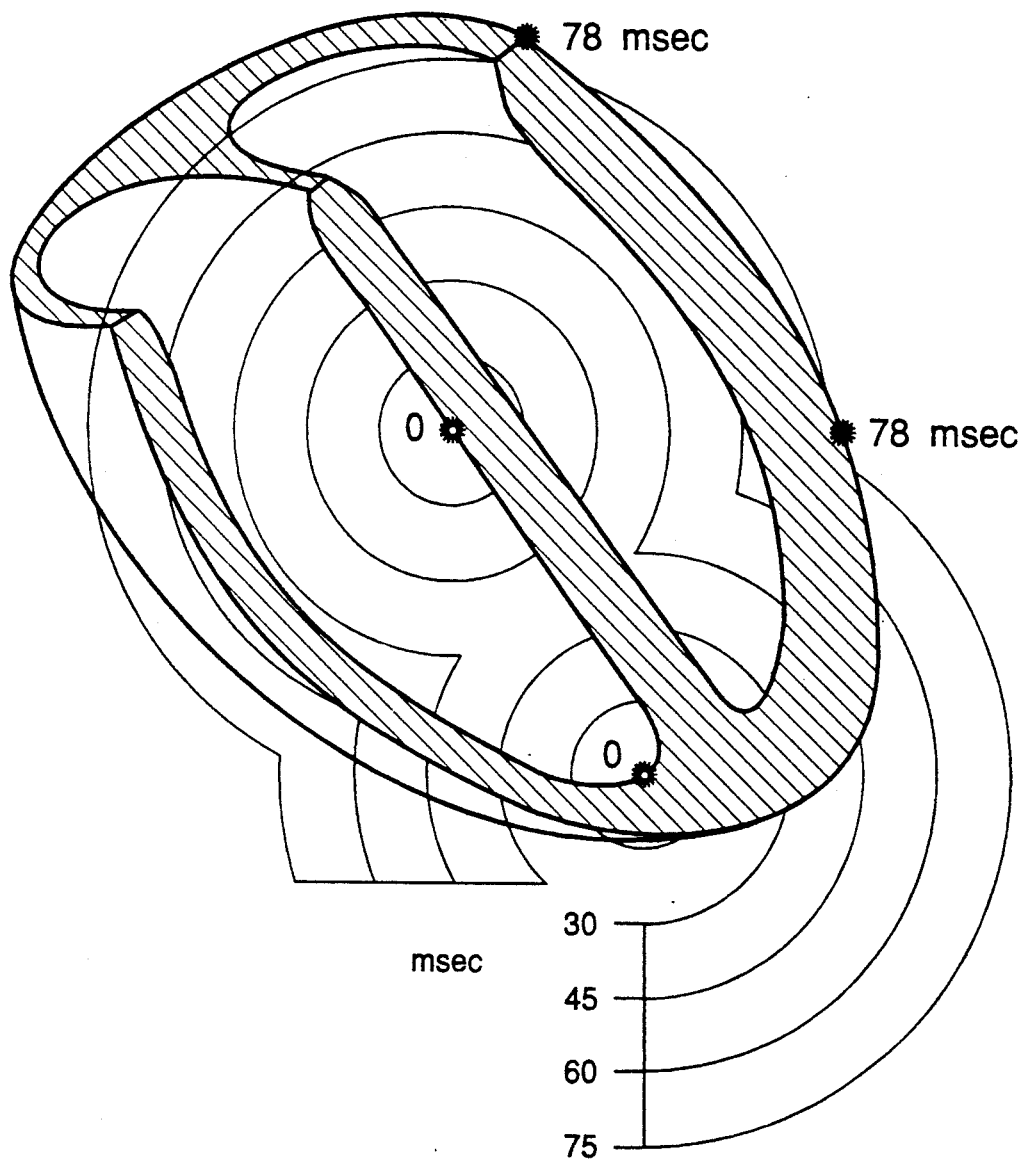
FIG. 9 illustrates the propagation of activation within a ventricular cross section during the twin focus ventricular sequential pacing method as previously illustrated in FIGS. 8a-8c.

Comparing FIGS. 7 and 9, it will be seen that there is a more desirable ventricular wall motion in the two focus system as shown in FIG. 9 than as shown in FIG. 7. Specifically, there is considerably less downward propagation of ventricular wall activation in FIG. 9 due to the fact that the apical area is activated much more quickly by the addition of the apical electrode.

The term "proximal" will be used to define the relative position of a pacing electrode as being closer along the lead to the pulse generator. The term "distal" will be used to define the relative position of a pacing electrode as being further along the lead from the pulse generator.

Figure 10:
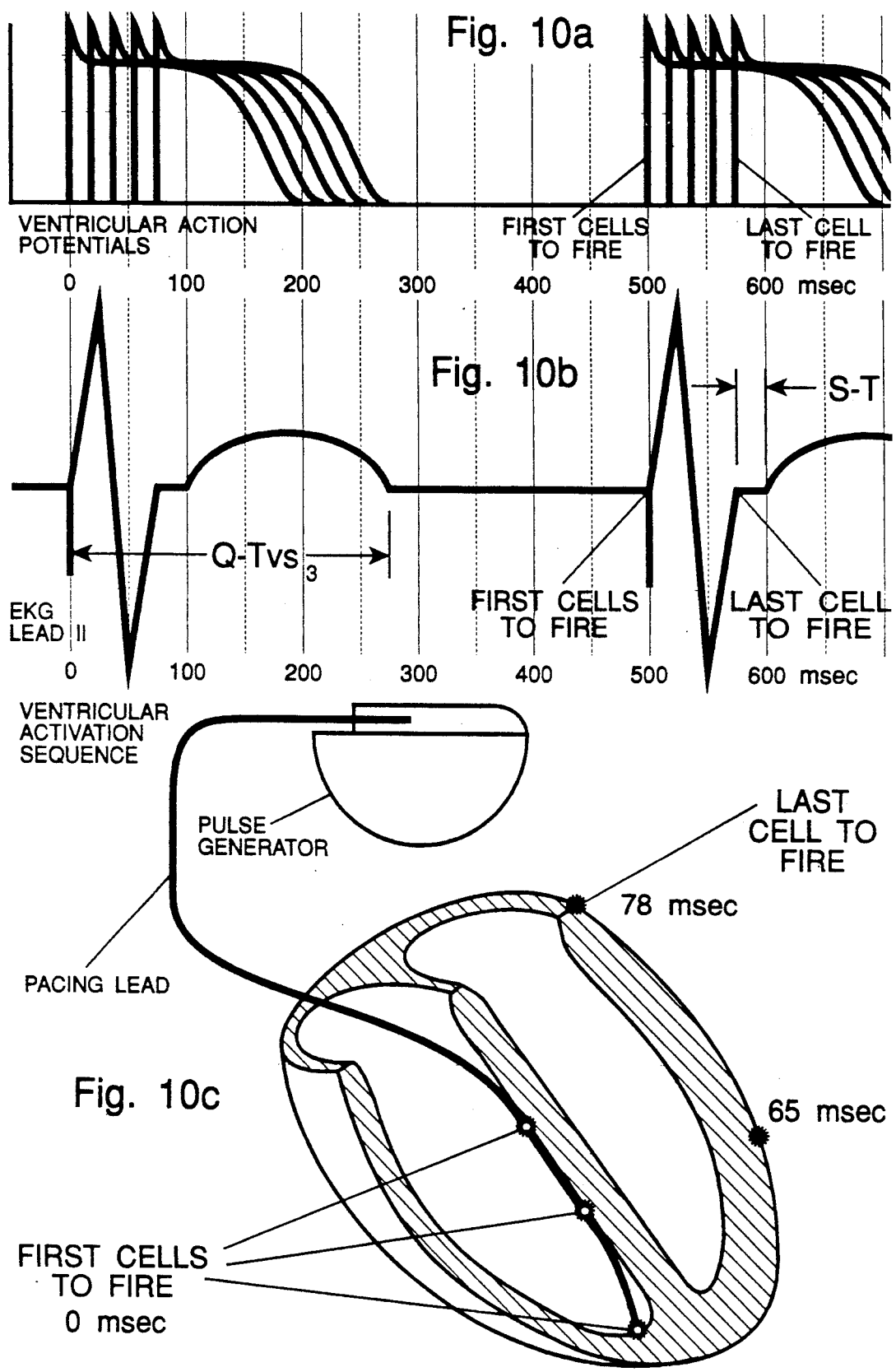
FIG. 10a illustrates the action potential distribution of a three focus ventricular sequentially paced ventricular activation sequence where one pacing electrode is placed at the right ventricular apex and the other two at septal positions.
FIG. 10b illustrates an electrocardiogram of a ventricular sequentially paced ventricular activation sequence where one pacing electrode is placed at the right ventricular apex and the other two at septal positions.
FIG. 10c illustrates the sequence of cell firing within a ventricular cross section of a three focus ventricular sequentially paced ventricular activation sequence where one pacing electrode is placed at the right ventricular apex and the other two at septal positions.
Figure 11:
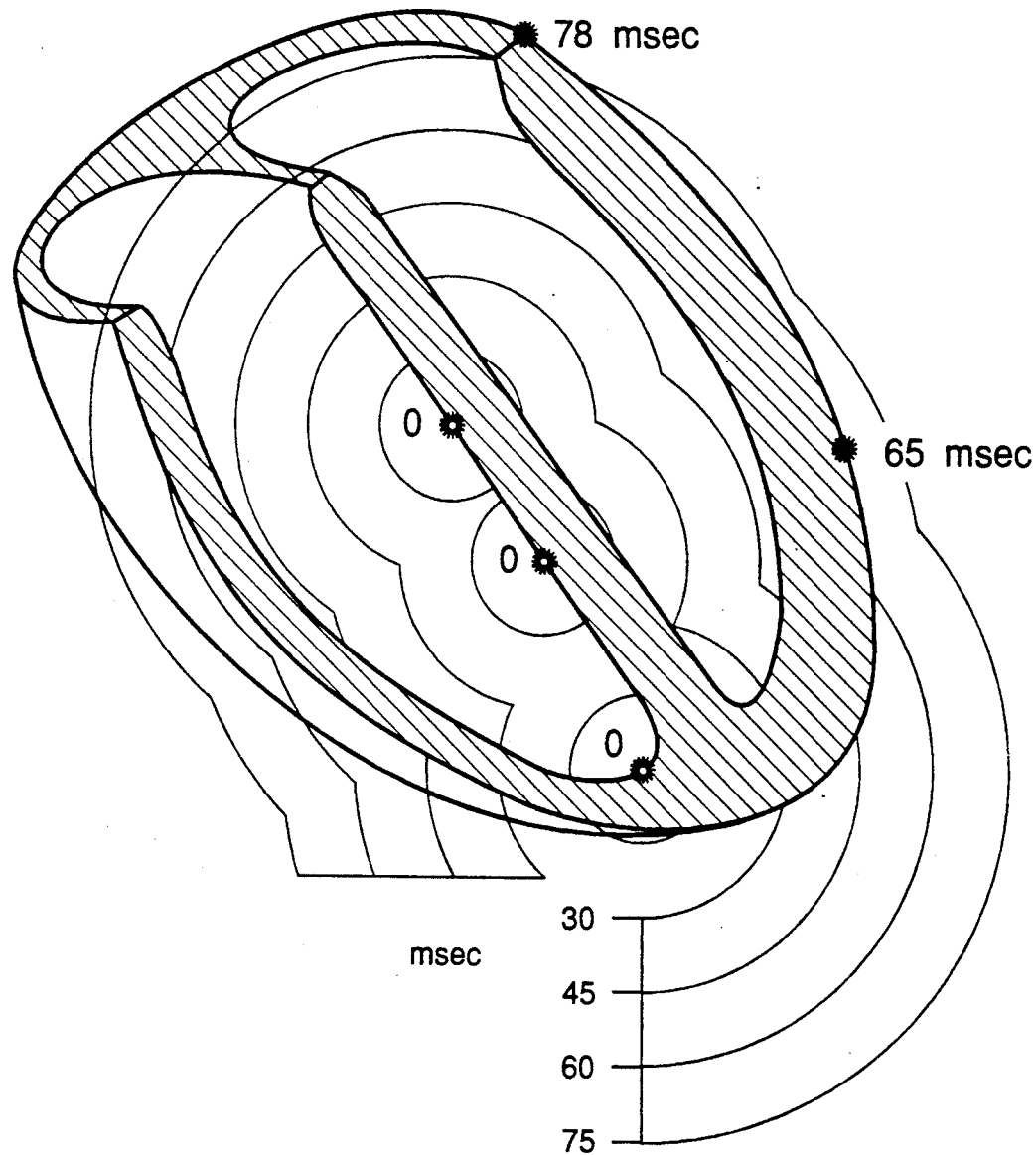
FIG. 11 illustrates the propagation of activation within a ventricular cross section during the three focus ventricular sequential pacing method as previously illustrated in FIGS. 10a-10c.

FIGS. 10a–10c and 11 illustrate three simultaneous firing pacing foci in a ventricular sequential pacing system that does not decrease the Q-Tcp interval to any greater extent than a two focus system, as shown in FIGS. 8a–8c and 9 due to the fact that the proximal electrode, as shown in FIG. 10c, is located as close to the last cell to fire as is possible just as in FIG. 8c. It does however, provide the ability of further prescribing a more desirable ventricular wall motion as illustrated in FIG. 11. In comparing FIGS. 8c and 9 to 10c and 11 it will be seen that in FIG. 8c the last cells fire at identical intervals of 78 msec while FIGS. 10c and 11 illustrate that a cell lower down on the left ventricular wall will fire at 65 msec at a position substantially comparable to that shown in FIGS. 8c and 9 which fired at 78 msec. Also as shown in FIG. 11, there is slightly less downward propagation of ventricular wall activation as compared to the two focus system of FIG. 9. It should be noted that more than three pacing foci may be employed to produce further Q-Tvs interval shortening and/or more desirable ventricular wall motions, at any location on the lead which yields an acceptable ventricular pacing threshold.

Figure 12:
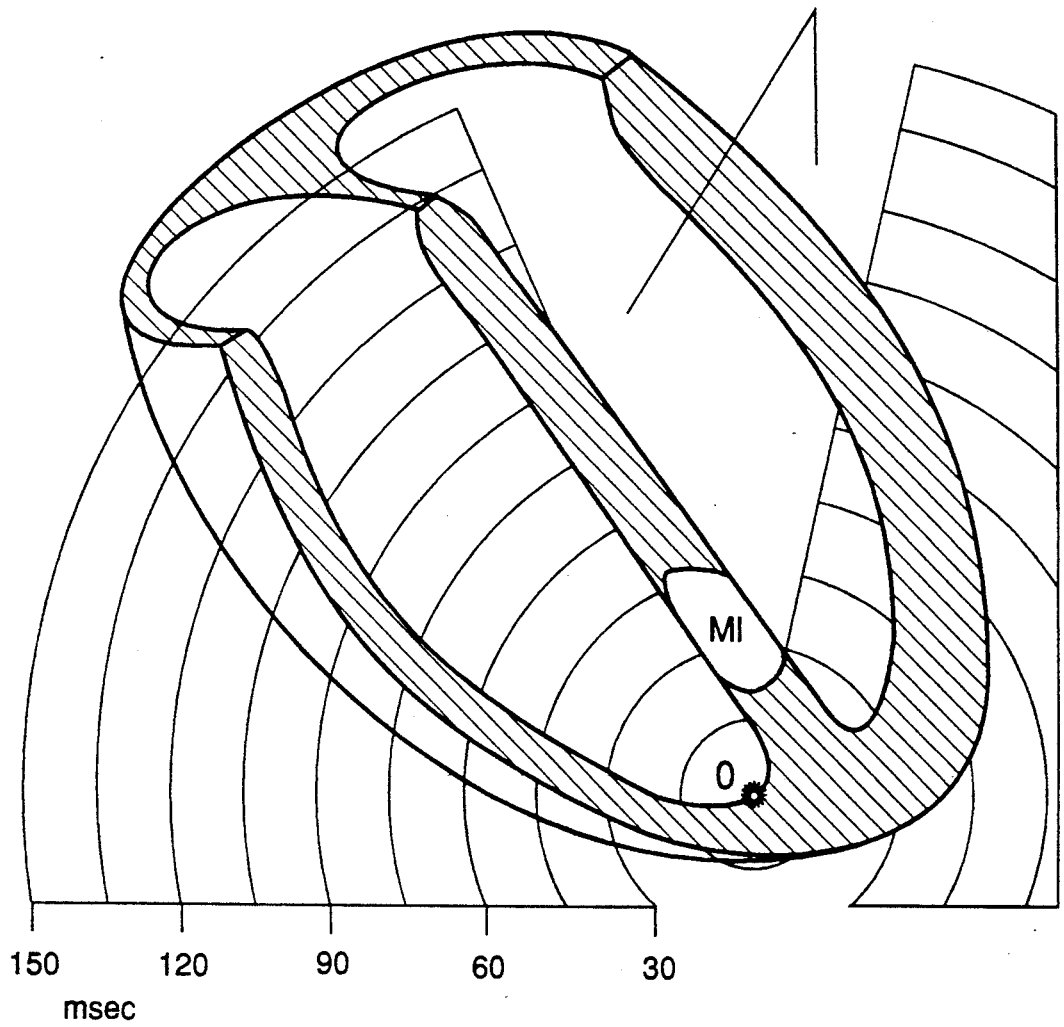
FIG. 12 illustrates the propagation of activation within a ventricular cross section that has been damaged by a myocardial infarction (MI), during conventional ventricular pacing.

FIG. 12 illustrates the further lengthening of ventricular activation that can occur when an area of infarcted ventricular tissue (non-viable cells) designated MI in FIG. 12 occurs in the ventricular septum and extends through to the ventricular epicardial surfaces, during conventional pacing. As shown there is an area of slowed propagation denoted by the white area within the propagation area as compared to FIG. 5, due to the fact that cell by cell propagation must travel around the infarction. Ventricular sequential pacing, as previously described and shown in FIGS. 6–11, can be of greater advantage in shortening the Q-T interval in this particular situation.

Figure 13:
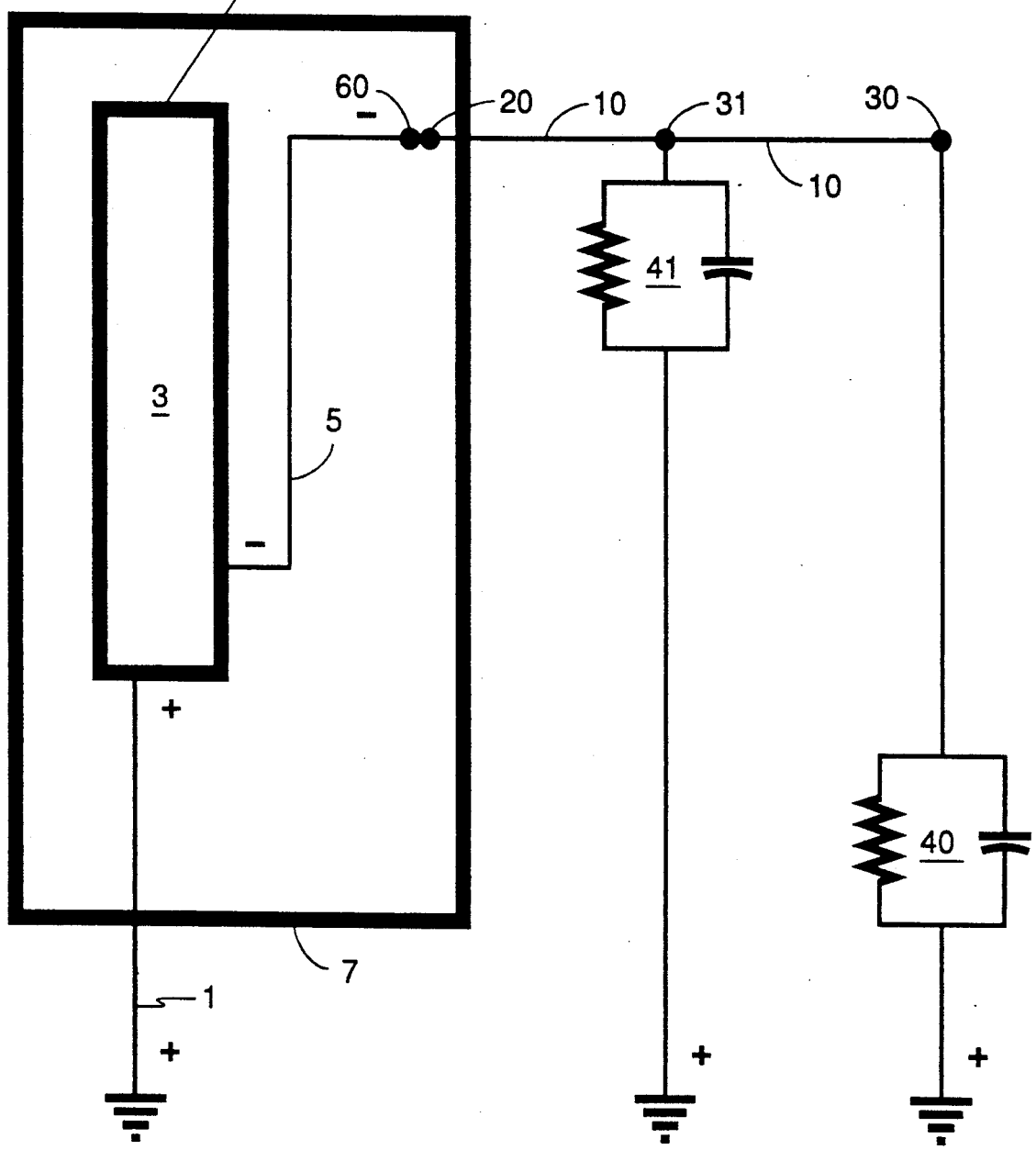
FIG. 13 is an electrical schematic of a single wire and circuit, twin focus ventricular sequential pacing system during pacing.
Figure 14:
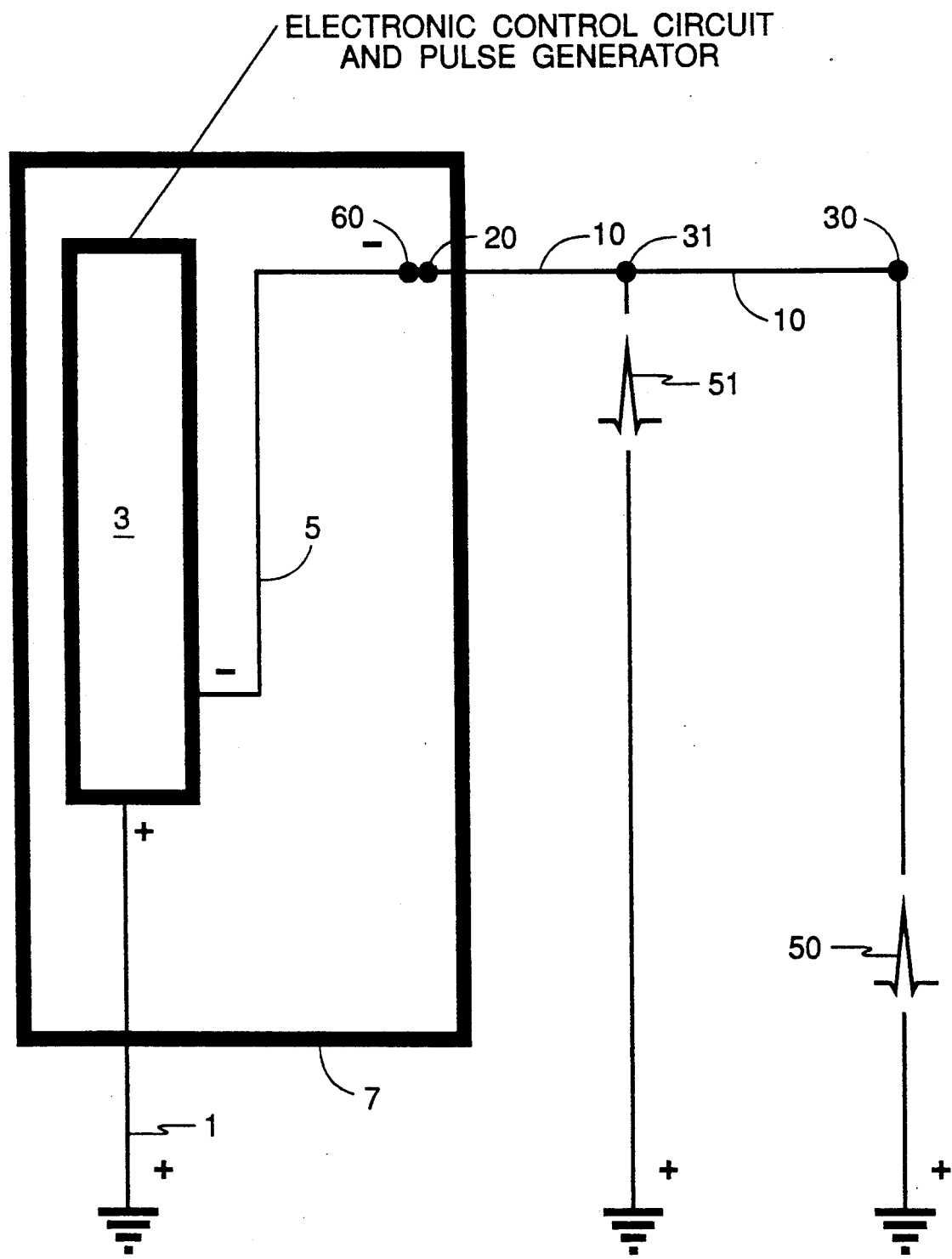
FIG. 14 is an electrical schematic of a single wire and circuit, twin focus ventricular sequential pacing system during sensing.

FIGS. 13–15b illustrate a circuitry that will support twin focus ventricular sequential pacing. As shown in FIGS. 13 and 14, a conventional unipolar pulse generator 7 which can be programmed to either the VVI, VVIR, VVT or VVTR pacing mode having circuitry and power source 3 connected by feed through wire 5 to a set screw or other suitable connection means 60 that electrically connects to pin 20 which is electrically connected to wire 10. It should be noted that the majority of conventional pulse generators employed today are constant voltage systems. The hereinafter described embodiments will be based upon constant voltage pulse generators but are equally valid when employed with constant current systems. Pacing electrodes 30 and 31 are electrically connected to wire 10 and are in electrical contact with ventricular muscle. Pacing electrode 30 forms the pacing focus 40 having ventricular capacitance and resistance of the ventricular muscle and sensing focus 50 (FIG. 14) between itself and the unipolar (pacemaker case) ground 1 of the pulse generator 7. Similarly, electrode 31 forms the pacing focus 41 and sensing focus 51 between itself and the unipolar ground 1. Pacing foci 40 and 41 are represented by a resistance and capacitance in parallel and sensing foci 50 and 51 are represented by a QRS signal as would be recorded from an EKG. FIG. 13 represents the pacing configuration thus obtained and FIG. 14 represents the sensing configuration thus obtained.

FIG. 15a illustrates the pacing lead configuration required, in an implantable system, to obtain two focus access with a negative polarity tip electrode 30 and negative polarity proximal electrode 31. Sealing rings 8 are provided to insulate the electrical connection between pin 20 and connection means 60 from tissue or body fluids. Insulation 91 surrounds wire 10 as shown in FIG. 15b and insulates it from electrical contact with tissue or body fluids. As further shown in FIG. 15b wire 10 is wound around tubing 90 which provides a central opening for stylet insertion. Projections 9, referred to as tines, may be provided to aid in securing the tip electrode during the initial phase of implantation.

Conventional pacemakers are generally employed using a positive electrical ground with the pacing electrode having a negative polarity. This convention will be followed in this and the hereinafter embodiments with the understanding that they are also valid if a negative ground were to be employed.

The electrical energy required to activate a ventricular muscle cell will be referred to as the pacing threshold. Threshold, in the following examples, will be expressed as a voltage threshold at a certain pulse width which is proportional to the electrical energy threshold in a constant voltage pulse generator.

Both pacing foci 40 and 41 are seen in FIG. 13 to form parallel electrical pathways between the negative pacemaker output feed through wire 5 and the ground with both operating at equal voltages delivered across electrode 30 and the common ground 1 and electrode 31 and the common ground 1. Current flow to each, in a constant voltage system will be equal only if the pacing foci 40 and 41 produce equal pacing impedances. If equal impedances were obtained, it would result in a combined lead impedance of one half the impedance of either 40 or 41 thus producing twice the current drain of a conventional pacemaker operating through a single focus of equal impedance at an equal pacemaker output voltage. It should be noted though that conventional pacemakers generally are programmed for a chronic safety margin of at least twice the voltage threshold of their single pacing focus to allow for threshold increases which may occur due to excessive endothelial tissue ingrowth, myocardial infarction or other factors. The use of two pacing foci produces a situation where the programmed voltage need only be programmed to two times the lowest of the two voltage thresholds obtained thus producing at least an equivalent safety margin when the pacing impedances of 40 and 41 are equal. The use of two pacing foci, by producing more than one focus at different sites, will produce a greater probability that a lower threshold will be obtained at the additional site of the proximal electrode 31 and a greater probability that factors which may increase threshold will not occur simultaneously at the widely separated sites of the electrodes. Should the proximal focus 41 yield a higher threshold than the tip focus 40 the necessary operating voltage for a two to one safety margin will be unchanged as compared to conventional pacing and ventricular sequential pacing will result provided the proximal focus 41 has a threshold of no greater than two times the tip focus 40, and further provided that the impedances of 40 and 41 are equal. Should the proximal electrode's threshold be greater than twice the tip electrode's threshold, the operating voltage of the pacemaker will need to be increased to meet the proximal electrode's threshold voltage in order to obtain twin focus ventricular sequential pacing.

Sensing is accomplished with a conventional sensing amplifier that will experience two intrinsic ventricular signals occurring at different times according to the individual heart's conduction pattern thus increasing sensing reliability substantially. Small variations in the interval at which various intrinsic signals are sensed will result, as compared to conventional pacing, dependent upon whether, for instance, QRS signals, which will be sensed initially from the proximal sensing focus, or premature apical ventricular contractions, which will be sensed initially from the tip sensing focus, occur. Thus, when a normal QRS signal occurs it will be sensed more quickly in this ventricular sequential pacing system than in a conventional pacing system. It should be understood that during a cardiac cycle, the second intrinsic signal sensed by the conventional sensing amplifier, in this embodiment, will fall within the refractory period of the amplifier provided the refractory period is longer than the intrinsic QRS duration, thus becoming ineffective and that if one intrinsic signal becomes too small to be sensed, sensing of the other will be unaffected as long as it remains of sufficient amplitude. When the tip focus impedance 40 and the proximal focus impedance 41 are unequal, which is probable due to biologic variation and to their different positions with respect to the ground 1, threshold safety margin analysis becomes more difficult due to the resulting variation in current drain between the two pacing foci 40 and 41 which may not be within the pulse generator's capability of compensating for to achieve pacing through both foci at a reasonable overall current drain for an implantable pacing system. This system is, however, suitable for temporary pacing where current drain requirements are easily compensated for by the employment of an external power source whose batteries can be very large or non-invasively changed. Temporary pacing systems are generally employed with a bipolar ground which will be described in various configurations for use with ventricular sequential pacing systems hereinafter. It should be understood that lead impedances, as measured from conventional pacemakers with telemetry, may vary widely from patient to patient and may vary in an individual heart over time. Exit block, defined as a threshold voltage which is beyond the voltage a pulse generator is capable of delivering, may occur after lead insertion as a result of excessive endothelial tissue ingrowth, myocardial infarction or other causes which may gradually increase threshold over time or may occur suddenly.

Operation of this system in the VVI or VVIR mode will produce single chamber ventricular sequential pacing at the preset or sensor indicated rate. Operation of this system in the VVT or VVTR mode offers additional advantages due to the fact that sensed intrinsic signals, which occur above the preset or sensor indicated rate, and which have wider than normal QRS morphologies, will be fired into in order to produce a shorter QRS duration than could be obtained with conventional pacing. Diseases which produce wider than normal QRS complexes at normal atrial initiated rates are various degrees of bundle branch block, in particular right and left complete bundle branch block. Arrhythmias which produce wider than normal QRS morphologies at ventricular initiated rates are premature ventricular contractions. VVT and VVTR ventricular sequential pacing are new forms of treatment for these diseases which are especially applicable during temporary pacing immediately following a myocardial infarction when shortening QRS intervals can be of great value in increasing coronary artery perfusion. Three or more pacing and sensing foci may also be employed in this embodiment, in order to produce further Q-T shortening and/or more desirable ventricular wall motions.

FIGS. 16, 17, 19a and 19b illustrate a twin focus ventricular sequential pacing system that provides the ability to non-invasively, either in an implantable or external system, independently adjust the voltage and pulse width delivered to each pacing electrode 30 and 31. The pulse generator circuitry and power source 4 consists of two interdependent, independently power programmable circuits basically similar in operation to conventional pulse generator circuitry currently employed for dual chamber pacing with the important novel modification of a 0 to 75 msec programmable delay between the pulses delivered and the capability to pace and sense independently through two ventricular foci. Descriptions of pacing modes employed hereinafter will follow the convention established by The North American Society of Pacing and Electrophysiology as they are currently applied to conventional pacing systems. New mode descriptions for ventricular sequential pacemakers, that are anticipated to be required, will be left for the appropriate authorities to determine. DDI, DDIR, DDD, DDDR, DVI, DVIR, pacing modes and any of their committed variants, single chamber modes or other modes may also be programmed with the aforementioned modifications. These circuits have two individual negative feedthrough outputs 6 which are electrically connected independently to pin 20 and contact 21 by set screws or other suitable connection means 60 and 61 respectively. Pin 20 is electrically connected to wire 10. Contact 21 is electrically connected to wire 11. Pacing electrode 30 is electrically connected to wire 10 and is in electrical contact with ventricular muscle, to form pacing focus 40 and sensing focus 50 (FIG. 17) between electrode 30 and the unipolar pulse generator ground 1. Similarly, pacing electrode 31 is electrically connected to wire 11 and is in electrical contact with ventricular muscle, to form pacing focus 41 and sensing focus 51 between electrode 31 and the unipolar pulse generator ground A construction is shown in FIG. 18 which allows two or more single strand or multifilar wires to be placed in a single lead. As shown in FIG. 18, the lead is provided with a flexible central tube 90 which allows for insertion or removal of a stylet. Wire 10 is coaxially wound about tube 90. A layer of insulation 91 encloses wire 10. Wire 11 is coaxially wound about insulation 91 and is enclosed by a layer of insulation 92. Wire 12 is coaxially wound about insulation 92 and is enclosed by insulation 93. Thus, each of wires 10, 11 and 12 are electrically insulated from each other and from body fluid or tissue contact by layers of insulation 91, 92 and 93. Tube 90 and the insulating layers can be made of polyurethane or silicone rubber compositions, and may vary in outside diameter to form an uninterrupted lead surface for atraumatic insertion.

Wires 10, 11 and 12 will be referred to in the description of subsequent lead configurations, in order to describe their level within the lead construction method of FIG. 18. The lengths of wires 10, 11 and 12 may therefore vary dependent upon the particular lead configuration considered. Thus, wire 10 is at the innermost level and wire 12 at the outermost level of the lead.

Figure 19A:
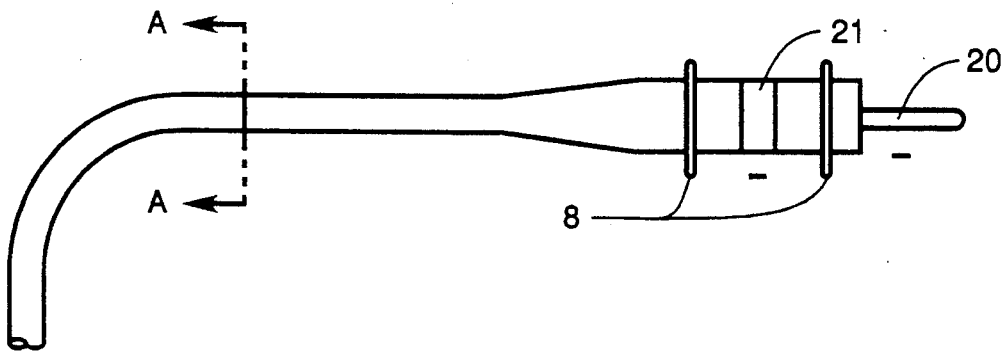
FIG. 19a is a front view showing a twin focus dual wire pacing lead for use with the circuitry shown in FIGS. 16 and 17.
Figure 19B:
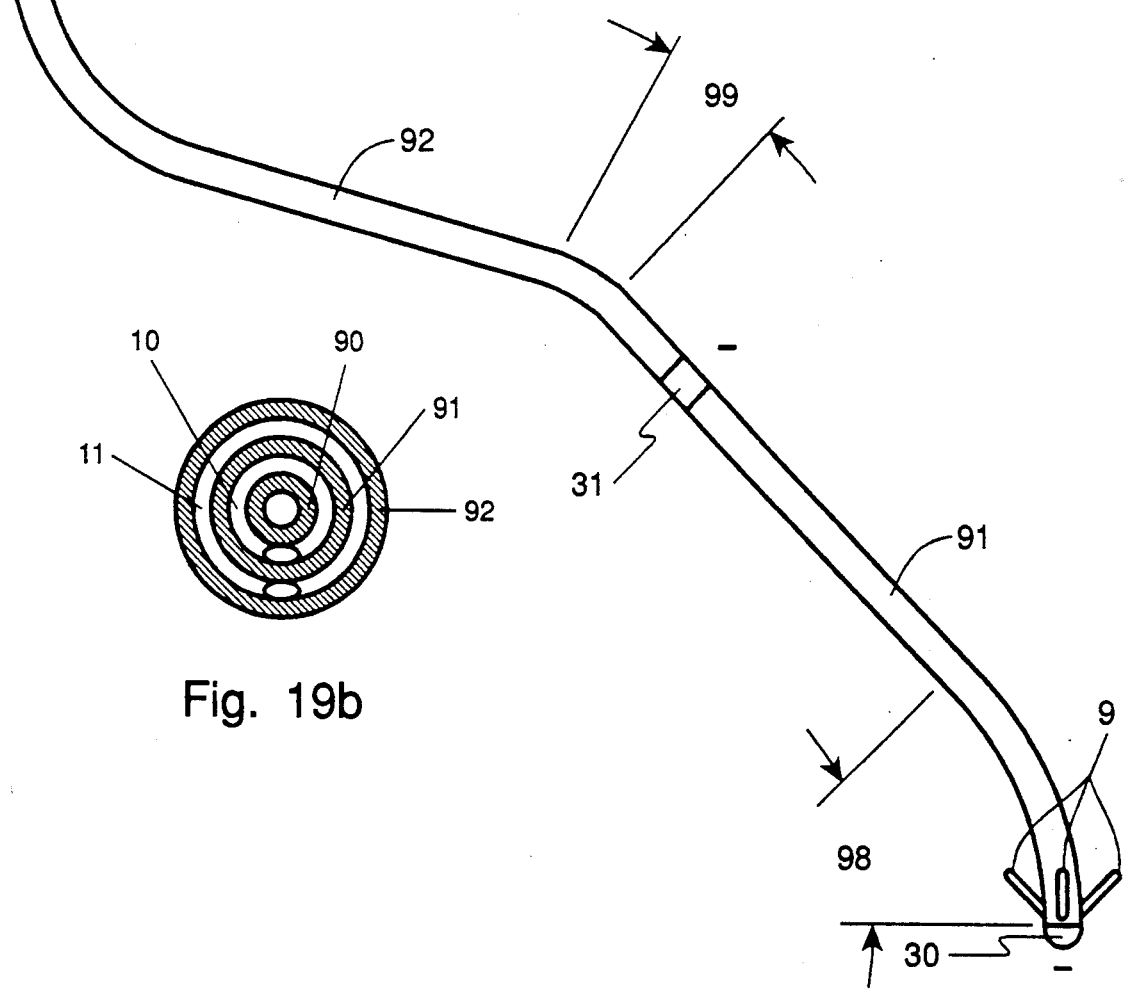
FIG. 19b is a section through said pacing lead.

While a portion of the length of conventional pacemaker leads placed in the ventricle by present techniques may make contact with the ventricular septum, as hereinbefore shown, they may also lie along the right ventricular wall. Ventricular sequential pacing according to the present invention can also be achieved with right ventricular proximal electrode wall contact but without the degree of Q-T interval shortening obtainable with proximal septal electrode contact in the treatment of complete atrio-ventricular block. Septal wall contact of the proximal electrode in complete AV block will be preferred for this reason. However, right ventricular wall placement of proximal electrodes can be of value in the treatment of right bundle branch block and/or right ventricular wall infarctions by shortening the contraction sequence of the right ventricular wall to more closely approximate that of the left ventricular wall. In a similar manner, left ventricular wall contact by electrodes, either by transeptal means or epicardial electrode placement, will be of value in the treatment of left bundle branch block and/or left ventricular wall infarction. FIGS. 19a, 19b illustrates an implantable twin focus pacing lead configuration which includes two preformed curvatures 98 and 99 on the lead which can be straightened by stylet insertion for ease of vein introduction. Upon stylet removal, following lead placement, curvatures 98 and 99 will reform as an aid in obtaining contact with the ventricular septal wall by the proximal electrodes, or in this case, electrode 31. Rotation of this lead configuration may be employed to obtain right ventricular wall contact of certain electrodes when advantageous to do so.

This twin focus ventricular sequential pacing system with independently programmable circuitry for each pacing electrode has significant advantages over the ventricular sequential twin focus pacing system shown in FIGS. 13-15b Pacing focus impedances can be individually measured and monitored independently in order to isolate the individual properties of each over time. Focus impedances, as monitored by telemetry systems, generally decrease in the presence of an increased pacing threshold and increase in the presence of a decreased pacing threshold. Thus continuous monitoring of focus impedances may be employed to automatically program to the most efficient and safest electrode or combinations of electrodes available. Power consumption is more controllable since different pacing voltages and pulse widths can be programmed for each pacing focus. Also, the employment of two pacing foci eliminates the possibly lethal consequences of a myocardial infarction or excessive endothelial tissue ingrowth causing sudden exit block at one pacing focus. It is believed that this system may result in a greater pacing safety margin, when each independently programmable pacing voltage is ten percent above the pacing threshold at a selected pulse width for each focus, than is obtainable with a conventional one focus lead system with a voltage set at two times the individual focus pacing threshold at the same selected pulse width. Thus in certain situations, a power saving may result as compared to conventional pacing. Independently programmable sensing circuits also increase the reliability of sensing in a similar manner. Pacing site redundancy, circuit redundancy and the optional addition of battery redundancy can produce greater ventricular pacing reliability than may be obtained with conventional ventricular pacing systems. Although FIGS. 8a-8c and 9 illustrate simultaneous firing of the two pacing foci, it is also possible in the circuitry configuration of FIGS. 16 and 17 to program a small delay between the impulse delivered to the tip electrode and the impulse delivered to the proximal electrode thus producing a more normal ventricular contraction sequence at the expense of lengthening the Q-T interval somewhat. This may be of value under certain physiologic circumstances based upon ventricular imaging by ventricular angiography or echocardiography, or cardiac output studies in an individual pacemaker recipient. When programmed to the DDD, DDDR, DDI or DDIR modes, sensing of an intrinsic ventricular signal within the delay period may produce a variable ventricular pacing rate, but this variance cannot exceed the delay interval selected, and is dependent upon whether timing is based on the proximal or distal electrode. Sensing of the first pacing impulse by the second sensing circuit may occur unless a sufficient blanking period is programmed and/or bipolar pacing systems are employed. Committed DVI, DVIR, DVT and DVTR pacing modes will obviate this potential problem area at the expense of losing one sensing focus. Sensing or firing of the tip electrode can precede sensing or firing of the proximal electrode when a delay is selected or the opposite firing and sensing order may be chosen with the addition of appropriate programmable circuitry. DDD, DDDR, DVD, DVDR, DAD and DADR modes may be employed with a 0 msec delay to produce QRS shortening at the intrinsic rate as described hereinbefore in reference to VVT pacing in the circuitry configuration of FIGS. 13-15b. Rate adaptive sensors may also be incorporated with this ventricular sequential system in order to switch between a one focus mode, to save power at lower sensor indicated rates, and a two focus mode, to produce Q-T shortening above a desired sensor or atrial indicated rate. It is intended that more than two interdependent circuits may be selectively employed, by programming alone or a programmed sensor or atrial indicated rate range, in conjunction with an equal or greater number of electrodes, with one circuit pacing and sensing through one or more electrodes, and programmed to fire in a selected order and sequence or simultaneously, to produce the ventricular response most desired. The delay between electrodes or electrode sets may also be programmed to shorten proportional to increasing sensor or atrial indicated rates.

Figure 20:
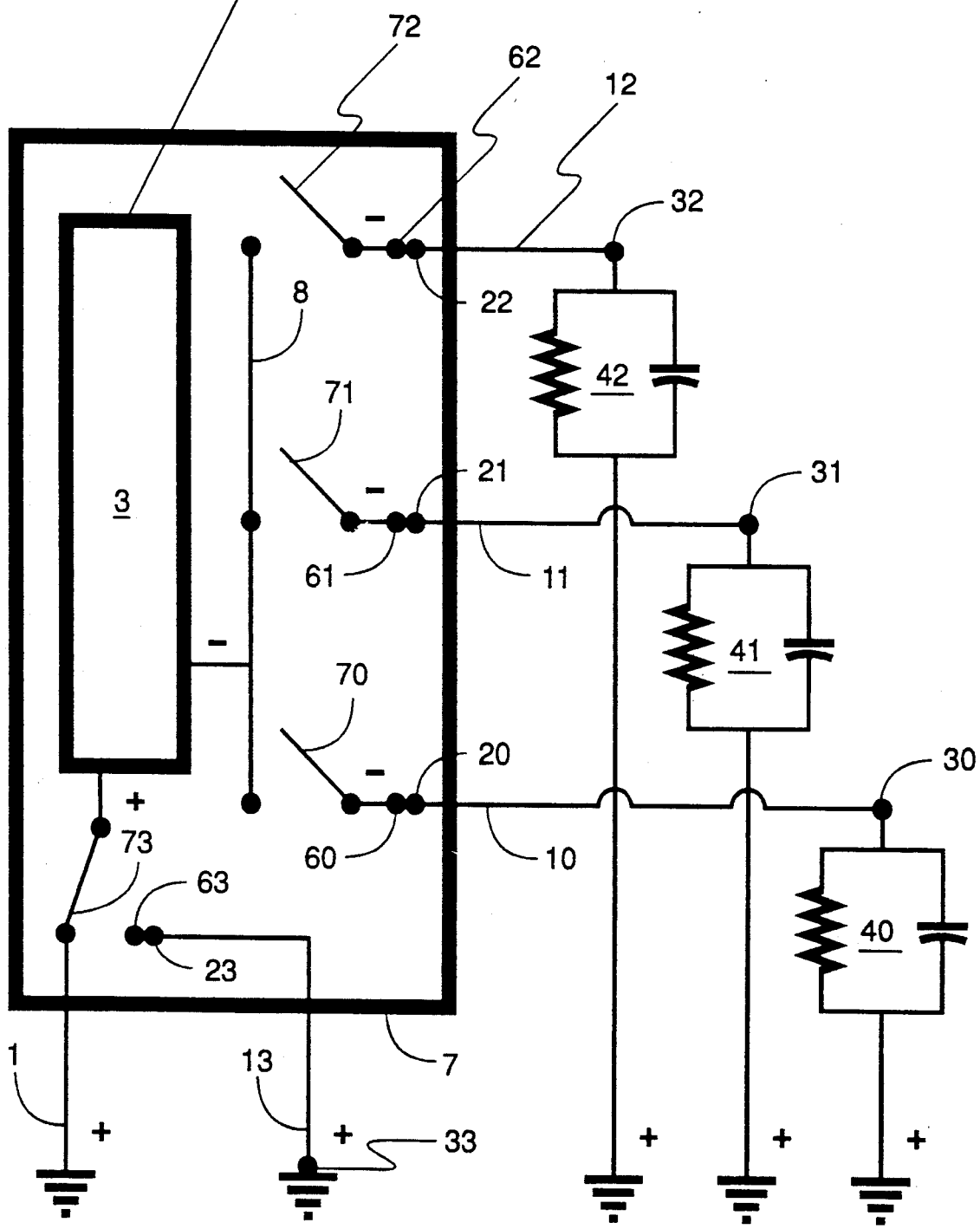
FIG. 20 is an electrical schematic of a four switch, four wire, single circuit, three focus ventricular sequential pacing system during pacing.

FIGS. 20-24 illustrate the use of programmable switches 70, 71 and 72 to direct pacing stimuli to a selected focus or selected group of foci, and sense intrinsic signals from a selected focus or a selected group of foci. Switch 73 can be employed to switch polarity from unipolar to bipolar or vice versa. Circuitry to form these programmable switches currently exists in conventional pulse generators and is incorporated in systems where pacing and sensing polarity (unipolar and bipolar) can be programmed independently in an individual lead. FIGS. 20, 21, 22a and 22b illustrate the location of switches 70, 71 and 72 with one of their poles electrically connected to the pulse generator circuitry output (negative terminal) 8 and the other of their poles electrically connected to the pulse generator connections 60, 61 and 62 respectively. Switch 73 is electrically connected at one pole to the pulse generator circuitry ground (positive terminal) of the circuitry and power source 3 with the ability to switch from ground connection 63 to the unipolar case ground and vice versa. FIGS. 20-22a and 22b also show a three focus circuit which can use the lead shown in FIG. 23, which lead as shown in FIG. 23b incorporates wires 10, 11, 12 and 13 and insulating layers 91, 92, 93 and 94 along with stylet receptacle tube 90. As shown in FIG. 20, electrical contact 22 is electrically connected to wire 12 and is electrically connected to one pole of switch 72 by a set screw or other suitable connection means 62. Electrode 32 is electrically connected to wire 12 and is in electrical contact with ventricular muscle, forming pacing focus 42 and sensing focus 52 (FIG. 21) between itself and either the bipolar ground 33 or the unipolar ground 1, dependent upon the position of switch 73. Electrical contact 23 is electrically connected to wire 13 and is electrically connected to one pole of switch 73 by a set screw or other suitable connection means 63. Electrode 33 is electrically connected to wire 13 in order to provide a bipolar pacing or sensing ground, when switch 73 electrically connects it to the ground terminal of circuitry 3. As shown in FIG. 23b, wire 13 is electrically insulated from wire 12 by insulation 93 and is insulated from tissue or body fluid contact by outer insulation layer 94 according to the coaxial winding construction described in connection with FIG. 18.

Figure 21:
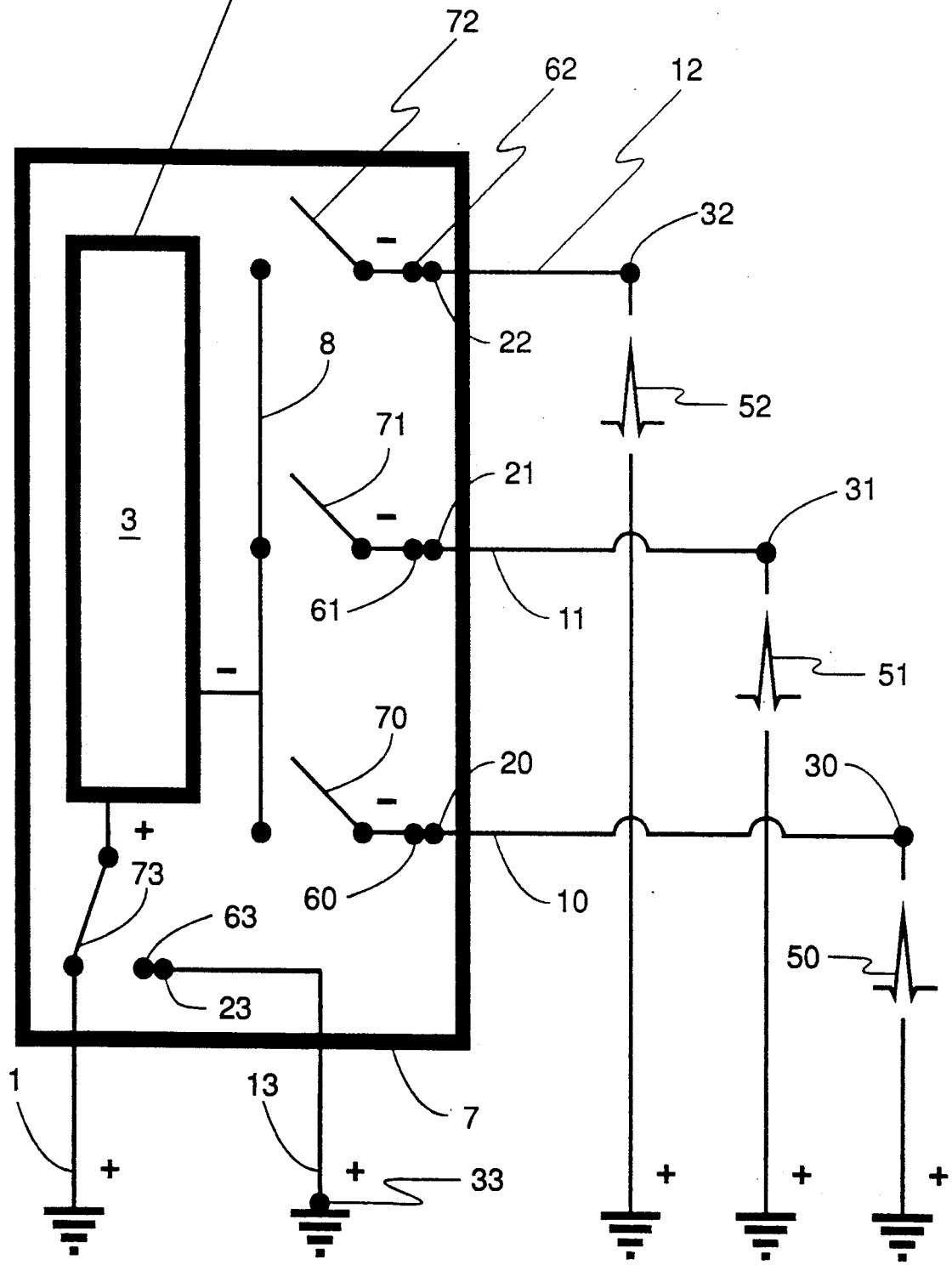
FIG. 21 is an electrical schematic of a four switch, four wire, single circuit, three focus ventricular sequential pacing system during sensing.
Figure 22A:
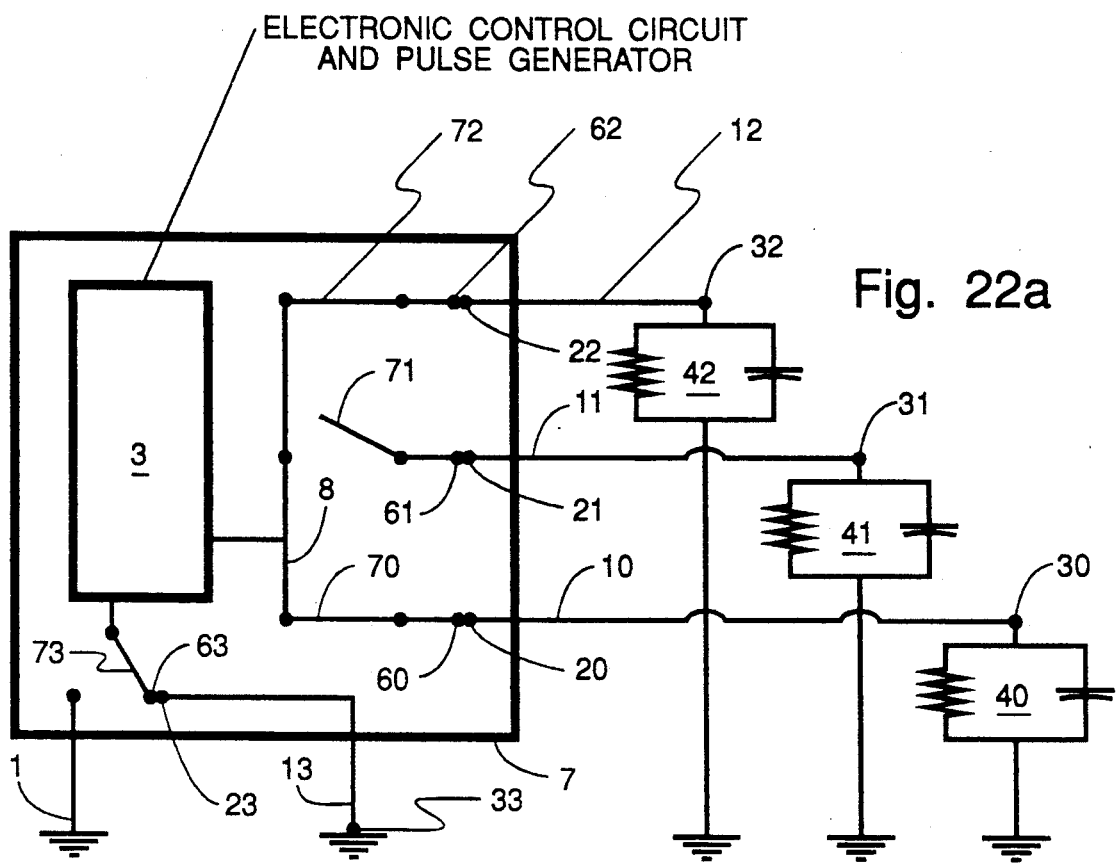
FIG. 22a is an electrical schematic showing the circuitry of FIG. 20 during pacing and FIG. 22b is an electrical schematic showing the circuitry of FIG. 21 during sensing, each one having a programmable combination of switch positions.
Figure 22B:
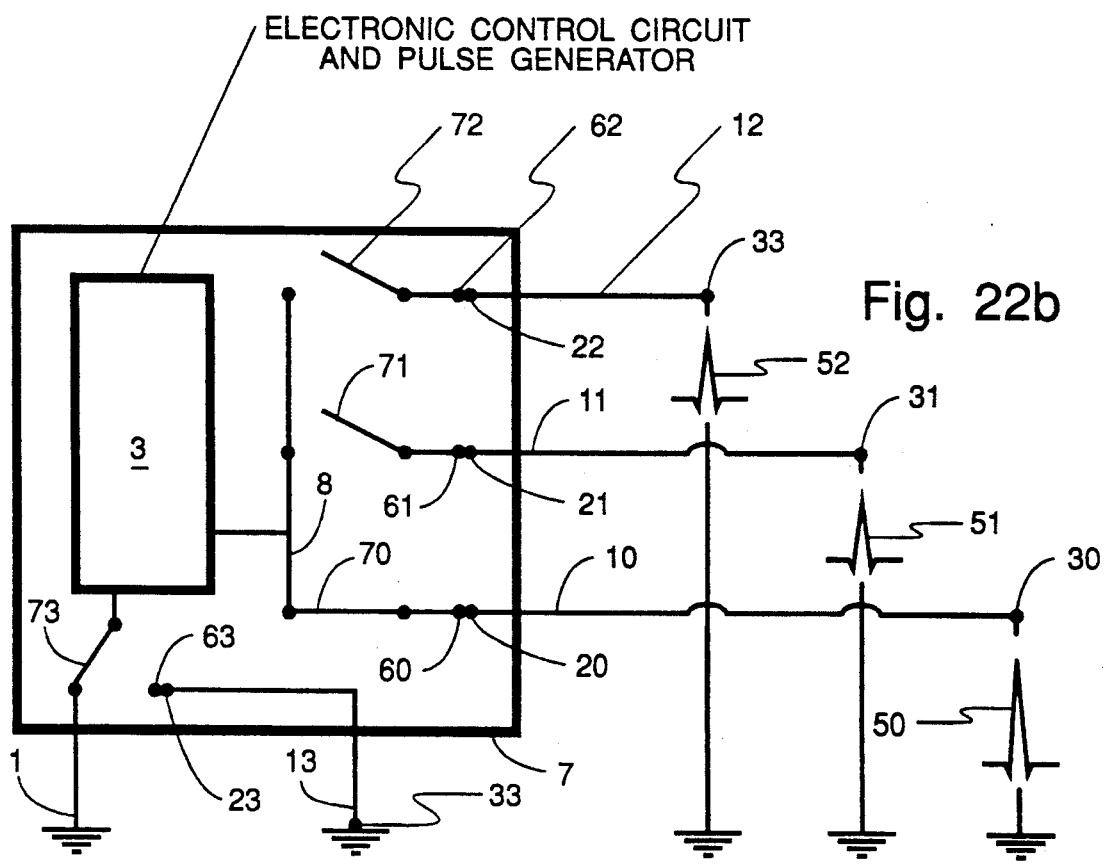

FIG. 20 also illustrates the possible pacing circuit configurations thus obtained and FIG. 21 illustrates the possible sensing circuit configurations thus obtained. FIGS. 22a and 22b illustrate one of the possible circuit configurations available when pacing is accomplished with a bipolar ground through pacing foci 40 and 41, and sensing is accomplished with a unipolar ground through sensing focus 50. All combinations of switch positions of 70, 71 and 72, except all open, may be employed to achieve ventricular sequential or conventional pacing, and sensing from one or more foci, with the additional combination of a bipolar or unipolar ground available in either of the selected pacing or sensing configurations. If switches 70, 71 and 72 are all open during pacing, the pacemaker is off and if all are open during sensing the pacemaker becomes asynchronous. Switches 70, 71 and 72 may also be triggered by a rate adaptive sensor or atrial tracking rate, to for example, pace through one or two foci during lower sensor or atrial indicated rates, in order to conserve power, pace through two foci during an intermediate sensor or atrial indicated rate range and pace through three foci over a selected sensor or atrial indicated rate in order to improve ventricular function when demand for cardiac output is high. All the various combinations of switch positions are intended to be selectively triggered either simultaneously or with a timed delay or rate responsive time delay between them in any order, by appropriate programming during certain sensor or atrial indicated rate ranges based upon the most desirable response received from an individual patient. It is also intended that two or more switches may be employed in conjunction with an equal or greater number of electrodes with one switch controlling one or more electrodes, in order to achieve the most desirable ventricular response for an individual patient.

Figure 24:
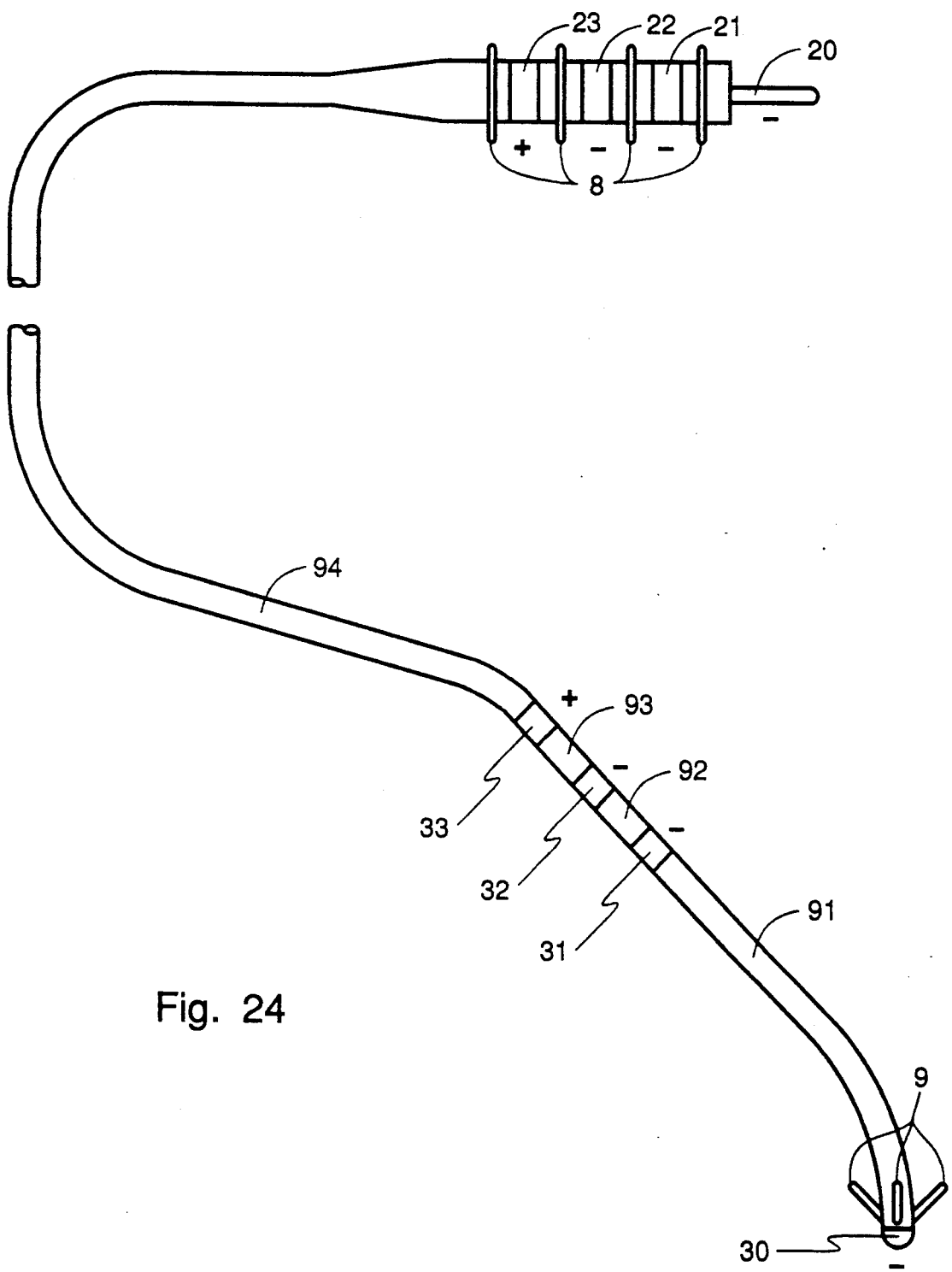
FIG. 24 is a front view showing a three focus, four wire pacing lead for use with the circuitry shown in FIGS. 20, 21 and 22; and wherein the two proximal foci are more closely spaced than shown in FIG. 23.
Figure 25:
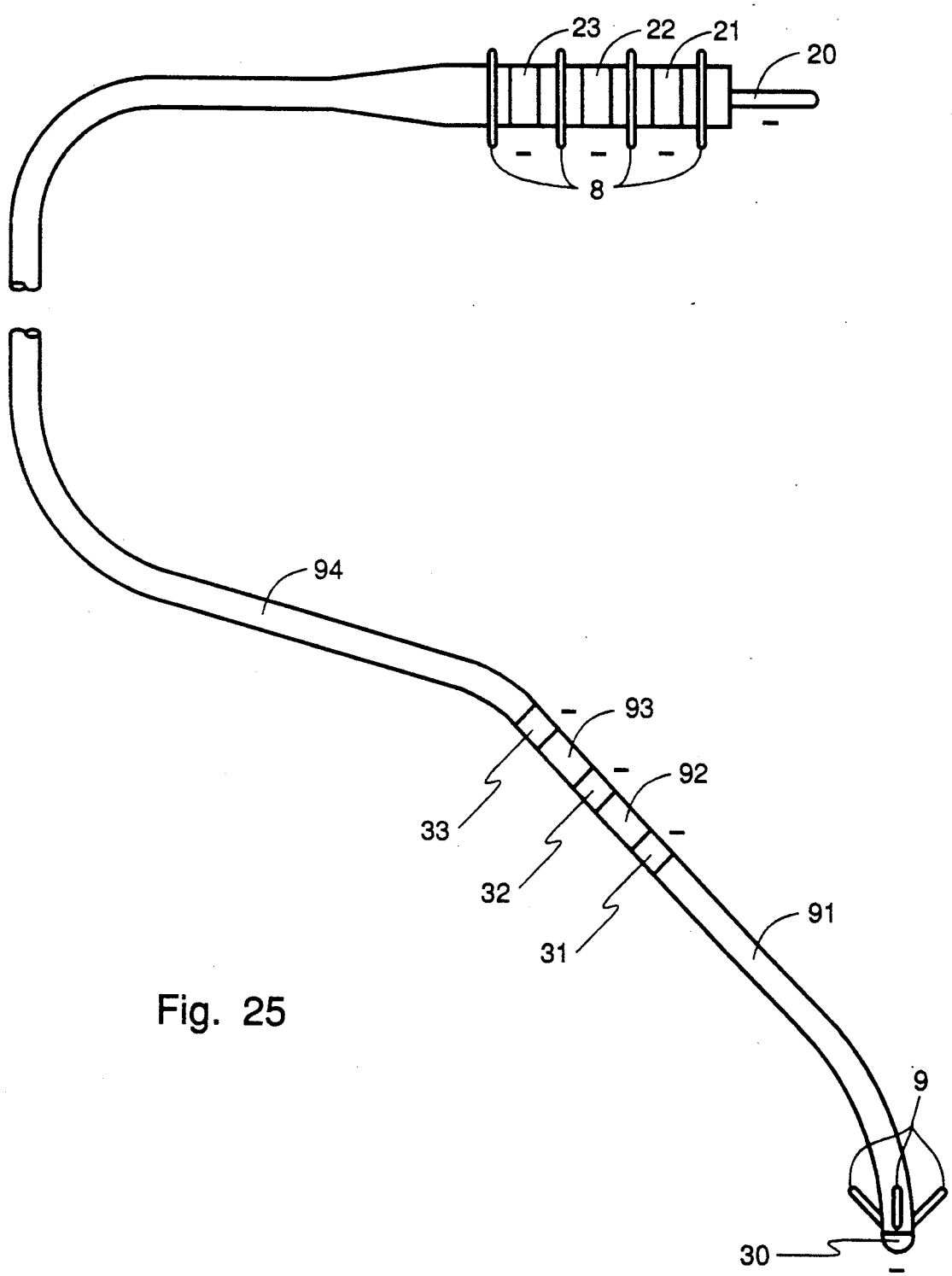
FIG. 25 is a front view showing a four focus, four wire pacing lead for unipolar ventricular sequential pacing.

FIG. 23a illustrates the implantable lead configuration thus formed with a tip electrode 30, a septal electrode 32 and an electrode 31 approximately halfway in between, that can be employed for one, two or three focus ventricular sequential pacing or conventional pacing may be accomplished when employing the tip electrode solely. FIG. 24 illustrates an implantable lead with the same basic configuration as that of FIG. 23a modified so that electrode 31 is placed closer to electrode 32 in order to yield a selection of mid-septal positions from which pacing foci may be chosen to obtain more closely the septal position at which maximum Q-T interval shortening will occur during either single or twin focus ventricular sequential pacing. FIG. 25 illustrates an implantable lead with the same basic configuration as that of FIG. 24 modified so that the polarity of electrode 33 is changed by connecting it to the negative output of the pulse generator by a switch in order to provide a selection of three mid-septal positions for achieving Q-T shortening in a unipolar pacing configuration. The programmable selection of mid-septal positions in an implantable system could be especially valuable when heart enlargement occurs after implantation requiring a relocation of the pacing focus to obtain the maximum Q-T shortening possible.

Figure 27A:
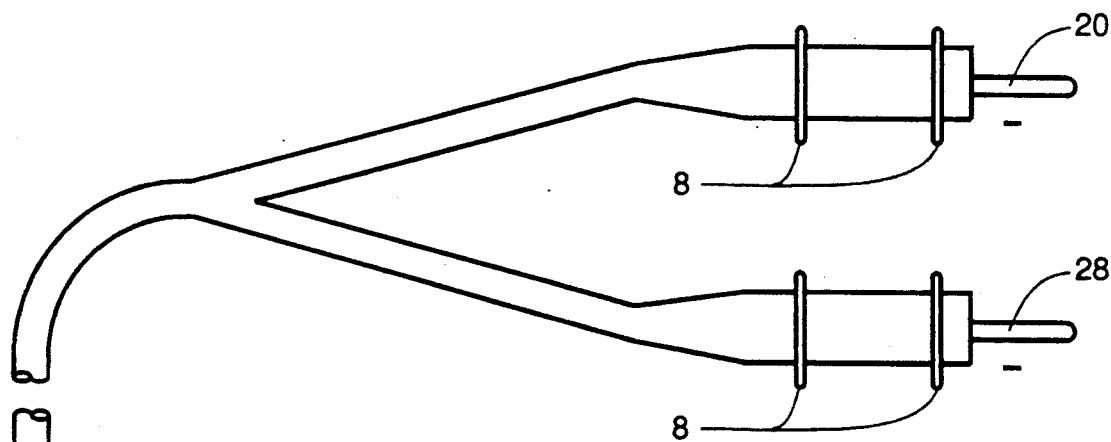
FIG. 27a is a front view showing a two focus, two wire pacing lead with side by side windings, for ventricular sequential pacing.
Figure 27B:
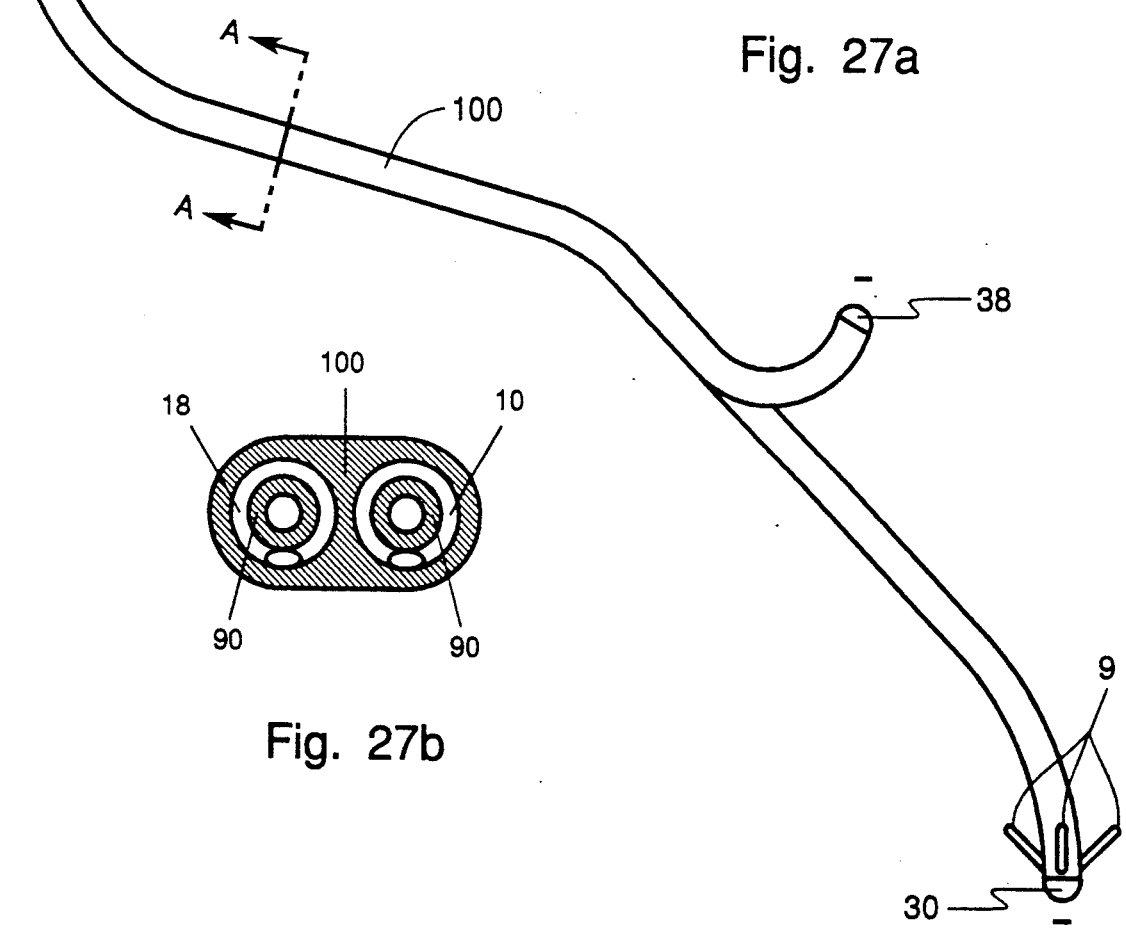
FIG. 27b is a section through said lead.

FIGS. 26a and 26b illustrates a three wire, twin focus implantable lead with the ground electrode 31 located midway between pacing electrodes 30 and 32 in order to achieve symmetrical electrical pathways for pacing and sensing through each electrode during bipolar operation. FIGS. 27a and 27b illustrate a unipolar two focus lead construction, with side by side coiled wires, employing two electrodes each having a negative polarity and both located in the ventricle. Contact 20 is electrically connected by means of a wire 10 to electrode 30. Contact 28 is electrically connected to electrode 38 by means of a second wire 18. The two wires are electrically insulated from each other and from blood and tissue contact by appropriate insulation 100. A preformed lead curvature proximal to electrode 38 is shown as an aid in positioning electrode 38 to achieve electrical contact with the ventricular septum, or by rotation, with the right ventricular wall, in a desired position which may be unobtainable by other methods of lead construction. This type of lead construction permits the use of two stylets, one of which would be intended for straightening the preformed curvature, proximal to electrode 38, for atraumatic vein insertion. The lead configuration of FIG. 27a also permits the employment of two tip electrodes 30 and 38.

Figure 28:
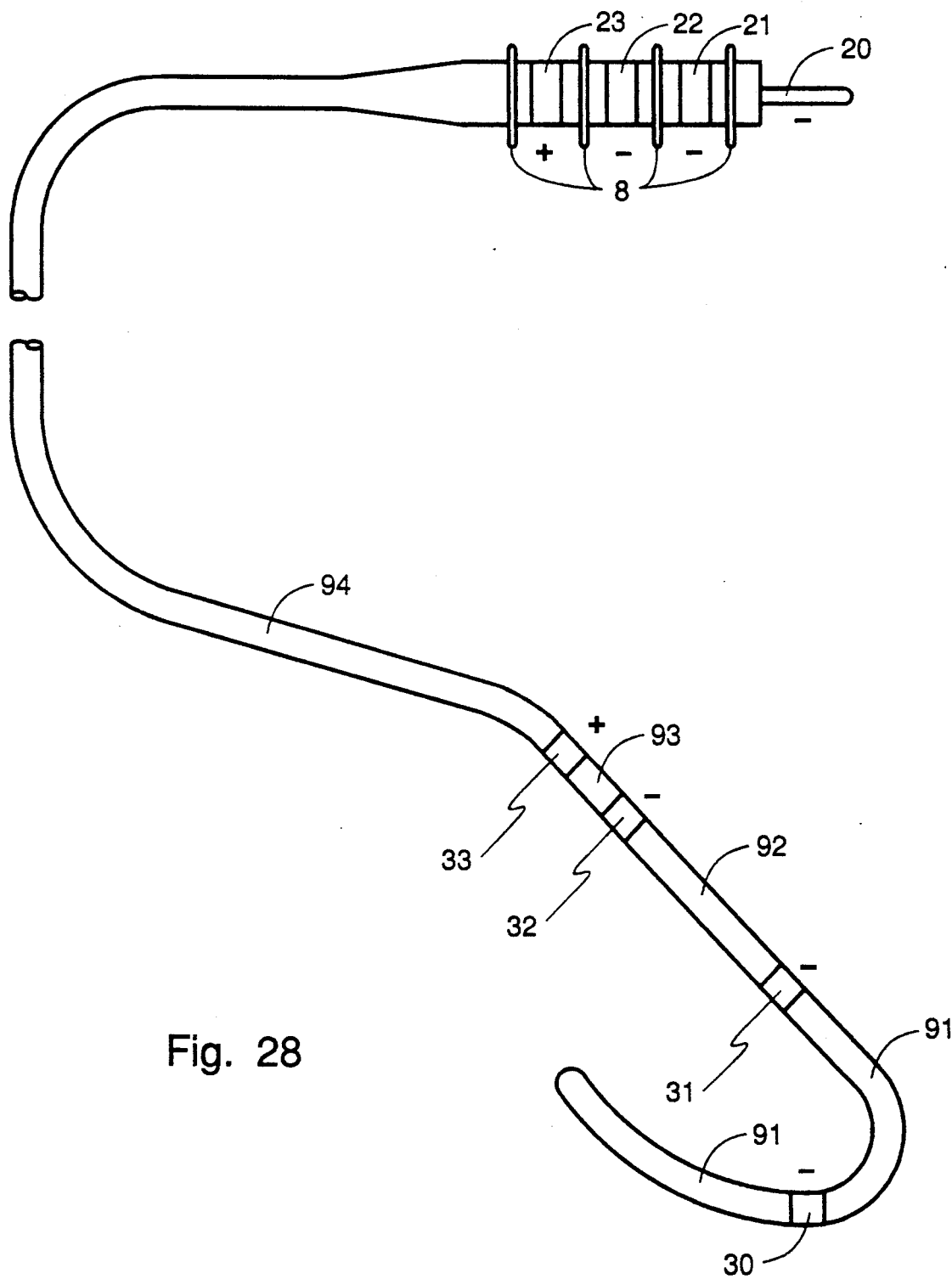
FIG. 28 is a front view showing a three focus, four wire pacing lead for use with the circuitry shown in FIGS. 20, 21 and 22.

FIG. 28 illustrates another implantable lead with the same basic configuration as that of FIG. 23a modified with a preformed lead curvature distal to electrode 31 and the relocation of electrode 30 from the tip to a position on the preformed curve. Stylet insertion permits straightening of the preformed curvature for atraumatic vein insertion. This lead configuration shows another technique of obtaining septal wall contact for the proximal electrodes or with optional rotation septal and right ventricular wall electrode contact for the treatment of right bundle branch block, and/or right ventricular wall myocardial infarctions. This lead configuration may also be employed in a trans-septal manner to achieve left ventricular treatment of left bundle branch block and/or left ventricular myocardial infarctions.

Figure 29:
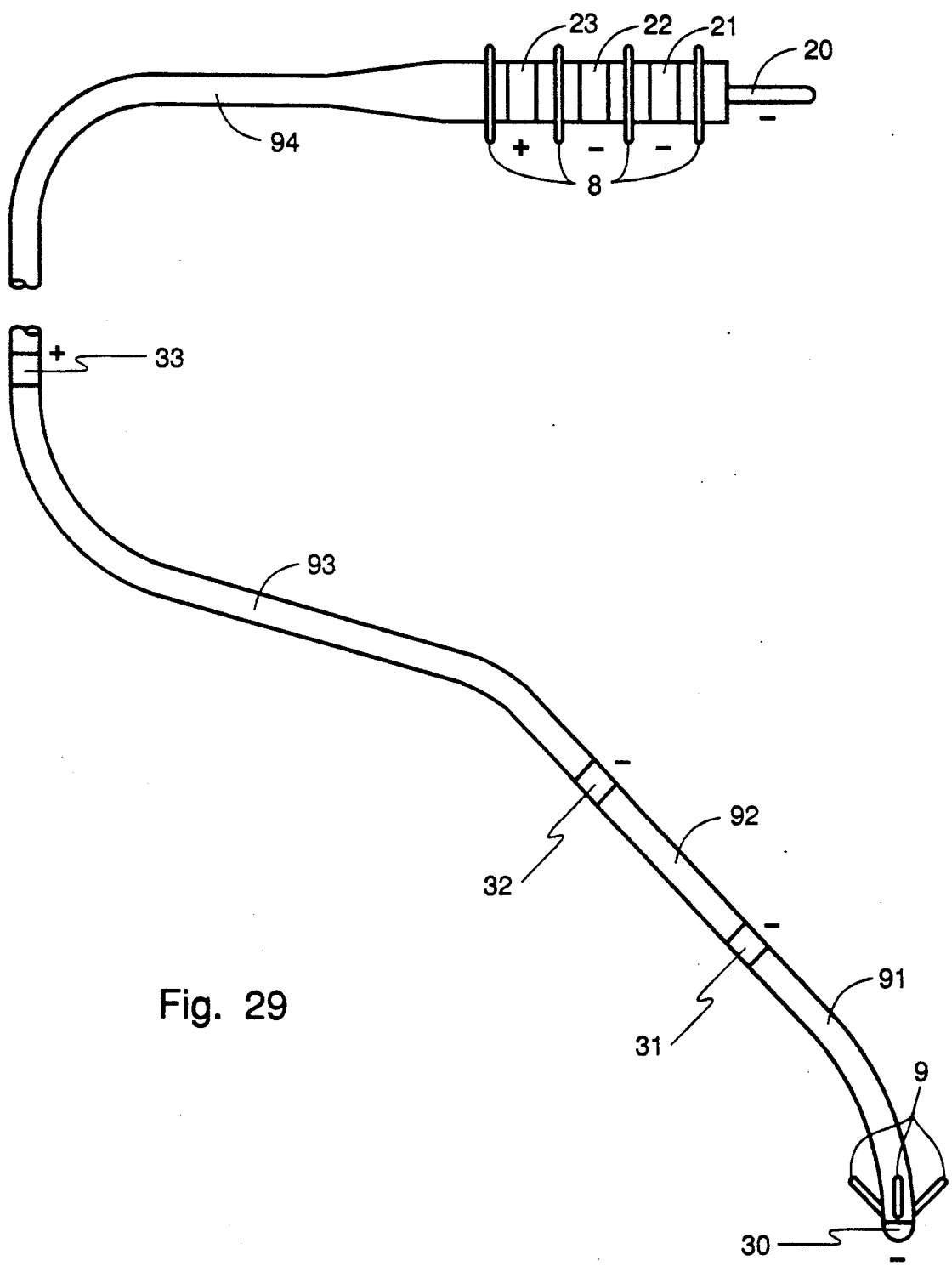
FIG. 29 is a front view showing a three focus, four wire pacing lead for use with the circuitry shown in FIGS. 20, 21 and 22, with a ground electrode that lies outside of the ventricular chamber.

FIG. 29 illustrates an implantable lead with the same basic configuration as that of FIG. 23a modified to relocate ground electrode 33 to a point on the lead which is not within the ventricular chamber where it is less likely, than a unipolar ground, to be in electrical contact with skeletal muscle. During bipolar operation this novel ground location provides a larger sensing field (distance between the positive and negative electrodes) than can be obtained with bipolar sensing through a ground electrode previously located within the ventricular chamber. This configuration may reduce the sensing difficulties that have been encountered with small conventional bipolar sensing fields. By moving the ground electrode 33 to a location where it is considerably less likely to come into electrical contact with skeletal muscle, the complications of skeletal muscle stimulation, inhibition and tracking, which have occurred during conventional unipolar pacing, where the ground is located on the pulse generator case are reduced. It is important to note that this novel location of ground electrode 33 can be applied to conventional pacing or ventricular sequential pacing with equal effect and value. Two or more grounds may be employed simultaneously during pacing or sensing to eliminate muscle stimulation or interference which may occur with the use of a unipolar ground.

Figure 30A:
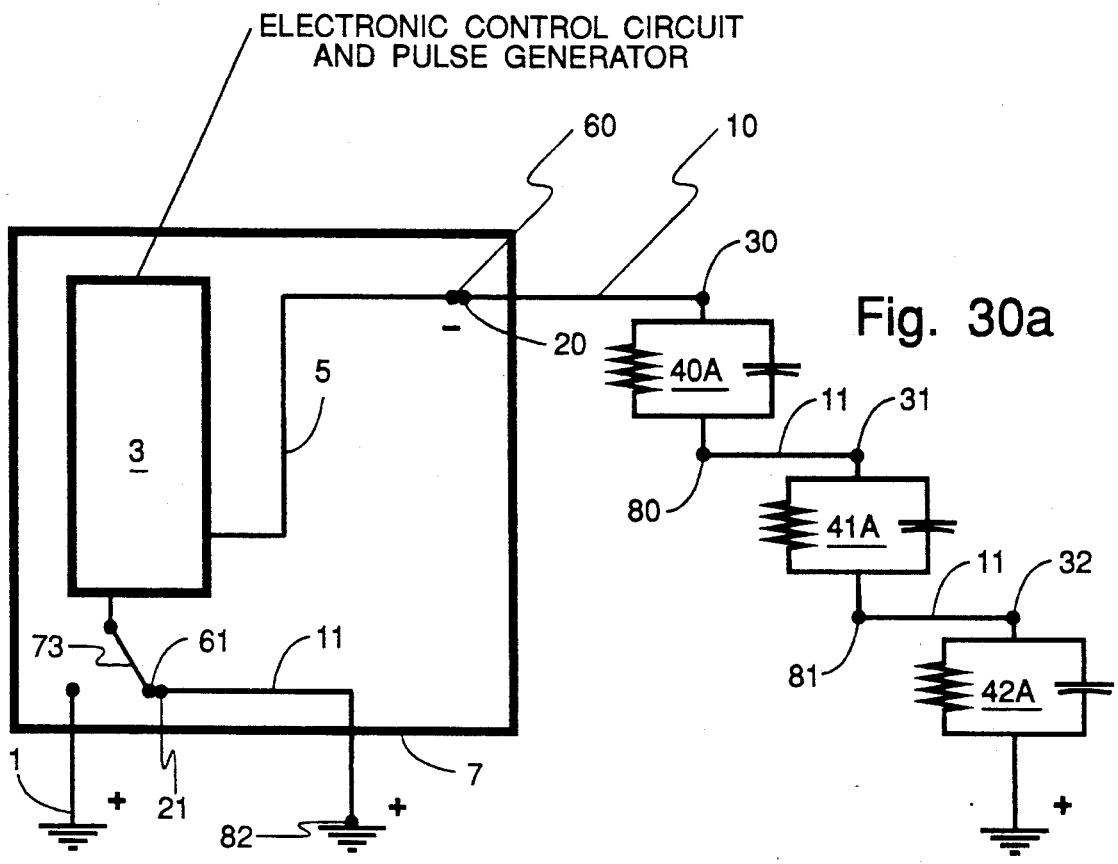
FIG. 30a is an electrical schematic of a two wire, single circuit, three focus ventricular sequential pacing system with the pacing foci arranged in series during pacing
Figure 30B:
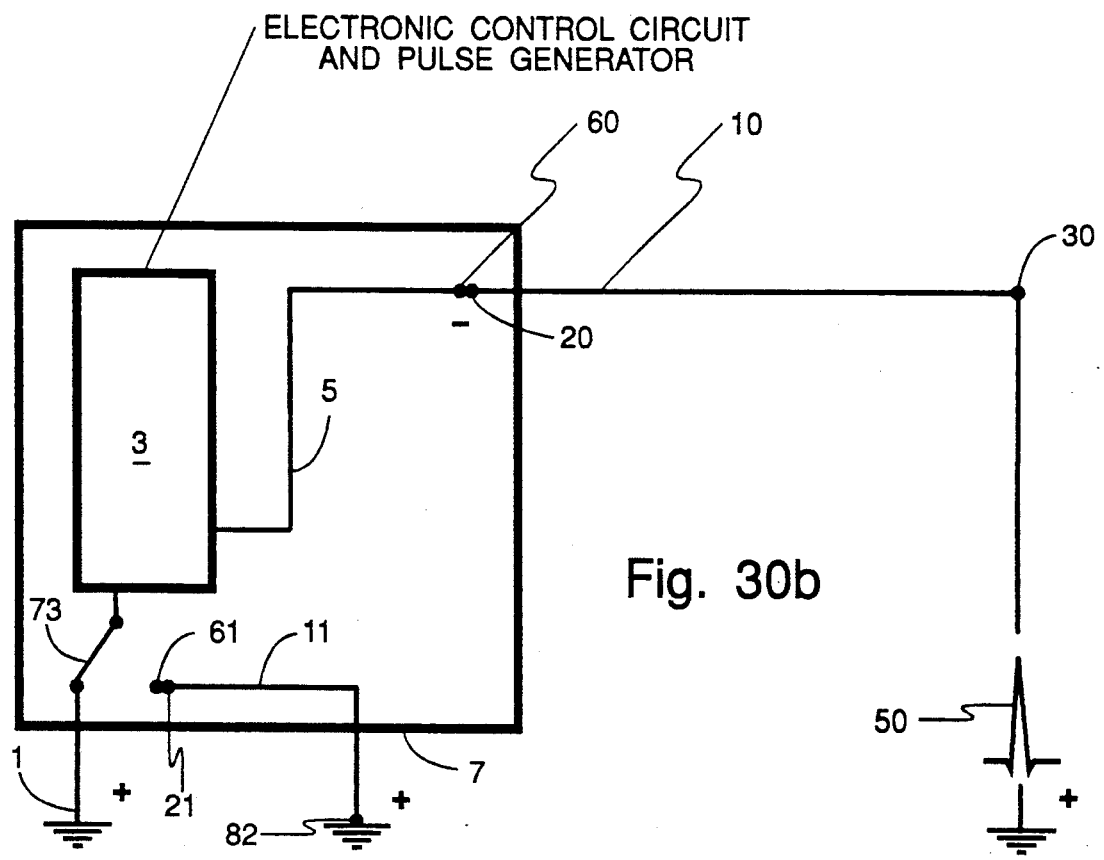
FIG. 30b is an electrical schematic of the same circuitry employed in FIG. 30a during sensing through a single focus as determined by the ground switch positon during sensing.
Figure 31:
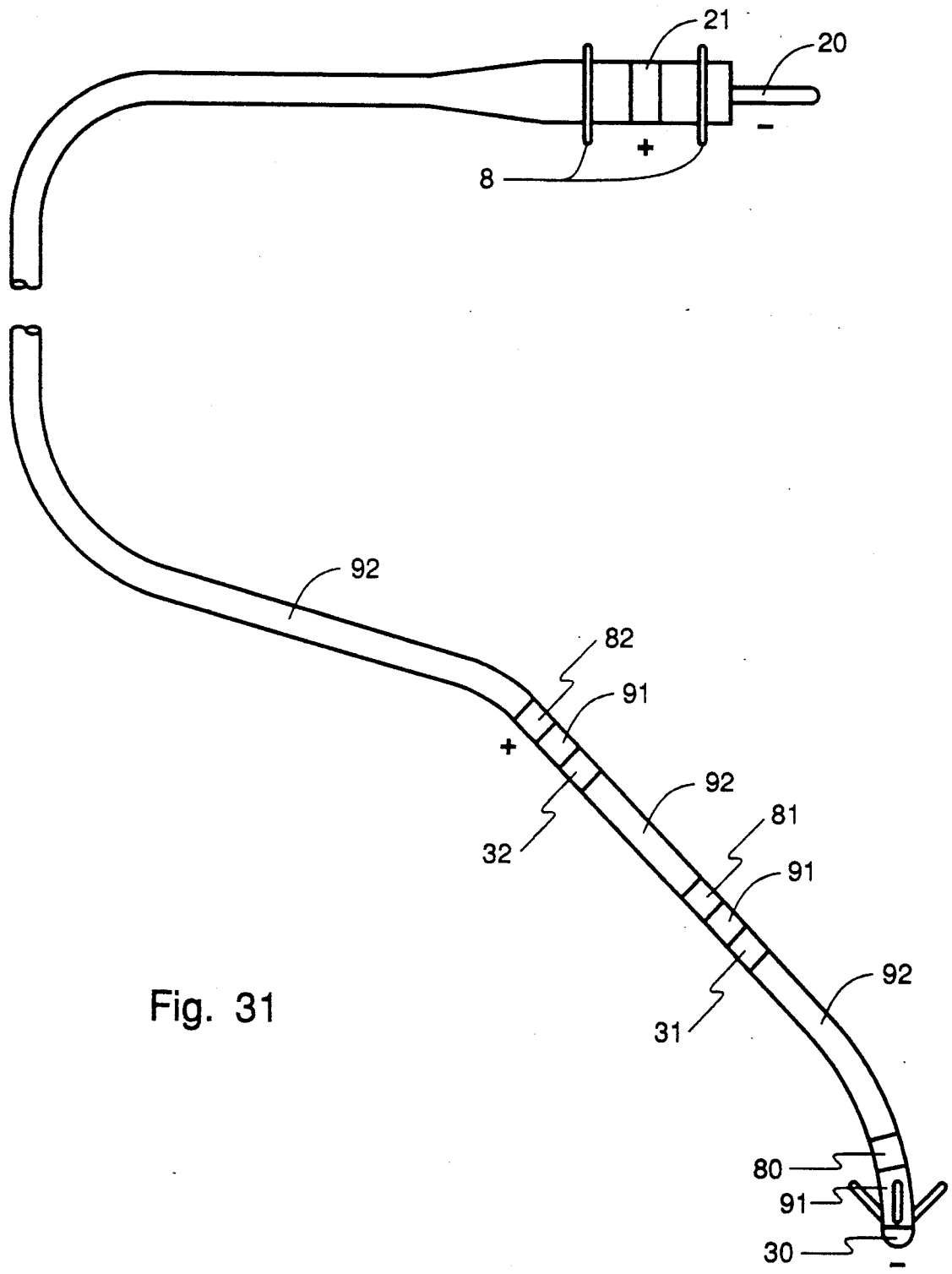
FIG. 31 is a front view showing a three focus, two wire pacing lead for use with the circuitry shown in FIGS. 30a and 30b.

FIGS. 30a, 30b and 31 illustrate a ventricular sequential pacing system where pacing foci 40A, 41A and 42A are arranged in a series electrical configuration. As shown in FIG. 30a, pin 20 is electrically connected to circuitry feedthrough output 5 by means of a set screw or other suitable connection means 60. Wire 10 is electrically connected to pin 20 and tip electrode 30. A length of wire 11 is electrically connected between electrodes 80 and 31. A length of wire 11 is electrically connected between electrodes 81 and 32. A length of wire 11 is electrically connected between electrode 82 and electrical contact 21. All lengths of wire 11 are electrically insulated from wire 10 by insulation 91 and electrically insulated from tissue and body fluids by insulation 92. Pulse generator circuitry including power source 3 has its negative output feedthrough wire 5 electrically connected to electrical connection means 60 and has as its positive ground terminal one pole of programmable switch 73. The other poles of switch 73 may connect the circuitry ground with either electrical contact 21, which is electrically connected to switch 73 by a set screw or other suitable connection means 61, or the pacemaker case ground 1, dependent upon its programmed position during either pacing or sensing. FIG.

30a illustrates pacing occurring with switch 73 programmed to connect the circuitry ground to connection means 61. As shown in FIG. 30b, sensing occurs with switch 73 programmed to connect the circuitry ground to the unipolar case ground 1. Referring to FIGS. 30a and 31, electrode 30 is in electrical contact with ventricular muscle and forms pacing focus 40A between electrode 30 and electrode 80. Similarly, electrode 31 is in electrical contact with ventricular muscle and forms pacing focus 41A between electrode 31 and electrode 81. Electrode 32 is similarly in electrical contact with ventricular muscle and forms pacing focus 42A between electrode 32 and electrode 82. As shown in FIG. 30b, sensing focus 50 is formed between electrode 30 and the unipolar case ground 1.

In the foregoing system, electrodes 30 and 80 are located very close to each other on the lead in order to produce a very small pacing focus 40A, with the intention of lowering focus power consumption as compared to systems with wider spacing. By employment of this close spacing configuration a decrease in ventricular muscle impedance is obtained by decreasing the mass of ventricular muscle and blood between the electrodes 30 and 80 while allowing at least one ventricular muscle cell to be activated. However, a closely spaced configuration of electrodes 30 and 80 produces a small sensing field which in many cases will not yield reliable sensing signals through its electrical pathway. Therefore, a sensing pathway is provided with a large sensing field between electrode 30 and pacemaker case ground 1 as shown in FIGS. 30b and 31. Closely spaced, may be defined as too close to produce reliable sensing signals when employed with current pulse generator systems. Similarly, electrodes 31 and 81, and electrodes 32 and 82, are closely spaced to form pacing foci 41A and 42A, respectively. One or more closely spaced pacing foci may be employed in this series pacing configuration and more than one series combination of pacing foci may be employed in parallel. It is important to note that closely spaced, power efficient pacing foci can also be employed in conventional pacing systems as can be demonstrated by referring to FIG. 30a by eliminating pacing foci 41A and 42A, electrodes 31, 32, 81 and 82, and employing wire 11 to electrically connect electrode 80 to electrical contact 21.

FIGS. 30a and 30b and 31 describe a ventricular sequential pacing system where pacing foci 40A, 41A and 42A will experience equal current flow with a voltage drop across each proportional to the ventricular impedance each experiences. Therefore, focus 40A will pace at a higher voltage than focus 41A, and focus 41A will pace at a higher voltage than 42A. The voltage threshold of each pacing focus may vary, as explained hereinbefore. Thus pacing will be accomplished through one or more foci dependent upon the magnitude of the programmed voltage and the threshold values obtained. Atrial or sensor indicated rate ranges may be employed to trigger voltage increases which add pacing foci according to the threshold values obtained. Closely spaced electrodes are intended to produce lower power consumption than could otherwise be obtained with other one or multiple focus pacing configurations. Conventional pacing may also be accomplished with this circuitry by programming switch 73 to the unipolar ground position 1 during pacing and sensing.

Figure 32:
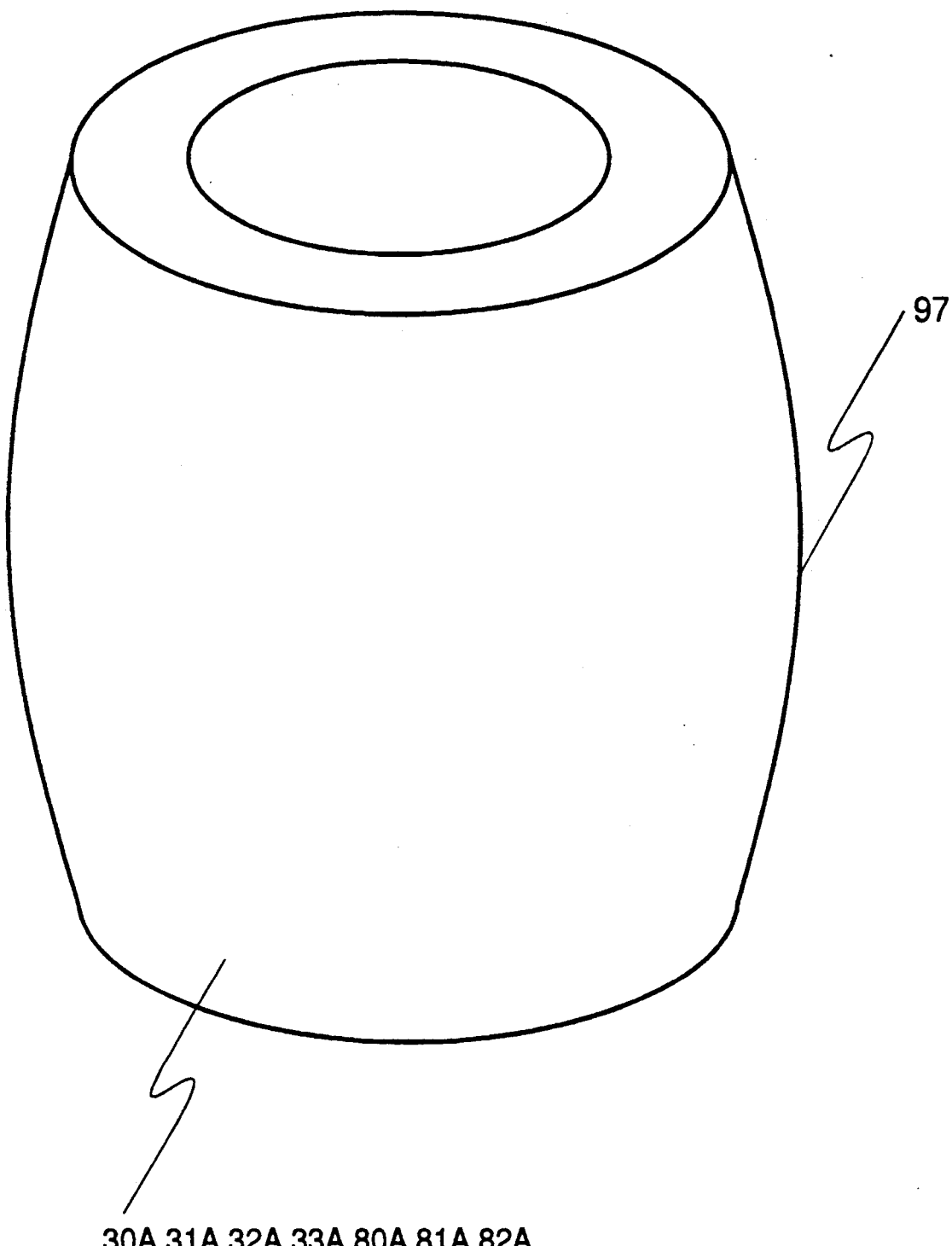
FIG. 32 is an isometric view of an electrode in accordance with an alternative embodiment of the present invention.

FIG. 32 illustrates a novel shape for electrodes 30A, 31A, 32A, 33A, 80A, 81A and 82A with their outer surfaces 97 curved outwardly to yield the desirable properties of hemispherical tip electrodes.

Simultaneous firing of widely separated cells along a ventricular wall or the septum or a combination of both may also be accomplished by pacing through an individual pacing electrode which is considerably greater in surface area than the positive electrode of a conventional bipolar pacing lead or electrodes 30, 31, 32, 33, 80, 81 or 82. One example would be an electrode covering a greater surface area of the leads which are shown to obtain simultaneous firing of widely separated cells along the ventricular septum or walls or a combination of both.

While the ventricular sequential pacemaker systems described hereinbefore are particularly shown with their electrodes in contact with the ventricular endocardial surface, they may also be employed with ventricular epicardial electrodes. When employed with ventricular epicardial electrodes access to the left ventricular wall may prove advantageous under certain patient circumstances.

While the sequential pacemaker systems described hereinbefore are particularly shown applied to ventricular muscle it is intended that they may be applied in the atrial chambers and in any muscle or nerve where control of the sequence or continuity of its contraction is desired and beneficial. It is also intended that ventricular sequential pacemaker systems will be employed in combination with atrial pacing circuitry which is timed to precede selected ventricular foci at a selected interval or intervals in order to produce atrio-ventricular pacing modes in combination with ventricular sequential pacing and/or atrial sequential pacing.

Figure 16:
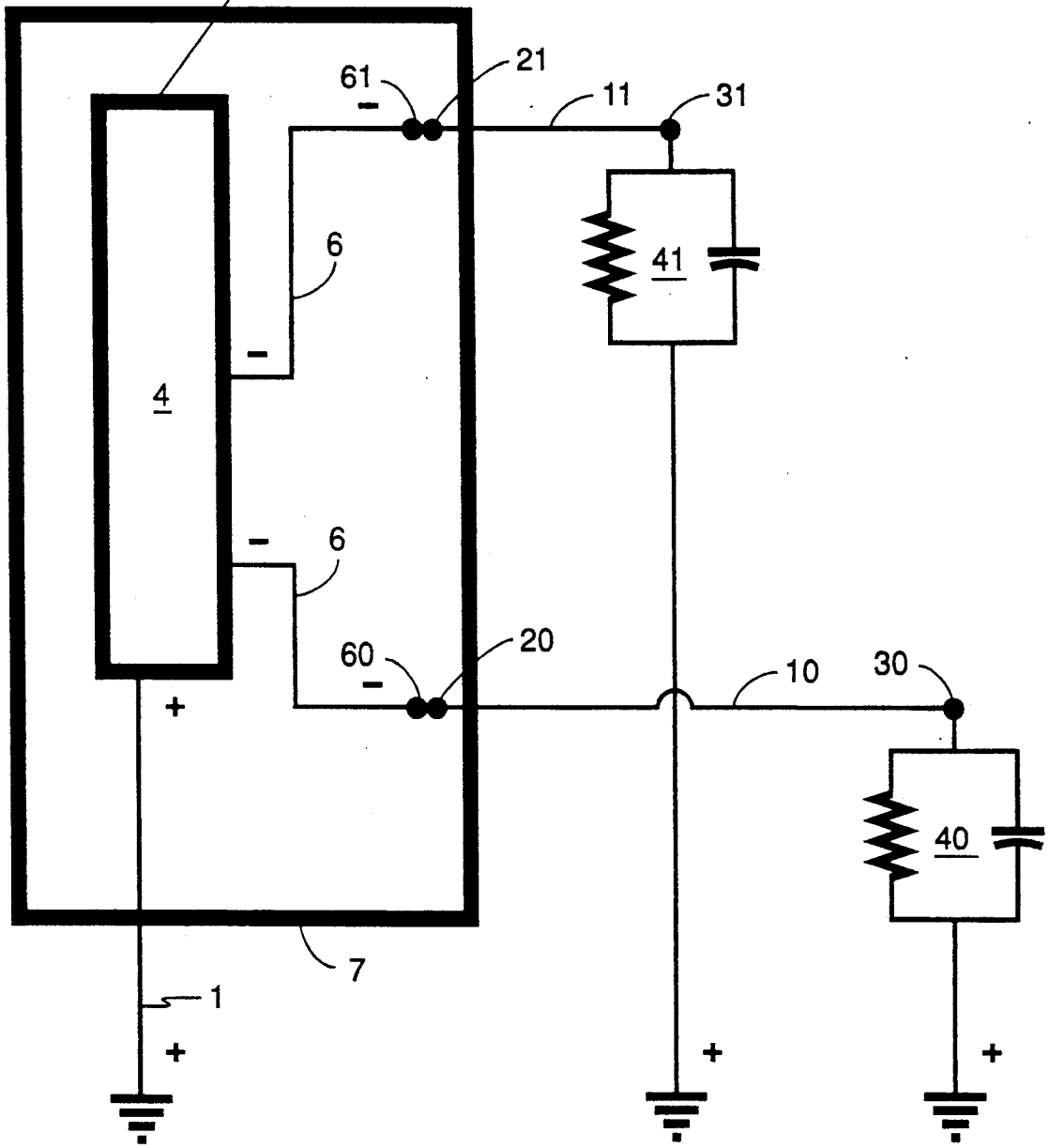
FIG. 16 is an electrical schematic of a dual wire and circuit, twin focus ventricular sequential pacing system during pacing.
Figure 17:
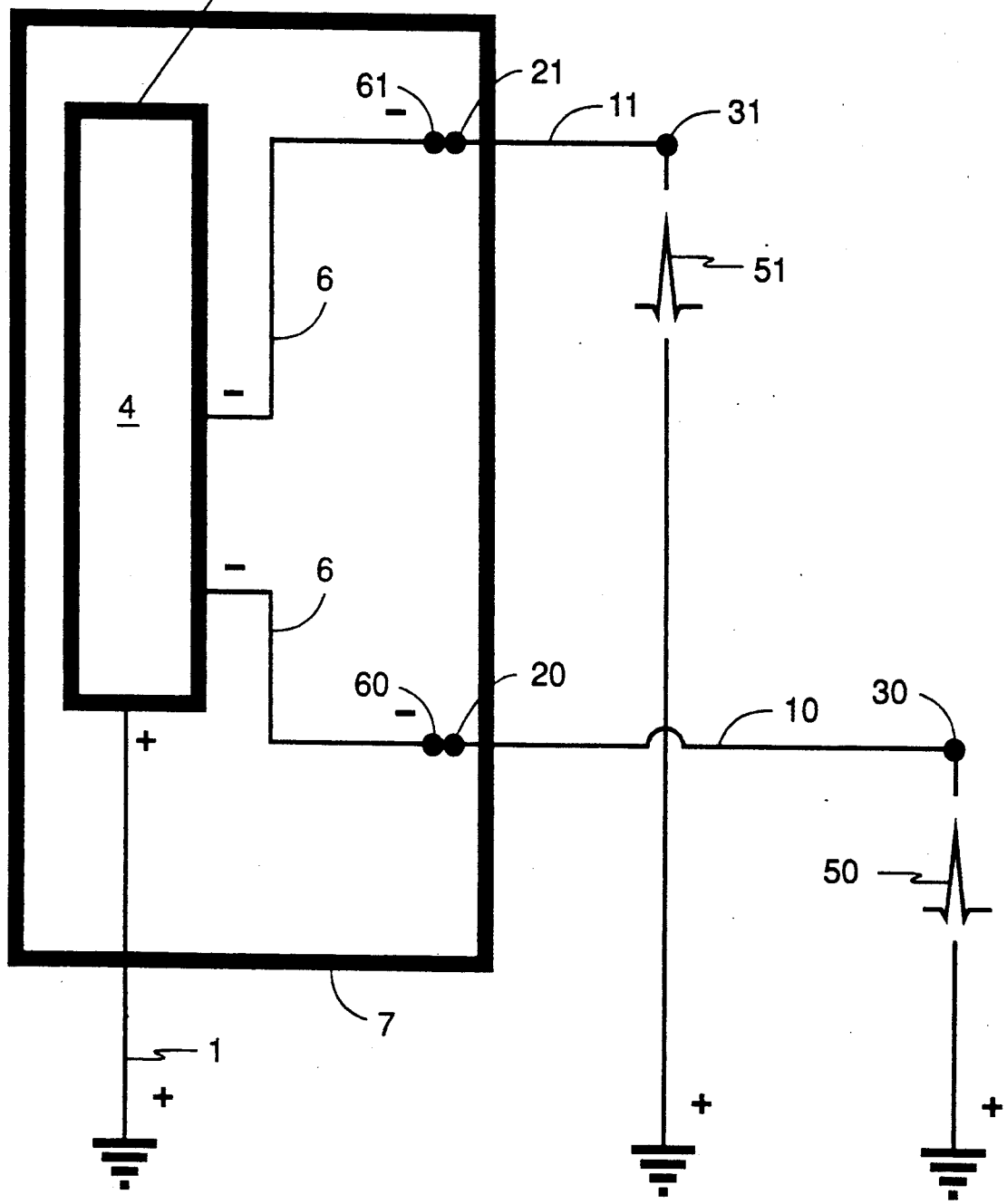
FIG. 17 is an electrical schematic of a dual wire and circuit, twin focus ventricular sequential pacing system during sensing.
Figure 18:
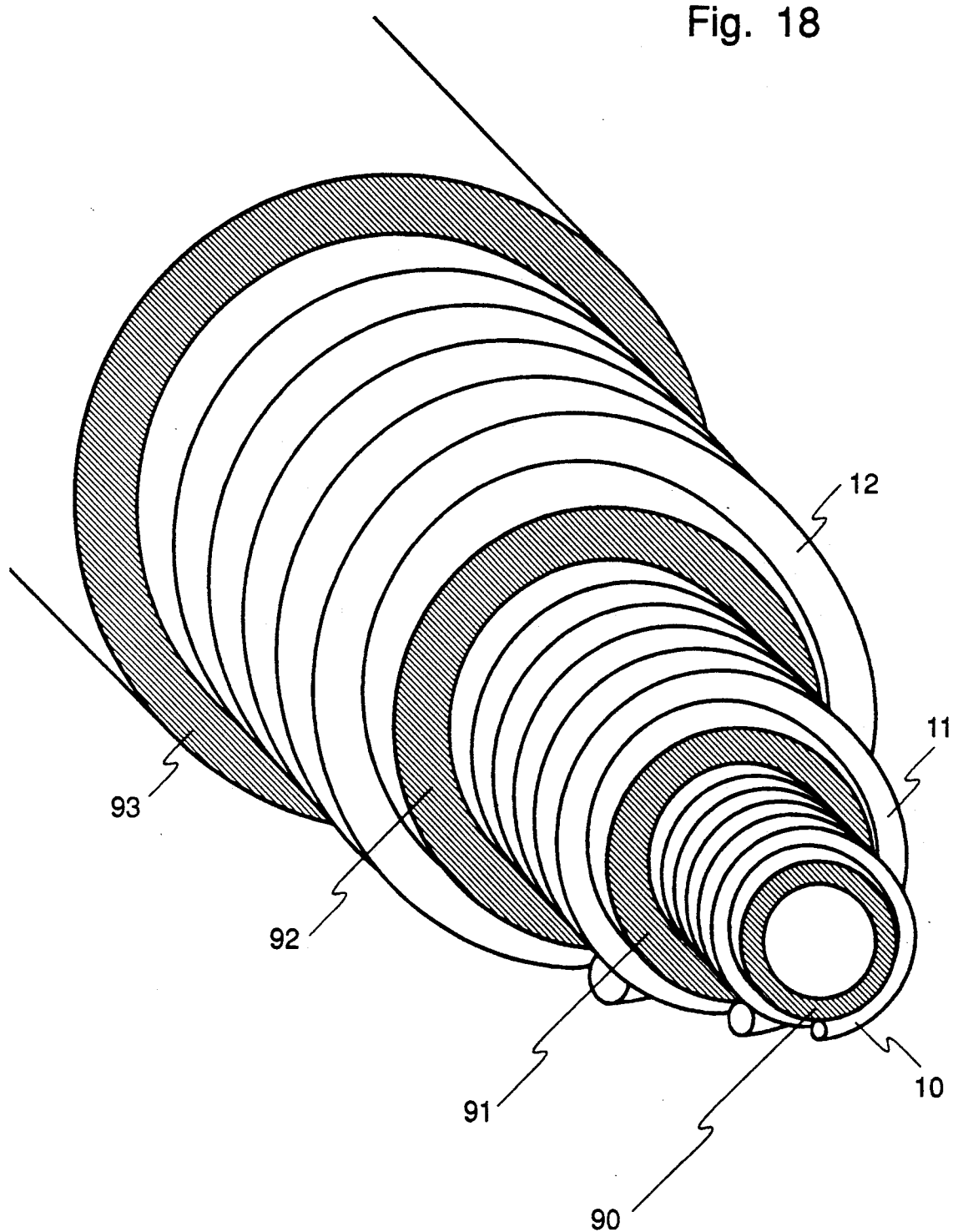
FIG. 18 is a partial isometric cutaway view showing a coaxial winding method for construction of ventricular sequential pacing leads.

While programmable switches 70, 71, 72 and 73 are particularly shown applied to the single output 8 of pulse generator circuitry 3 in FIGS. 20 and 21, they may also be incorporated in the dual output 6 configuration of pulse generator circuitry 4 as shown in FIGS. 16 and 17. Similarly all particular elements of the ventricular sequential pacing systems described herein, are intended to be employed solely or in selected combinations with others to produce the most effective pacing system for a particular patient or groups of patients with a particular disease. While the invention has been particularly shown and described with reference to preferred embodiments thereof, it should be understood by those skilled in the art that changes in the form and detail may be made therein without departing from the spirit and the scope of the invention.

I claim:

1. A method for improving the ventricular function of the heart of a patient comprising the steps of:
   (a) monitoring the electrocardiogram of a patient to determine the duration of the patient's ZRS complex;
   (b) introducing a lead incorporating at least two electrodes of the same polarity thereon for electrical contact with ventricular muscle, each electrode electrically connected to a different lead terminal;
   (c) manipulating said lead to position at least two of said electrodes in electrical contact with said ventricular muscle;
   (d) electrically connecting all said lead terminals to an implantable pulse generator incorporating noninvasive means for selective pacing through each terminal from at least one output pole and electrically connecting at least one electrical group location, or polarity opposite to that of said electrodes, to the other pole of said pulse generator to complete each selected electrical circuit;

(e) providing pacing pulses from said pulse generator to at least two selected terminals, one at a time, at a constant rate determined to stimulate said ventricular muscle in the absence of ventricular fusion;

(f) noninvasevely positioning the location of the pacing pulse by employing said pulse generator noninvasive means to select the one of said terminals that produces the minimum QRS duration with respect to said electrode locations on said lead;

(g) setting said implantable pulse generator at a desired predetermined time interval;

sensing intrinsic cardiac signals from at least one said terminal during a cardiac cycle; and employing the first of said cardiac signal sin the electronic control circuit of said pulse generator to inhibit the deliverance of pacing pulses to said selected terminal upon occurrence of said first cardiac signal within said predetermined time interval and cause the deliverance of pacing pulses to said selected terminal upon the absence of any said cardiac signal with said predetermined time interval.

2. A method for improving the ventricular function of the heart of a patient comprising the steps of:

(a) monitoring the electrocardiogram of a patient to determine the duration of the patient's QRS complex:

(b) introducing a lead incorporating at least two electrodes of the same polarity thereon for electrical contact with the ventricular muscle, each electrode electrically connected to a different lead terminal;

(c) manipulating said lead to position at least two of said electrodes in electrical contact with said ventricular muscle;

(d) electrically connecting each terminal to at least one output pole of a pulse generator and electrically connecting at least one electrical group location, of polarity opposite to that of said electrodes, to the other pole of said pulse generator in order to complete each electrical circuit;

(e) providing pacing pulses from said pulse generator to at least one selected terminal, one at a time, at a constant rate determined to stimulate said ventricular muscle in the absence of ventricular fusion;

(f) analyzing said selected electrode positions to determine their respective resultant QRS durations and, if desired, further manipulating said lead to re-position said electrodes and analyzing such new positions to determine if a shorter resultant QRS duration is obtained;

(g) electrically connecting all said lead terminals to an implantable pulse generator incorporating noninvasive means for selective pacing through each terminal from at least one output pole and electrically connecting at least one electrical ground location, of polarity opposite to that of said electrodes, to the other pole of said implantable pulse generator to complete each selected electrical pacing circuit;

(h) providing pacing pulses from said implantable pulse generator to at least two selected terminals, one at a time, at a constant rate determined to stimulate said ventricular muscle in the absence of ventricular fusion;

(i) noninvasively positioning the location of the pacing pulse by employing said implantable pulse generator noninvasive means to select the one of said terminals that produces the minimum QRS duration with respect to said electrode locations on said lead;

(j) setting said implantable pulse generator at a desired predetermined time interval;

sensing intrinsic cardiac signals from at least one said terminal during a cardiac cycle; and (l) employing the first of said cardiac signals in the electronic control circuit of said pulse generator to inhibit the deliverance of pacing pulses to said selected terminal upon occurrence of said first cardiac signal within said predetermined time interval and cause the deliverance of pacing pulses to said selected terminal upon the absence of any said cardiac signal within said predetermined time interval.

3. The method of claim 2 wherein at least two of said electrodes on said lead are connected to one lead terminal.

4. The method of claim 2 wherein said step (c) of manipulating said lead includes positioning the end of said lead at a ventricular apex.

5. The method of claim 2 wherein said step (f) of analyzing said electrode positions includes manipulating said lead in an endocardial position within a ventricular chamber to position one electrode at a point to yield the minimum QRS duration possible as compared to QRS durations obtained when pacing at any other point.

6. A method for improving the ventricular function of the heat of a patient comprising the steps of:

(a) monitoring the electrocardiogram of a patient to determine the duration of the patient's QRS complex:

(b) introducing a lead incorporating at least two electrodes of the same polarity thereon for electrical contact with ventricular muscle, each electrode electrically connected to a different lead terminal;

(c) manipulating said lead to position at least two of said electrodes in electrical contact with said ventricular muscle; (d) electrically connecting all said lead terminals to an implantable pulse generator incorporating noninvasive means for selective pacing through any combination of said terminals or an individual terminal, from at least one output pole and electrically connecting at least one electrical ground location, of polarity opposite to that of said electrodes, to the other pole of said pulse generator to complete the electrical circuits selected and to provide simultaneous pacing pulses to said selected combinations of terminals;

(e) providing pacing pulses from said pulse generator to a selected individual terminal or any selected combination of terminals, one selection at a time, at a constant rate determined to stimulate said ventricular muscle in the absence of ventricular fusion;

(f) noninvasively positioning the location of the pacing pulses by employing said pulse generator to select the combination of said terminals or individual terminal that produces the minimum QRS duration with respect to said electrode locations on said lead;

(g) setting said implantable pulse generator at a desired predetermined time interval;

(h) sensing intrinsic cardiac signals from at least one said terminal during a cardiac cycle; and (i) employing the first of said cardiac signals in the electronic control circuit of said pulse generator to trigger the deliverance of pacing pulses to said selected terminals simultaneous with the occurrence of said first intrinsic signal within a predetermined time interval and cause the deliverance of simultaneous pacing pulses to said selected terminals upon the absence of any said cardiac signal within said predetermined time interval.

7. A method for improving the ventricular function of the heart of a patient comprising the steps of:
(a) monitoring the electrocardiogram of a patient to determine the duration of the patient's QRS complex:
(b) introducing a lead incorporating at least two electrodes of the same polarity thereon for electrical contact with ventricular muscle, each electrode electrically connected to a different lead terminal;
(c) manipulating said lead to position at least two of said electrodes in electrical contact with said ventricular muscle;
(d) electrically connecting selected combinations of said terminals or individual terminals in turn to at least one output pole of a pulse generator and electrically connecting at least one electrical ground location, of polarity opposite to that of said electrodes, to the other pole of said pulse generator in order to complete the electrical circuits selected and to provide simultaneous pacing pulses to said selected combinations of terminals;
(e) providing pacing pulses from said pulse generator to a selected individual terminal or any selected combination of terminals, one selection at a time, at a constant rate determined to stimulate said ventricular muscle in the absence of ventricular fusion;
(f) analyzing said selected electrode positions to determine their respective resultant QRS durations and, if desired, further manipulating said lead to re-position said electrodes and analyzing such new positions to determine if a shorter resultant QRS duration is obtainable;
(g) electrically connecting all said lead terminals to an implantable pulse generator incorporating noninvasive means for selective pacing through any combination of said terminals or an individual terminal, from at least one output pole and electrically connecting at least one electrical ground location, of polarity opposite to that of said electrodes, to the other pole of said implantable pulse generator to complete the electrical circuits selected and to provide simultaneous pacing pulse to said selected combinations of terminals;
(h) providing pacing pulses from said implantable pulse generator to a selected terminal or any selected combination of terminals, one selection at a time, at a constant rate determined to stimulate said ventricular muscle in the absence of ventricular fusion;
(i) noninvasively positioning the location of the pacing pulses by employing said implantable pulse generator noninvasive means to select the combination of said terminals or an individual terminal that produces a desired QRS duration with respect to said electrode locations on said lead;
(j) setting said implantable pulse generator at a desired predetermined time interval;
sensing intrinsic cardiac signals from at least one said terminal during a cardiac cycle; and
(l) employing the first and said cardiac signals in the electronic control circuit of said pulse generator to trigger the deliverance of pacing pulses to said selected terminals simultaneous with the occurrence of said first intrinsic signal within a predetermined time interval and cause the deliverance of simultaneous pacing pulses to said selected terminals upon the absence of any said cardiac signal within said predetermined time interval.

8. The method of claim 7 wherein said step (i) of noninvasively positioning includes selecting the combination of terminals that produces the minimum QRS duration with respect to the electrodes' locations on the lead as determined by said monitoring step (a).

9. The method of claim 7 wherein said step (l) of employing said cardiac signals comprises employing the first of said cardiac signals in the electronic control circuit of said pulse selected electrodes upon occurrence of said first cardiac signal with said predetermined time interval and cause the deliverance of simultaneous pacing pulses to said selected electrodes upon the absence of any said cardiac signal within said predetermined time interval.

10. The method of claim 7 wherein said step (c) of manipulating said lead includes positioning a first said electrode in an area of said ventricular muscle where early activation is desired and positioning at least one other said electrode in an area or areas of the ventricular muscle where avoidance of late activation is desired, as determined by the QRS interval resulting from said analyzing step (f).

11. The method of claim 7 wherein said step (c) of manipulating said lead includes positioning certain electrodes at positions to produce a more desirable ventricular motion.

12. The method of claim 7 wherein said step (c) of manipulating said lead includes positioning said electrodes within a ventricular chamber.

13. The method of claim 12 wherein said step (f) of analyzing said electrode positions includes positioning two of said electrodes in contact with ventricular muscle to produce a QRS duration that is shorter than the QRS duration obtained by pacing at any individual point in the ventricular muscle.

14. The method of claim 12 wherein said step (c) of manipulating said lead includes positioning one electrode at the ventricular apex and another electrode at a midseptal position.

15. The method of claim 14 wherein said step (c) of manipulating said lead includes positioning at least one additional electrode in a septal position between said two previously positioned electrodes, to produce a more desirable ventricular motion.

16. The method of claim 7 wherein said step (l) of employing the first of said cardiac signals comprises delivering a pacing pulse to a second terminal at a programmed time delay interval from the occurrence of said first cardiac signal at a first terminal within said predetermined time interval and delivering a pacing pulse to said first terminal upon the absence of said first cardiac signal at said first terminal within said predetermined time interval followed by a second pacing pulse delivered to said second terminal at expiration of said delay interval.

17. The method of claim 16 wherein said delayed pacing pulses are inhibited by intrinsic cardiac activity occurring at the second terminal within the delay interval.

18. The method of claim 17 wherein the electrical power delivered to each terminal and sensitivity of each terminal are independently and noninvasively adjustable.

19. The method of claim 17 wherein said implantable pulse generator is simultaneously connected to at least two ground locations of the same polarity.

20. The method of claim 19 wherein at least one of said ground locations is on the lead and outside of a ventricular chamber.

21. The method of claim 20 wherein said implantable generator incorporates noninvasive means for selection of said ground locations or location during pacing.

22. The method of claim 21 wherein said implantable generator incorporates noninvasive means for selection of said ground locations or location during sensing.

23. The method of claim 17 wherein the programmed time delay interval is adjustable from about 0 to about 75 msec.

24. The method of claim wherein said implantable pulse generator incorporates a rate adaptive sensor to automatically adjust said predetermined interval in response to physiologic indications of cardiac demand.

25. The method of claim 24 wherein said delay interval is automatically adjusted in response to said physiologic indications of cardiac demand.

26. The method of claim 17 wherein said lead incorporates at least two of said electrodes electrically connected to one of said lead terminals.

27. The method of claim 26 wherein said lead incorporates at least two terminals each electrically connected to at least two 28. The method of claim 16 wherein at least two delays are employed between at least three terminals.

29. The method of claim 28 wherein the delayed pulse are inhibited by intrinsic cardiac activity occurring at their respective terminals within their respective delay intervals.

30. The method of claim 29 wherein the electrical power delivered to each terminal and sensitivity of each terminal are independently and noninvasevely adjustable.

31. The method of claim 30 wherein each delay interval is independently adjustable and the sum of the multiple delays is from about 0 to about 75 msec.

32. The method of claim 31 wherein said implantable pulse generator incorporates a rate adaptive sensor to automatically adjust said predetermined interval in response to physiologic indications of cardiac demand.

33. The method of claim 32 wherein said delay intervals are automatically adjusted in response to physiologic indications of cardiac demand.

34. The method of claim 31 wherein said lead incorporates at least two electrodes electrically connected to one of said lead terminals.

35. The method of claim 34 wherein said lead incorporates at least two terminals each electrically connected to at least two electrodes.

36. A lead adapted for connection to a pulse generator comprising at least two electrodes thereon for electrical contact with the endocardial surface of a ventricular chamber and a preformed curvature within the ventricular chamber, said preformed curvature beginning at the distal end of said lead, extending through an approximate arc of forth five degrees and having a radius of curvature of approximately one inch, for the purpose of facilitating the placement of said electrodes in desired locations by manipulation of said lead.

37. The apparatus of claim 36 further comprising a second preformed curvature proximal to said preformed curvature within the ventricular chamber.

38. An electrode for location on a cylindrical portion of a pacing lead in electrical contact with a ventricular chamber incorporating an outwardly curved contacting surface of said electrode's pacing threshold and capability of sensing intrinsic cardiac signals.

39. Cardiac electrical stimulation apparatus comprising: first means for sensing a first ventricular depolarization at a first ventricular location; second means having output means and responsive to said first sensing means for providing a stimulating impulse to said first ventricular location upon the absence of said first depolarization within a predetermined time interval; third means for sensing a second ventricular depolarization at a second ventricular location; and fourth means having output means and responsive to said third means for providing a stimulating impulse to said second ventricular location upon the absence of said second ventricular depolarization within said predetermined interval and a delay interval.

40. Apparatus according to claim 39 wherein said first and second ventricular locations are on the endocardial surface of a ventricular chamber.

41. Apparatus according to claim 39 wherein said first ventricular location is on the endocardial surface of the ventricular chamber and said second ventricular location is on the epicardial surface of a ventricular chamber.

42. Apparatus according to claim 39 additionally comprising: fifth means for sensing a third ventricular depolarization at a third ventricular location; and sixth means having output means and responsive to said fifth means for providing a stimulating impulse to said third ventricular location upon the absence of said third ventricular depolarization within said predetermined interval and a second delay interval.

43. Apparatus according to claim 42 additionally comprising: seventh means for sensing a fourth ventricular depolarization at a fourth ventricular location; and eighth means having output means and responsive to said seventh means for providing a stimulating impulse to said fourth ventricular location upon the absence of said fourth ventricular depolarization within said predetermined interval and a third delay interval.

44. Apparatus according to claim 39 wherein said first means senses first ventricular depolarization at least two first ventricular locations and said second means for providing stimulating impulses to said first ventricular locations upon the absence of said first ventricular depolarization within said predetermined time interval.

45. Apparatus according to claim 44 wherein said third means senses second ventricular depolarizations at least two second ventricular locations and said fourth means for providing stimulating impulses to said second ventricular locations upon the absence of a second ventricular depolarization within said predetermined interval and said time delay interval.

46. Cardiac electrical stimulation apparatus comprising: first means for sensing a first ventricular depolarization at a first ventricular location; second means having output means and responsive to said first sensing means for providing a stimulating impulse to said first ventricular location upon the absence of said first depolarization within a predetermined time interval; third means for sensing a second ventricular depolarization at a second ventricular location; and fourth means having output means and responsive to said first and third means for providing a stimulating impulse to said second location at a programmed time delay interval from the occurrence of said first depolarization within said predetermined interval in the absence of said second depolarization within said delay interval and providing a stimulating impulse to said second ventricular location at said time delay interval from the absence of said first depolarization within said predetermined interval in the absence of said second ventricular depolarization within said delay interval.

47. Apparatus according to claim 46 wherein said first means senses first ventricular depolarization at at least two first ventricular locations and said second means for providing stimulating impulses to said first ventricular locations upon the absence of said first ventricular depolarization within said predetermined time interval.

48. Apparatus according to claim 46 wherein said implantable pulse generator is simultaneously connected to at least two ground locations of the same polarity.

49. Apparatus according to claim 46 additionally comprising fifth means for sensing a third ventricular depolarization at a third ventricular location; and sixth means having output means and responsive to said first and fifth means for providing a stimulating impulse to said third location at a second programmed time delay interval from the occurrence of said first depolarization within said predetermined interval in the absence of said third polarization within said second time delay interval and providing a stimulating impulse to said third ventricular location at said second time delay interval from the absence of said first depolarization within said predetermined interval in the absence of said third ventricular depolarization within said second time delay interval.

50. Apparatus according to claim 49 wherein said first, second and third ventricular locations are on the endocardial surface of a ventricular chamber.

51. Apparatus according to claim 50 wherein said first ventricular location is at a ventricular apex, said second ventricular location is at a midseptal position and said third ventricular location is at a septal position between said first and second ventricular locations.

52. Apparatus according to claim 49 additionally comprising seventh means means for sensing a fourth ventricular depolarization at a fourth ventricular location; and eighth means having output means and responsive to said first and seventh means for providing a stimulating impulse to said fourth location at a third programmed time delay interval from the occurrence of said first depolarization within said predetermined interval in the absence of said fourth polarization within said third time delay interval and providing a stimulating impulse to said fourth ventricular location at said third time delay interval from the absence of said first depolarization within said predetermined interval in the absence of said fourth ventricular depolarization within said third time delay interval.

53. Apparatus according to claim 46 wherein said first and second ventricular locations are on the endocardial surface of a 54. Apparatus according to claim 53 wherein said first ventricular location is at a ventricular apex and said second ventricular location is at a midseptal position.

55. Apparatus according to claim 46 wherein said implantable pulse generator incorporates a rate adaptive sensor to automatically adjust said predetermined interval in response to physiologic indications or cardiac demand.

56. Apparatus according to claim 55 wherein said delay interval is automatically adjusted in response to said physiologic indications of cardiac demand.

57. A method for improving the ventricular function of the heart of a patient, presenting with wide QRS complexes of intrinsic origin, comprising the steps of:
  (a) monitoring the electrocardiogram of a patient to determine the duration of the patient's QRS complex;
  (b) introducing a lead incorporating at least two electrodes of the same polarity thereon for electrical contact with ventricular muscle, each electrode electrically connected to a different lead terminal;
  (c) manipulating said lead to position at least two of said electrodes in electrical contact with said ventricular muscle;
  (d) electrically connecting at least two of said individual terminals to at least one output pole of a pulse generator and electrically connecting at least one electrical ground location, of polarity opposite to that of said electrodes, to the other pole of said pulse generator in order to complete each electrical circuit;
  (e) sensing intrinsic cardiac signals from at least one said terminal during a cardiac cycle;
  (f) employing the first of said cardiac signals in the electronic control circuit of said pulse generator to trigger the deliverance of pacing pulses to selected terminals simultaneous with the occurrence of said first intrinsic signal within a predetermined time interval and cause the deliverance of simultaneous pacing pulses to said selected terminals upon the absence of any said cardiac signal within said predetermined time interval;
  (g) providing pacing pulses from said pulse generator to at least one other selected terminal at a rate determined by intrinsic electrical activity in order to stimulate said ventricular muscle in the presence of ventricular fusion;
  (h) analyzing said electrode positions to determine their respective resultant QRS duration as compared to the intrinsic QRS duration and, if desired, further manipulating said lead to re-position said electrodes and analyzing such new positions to determine if a shorter resultant QRS is obtained; and
  (j) providing pacing pulses from said pulse generator to a desired combination of terminals that produces a shorter QRS duration than the patient's intrinsic QRS.

* * * * *